United States Patent
Egami et al.

[11] Patent Number: 6,149,990
[45] Date of Patent: Nov. 21, 2000

[54] CARBOXYLATE DERIVATIVES COMPRISING AN ETHER GROUP AND LIQUID CRYSTAL COMPOSITION COMPRISING THE SAME

[75] Inventors: Yoshiji Egami, Izumi; Masatoshi Fukushima, Minamata; Yasuko Sekiguchi, Ichihara; Makoto Tanimoto, Izumi; Etsuo Nakagawa, Ichihara, all of Japan

[73] Assignee: Chisso Corporation, Osaka, Japan

[21] Appl. No.: 09/117,706

[22] Filed: Aug. 4, 1998

Related U.S. Application Data

[63] Continuation of application No. PCT/JP97/00323, Feb. 7, 1997.

[30] Foreign Application Priority Data

Feb. 7, 1996 [JP] Japan ........................................ 8-45439

[51] Int. Cl.$^7$ .......................... C09K 19/30; C09K 19/20; C07C 69/76; C07C 69/75; C07C 25/13
[52] U.S. Cl. ................ 428/1.1; 252/299.63; 252/299.64; 252/299.65; 252/299.66; 252/299.67; 560/65; 570/129
[58] Field of Search .......................... 252/299.63, 299.64, 252/299.65, 299.66, 299.67; 428/1.1; 560/65; 570/129

[56] References Cited

U.S. PATENT DOCUMENTS 4,925,590  5/1990  Reiffenrath et al. ............... 252/299.61

FOREIGN PATENT DOCUMENTS

| 820 976 A1 | 1/1998 | European Pat. Off. . |
| 57-176943 | 10/1982 | Japan . |
| 61-278589 | 12/1986 | Japan . |
| 63-502284 | 9/1988 | Japan . |
| 2-233626 | 9/1990 | Japan . |
| 4-300861 | 10/1992 | Japan . |
| 5-501895 | 4/1993 | Japan . |
| 7-56132 | 3/1995 | Japan . |
| 07 233113 | 9/1995 | Japan . |
| 7-300585 | 11/1995 | Japan . |
| WO 89/08102 | 9/1989 | WIPO . |
| WO96/32365 | 10/1996 | WIPO . |

OTHER PUBLICATIONS

Derwent–Acc–No.: 1995–133924.

*Primary Examiner*—Shean C. Wu
*Attorney, Agent, or Firm*—McDermott, Will & Emery

[57] ABSTRACT

A compound represented by the following general formula (I), a liquid crystal composition comprising the same, and a liquid crystal element using this liquid crystal composition.

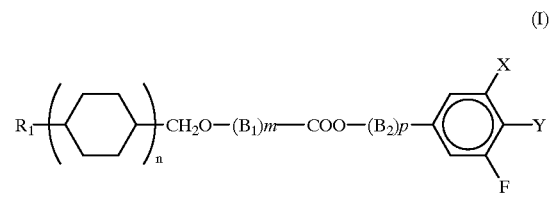

(I)

(wherein $B_1$ and $B_2$ represent independently a trans-1,4-cyclohexylene group or a 1,4-phenylene group wherein at least one hydrogen atom on the six-membered ring is optionally substituted by a halogen atom, Y represents a halogen-substituted alkyl group having 1 to 3 carbon atoms, a halogen-substituted alkoxy group having 1 to 3 carbon atoms, a cyano group, a fluorine atom or a chlorine atom, X represents a fluorine atom, a chlorine atom or a hydrogen atom, $R_1$ represents an alkyl group having 1 to 10 carbon atoms or an alkoxy group having 1 to 10 carbon atoms, n and m represent independently 1 or 2 and p represents 0 or 1.)

The compound of the present invention exhibits a large dielectric anisotropy, low threshold voltage, and favorable temperature-dependency of threshold voltage, as well as a favorable miscibility with a known liquid crystal compound, and therefore a liquid crystal composition comprising the compound can provide low voltage-operable liquid crystal display elements.

11 Claims, No Drawings

CARBOXYLATE DERIVATIVES COMPRISING AN ETHER GROUP AND LIQUID CRYSTAL COMPOSITION COMPRISING THE SAME

REFERENCE TO RELATED APPLICATION

This Application is a continuation of International Application No. PCT/JP97/00323, whose international filing date is Feb. 7, 1997, which in turn claims the benefit of Japanese Patent Application No. 45439/1996, filed Feb. 7, 1996, the disclosures of which Applications are incorporated by reference herein. The benefit of the filing and priority dates of the International and Japanese Applications is respectfully requested.

FIELD OF THE INVENTION

This invention relates to a liquid crystal compound, and more specifically a carboxylate derivative containing an ether group, a liquid crystal composition comprising the compound and a liquid crystal element using the liquid crystal composition.

BACKGROUND OF THE INVENTION

Liquid crystal display elements are used widely in watches, electronic calculators, electronic notebooks, word processors, note book type-personal computers, video cameras equipped with a monitor, car-navigation systems, etc. These liquid crystal display elements utilize optical anisotropy ($\Delta n$) and dielectric anisotropy ($\Delta \epsilon$) of liquid crystal materials. Display systems of the liquid crystal display elements include a twisted nematic (TN) mode, a super twisted nematic (STN) mode, a dynamic scattering (DS) mode, a guest-host mode, DAP (Deformation of Aligned Phases) mode and the like, according to electro-optical effects which are applied to the liquid crystal display element. In any system, it is desirable that a liquid crystal compound shows a liquid crystal phase at a temperature ranging as broad as possible, and it is necessary that a liquid crystal compound is stable against water, heat, air or the like. It is also necessary that a liquid crystal compound shows high miscibility with other liquid crystal compounds. Although a number of liquid crystal compounds have been already known, there is no liquid crystal compounds which satisfy all the above-mentioned conditions at present, and in practice several liquid crystal compounds are used in admixture with non-liquid crystalline compounds.

Recently, there is an increasing need for a low-voltage operation in association with a decreased electric power consumption and miniaturization of a display element, and thus there is in need of a liquid crystal compound having low threshold voltage (Vth). In order to decrease the threshold voltage, it is necessary to increase dielectric anisotropy ($\Delta \epsilon$).

Examples of a liquid crystal compound having large dielectric anisotropy include an ester derivative represented by the following general formula 1) disclosed in WO89/08102.

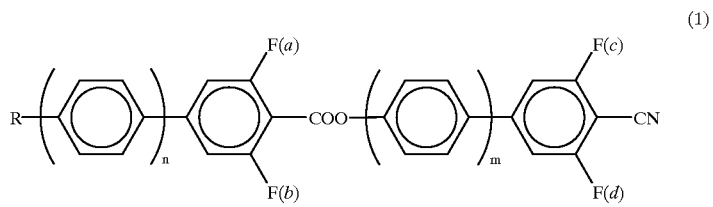

wherein R represents $R_1$, $R_1O$ or $R_1COO$, $R_1$ represents an alkyl group having 1 to 12 carbon atoms, n and m individually represent 0 or 1, (n+m) also represents 0 or 1, a, b, c and d independently represent 0 or 1, and (a+b+c+d) does not represent 0, excluding a case wherein a and b individually represent 0, m represents 0, and one of c and d represents 0, provided that these symbols are different from those used in the present invention and are applied to merely the general formula 1).

However, there is a need for a liquid crystal material which has improved miscibility with known liquid crystal compounds at a low temperature over the compound represented by the general formula 1).

Furthermore, examples of a liquid crystal compound having large dielectric anisotropy include an ester derivative represented by the following general formula 2) disclosed in J.P. KOKAI No. Hei 4-300861.

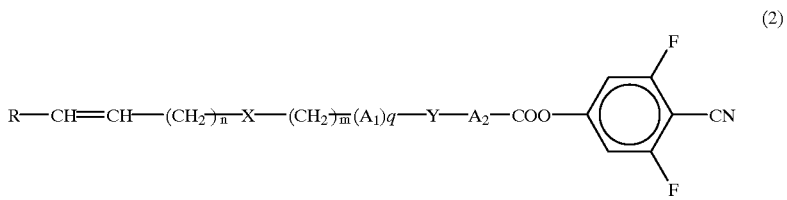

wherein $A_1$ and $A_2$ represent a 1,4-phenylene group or the like, R represents a hydrogen atom or an alkyl group having 1 to 5 carbon atoms, X represents —O—, —CO—O—, —O—CO— or a covalent bond, Y represents —O—, —CO—O—, —O—CO—, a covalent bond or the like, m and n represent 0 to 4, and q represents 0 or 1, provided that these symbols are different from those used in the present invention and are applied to merely the general formula 2).

However the compound represented by the general formula 2) has an unsaturated bond at the one terminal of the molecule and thus it does not have enough heat stability.

Accordingly, there is a need for a liquid crystal material which has an improved heat stability.

DISCLOSURE OF THE INVENTION

Thus, an object of the invention is to solve the above-mentioned problems in the prior art, and to provide a liquid crystal compound having a large dielectric anisotropy, which is chemically stable and has good heat stability, low threshold voltage and favorable temperature-dependency of the threshold voltage as well as good miscibility with other liquid crystal compounds known in the art. Another object of the invention is to provide a liquid crystal composition comprising said liquid crystal compound and a liquid crystal display element using the liquid crystal composition.

The present invention provides a compound of the following general formula (I):

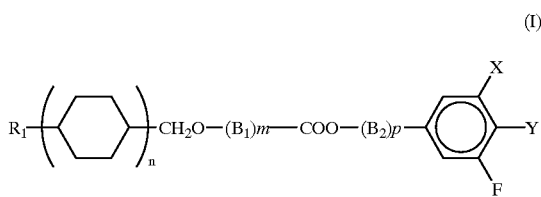

(I)

wherein $B_1$ and $B_2$ represent independently a trans-1,4-cyclohexylene group or a 1,4-phenylene group wherein one or more hydrogen atoms on the six-membered ring are optionally substituted by halogen atoms, Y represents a halogen-substituted alkyl group having 1 to 3 carbon atoms, a halogen-substituted alkoxy group having 1 to 3 carbon atoms, a cyano group, a fluorine atom or a chlorine atom, X represents a fluorine atom, a chlorine atom or a hydrogen atom, $R_1$ represents an alkyl group having 1 to 10 carbon atoms or an alkoxy group having 1 to 10 carbon atoms, n and m represent independently 1 or 2, and p represents 0 or 1.

Preferred compounds according to the present invention are given below.

① A compound of the general formula (I) wherein m represents 1.

② A compound of the general formula (I) wherein $B_1$ represents 1,4-phenylene group wherein one or more hydrogen atoms on the six-membered ring are optionally substituted by halogen atoms, and m represents 1.

③ A compound of the general formula (I) wherein $B_1$ represents 1,4-phenylene group wherein one or more hydrogen atoms on the six-membered ring are substituted by fluorine atoms, and m represents 1.

④ A compound of the general formula (I) wherein $B_1$ represents a trans-1,4-cyclohexylene group, and m represents 1.

⑤ A compound of the general formula (I) wherein m represents 2.

The present invention also provides a liquid crystal composition which comprises at least one compound represented by the general formula (I).

The present invention further provides a liquid crystal composition which comprises at least one compound of the formula (I) and at least one compound selected from the group consisting of the compounds of following formulas (II), (III) and (IV).

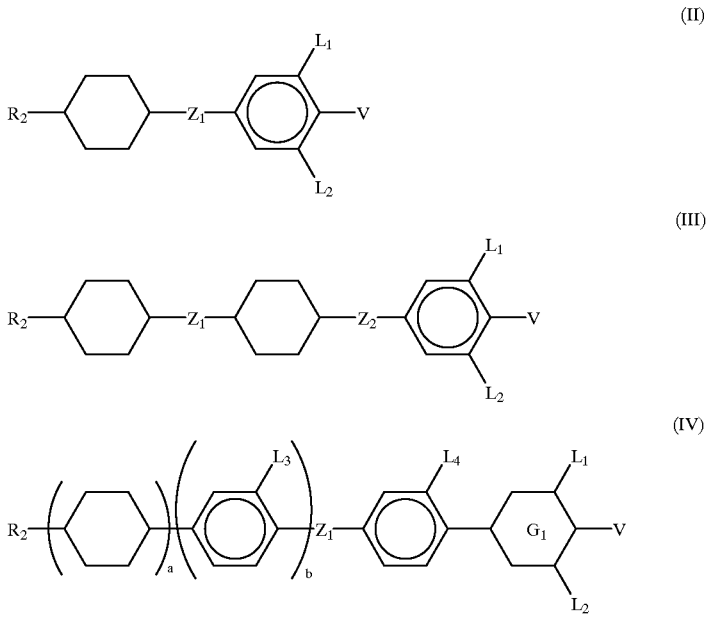

wherein $R_2$ represents an alkyl group having 1 to 10 carbon atoms, V represents F, Cl, $CF_3$, $OCF_3$, $OCF_2H$ or an alkyl group having 1 to 10 carbon atoms, $L_1$, $L_2$, $L_3$ and $L_4$ represent independently H or F, a represents 1 or 2, b represents 0 or 1, $Z_1$ and $Z_2$ represent independently —$CH_2CH_2$—, —CH=CH— or a covalent bond, and ring $G_1$ represents a trans-1,4-cyclohexylene group or 1,4-phenylene group.

The present invention also provides a liquid crystal composition which comprises at least one compound of the formula (I) and at least one compound selected from the group consisting of the compounds of following formulas (V), (VI), (VII), (VIII) and (IX).

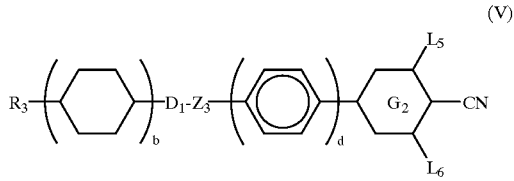
(V)

In the formula (V), $R_3$ represents F, an alkyl group having 1 to 10 carbon atoms or an alkenyl group having 2 to 10 carbon atoms. Any methylene group (—$CH_2$—) in said alkyl or alkenyl group may be replaced by one or more oxygen atoms (—O—), provided that two or more successive methylene groups are not replaced by oxygen atoms. $Z_3$ represents —$CH_2CH_2$—, —CO—O— or a covalent bond, $L_5$ and $L_6$ represent independently H or F, $D_1$ represents a trans-1, 4-cyclohexylene, 1,4-phenylene or trans 1,3-dioxane-2,5-diyl group, ring $G_2$ represents a trans-1,4-cyclohexylene, or 1,4-phenylene group, and c and d represent independently 0 or 1.

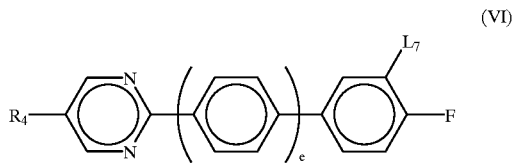
(VI)

In the formula (VI), $R_4$ represents an alkyl group having 1 to 10 carbon atoms, $L_7$ represents H or F, and e represents 0 or 1.

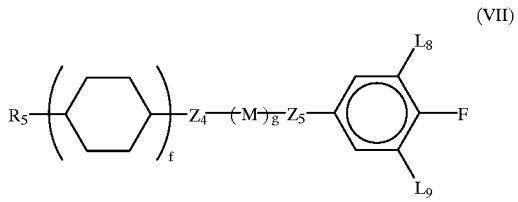
(VII)

In the formula (VII), $R_5$ represents an alkyl group having 1 to 10 carbon atoms, M represents trans-1,4-cyclohexylene or 1,4-phenyelne group, $L_8$ and $L_9$ represent independently H or F, $Z_4$ represents —CO—O— or a covalent bond, $Z_5$ represents —CO—O— or —C≡C—, and f and g represent independently 0 or 1.

$R_6$—W—$Z_6$—Q—$R_7$ (VIII)

In the formula (VIII), $R_6$ and $R_7$ represent independently an alkyl groups having 1 to 10 carbon atoms, an alkoxy group having 1 to 10 carbon atoms or an alkoxymethyl group having 1 to 10 carbon atoms, W represents a trans-1,4-cyclohexylene, 1,4-phenylene or 1,3-pyrimidine-2,5-diyl group, Q represents a trans-1,4-cyclohexylene or 1,4-phenylene, and $Z_6$ represents —C≡C—, —CO—O—, —$CH_2CH_2$— or a covalent bond.

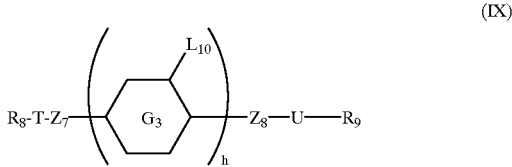
(IX)

In the formula (IX), $R_8$ represents an alkyl group having 1 to 10 carbon atoms or an alkoxy group having 1 to 10 carbon atoms. $R_9$ represents an alkyl group having 1 to 10 carbon atoms. Any methylene group (—$CH_2$—) in $R_9$ may be replaced by one or more oxygen atoms (—O—), provided that two or more successive methylene groups are not replaced by oxygen atoms. T represents a trans-1,4-cyclohexylene group or 1,3-pyrimidine-2,5-diyl group, ring $G_3$ and U represent independently a trans-1,4-cyclohexylene group or a 1,4-phenylene group, $Z_7$ represents —$CH_2CH_2$—, —CH=CH—, —CO—O— or a covalent bond, $Z_8$ represents —C≡C—, —CO—O—, or a covalent bond, h represents 0 or 1, and $L_{10}$ represents H or F.

The present invention further provides a liquid crystal composition which comprises at least one compound of the formula (I), at least one compound selected from the group consisting of the compounds of the formulas (II), (III) and (IV), and at least one compound selected from the group consisting of the compounds of the formulas (V), (VI), (VII), (VIII) and (IX).

The present invention further provides a liquid crystal display element comprising the liquid crystal composition mentioned above.

BEST MODE FOR CARRYING OUT THE INVENTION

The compounds of the formula (I) of the present invention are carboxylate derivatives characterized in that they exhibit large dielectric anisotropy because they have halogen-substituted alkyl groups, halogen-substituted alkoxy groups, cyano groups or halogen atoms on the phenyl group at the one terminal of molecule thereof, they show excellent heat-stability, they exhibit low threshold voltage when used as a display element, and further they have favorable temperature-dependency of threshold voltage. Furthermore, the compounds of the present invention have high miscibility with other known liquid crystal compounds at low temperature and they are physically and chemically stable under the conditions which are usually employed. Accordingly, when the compound of the present invention is used as a component of a liquid crystal composition, a novel liquid crystal composition having favorable properties can be provided.

The compounds represented by formula (I) according to the present invention fall into the following formulas (I-1) to (I-8).

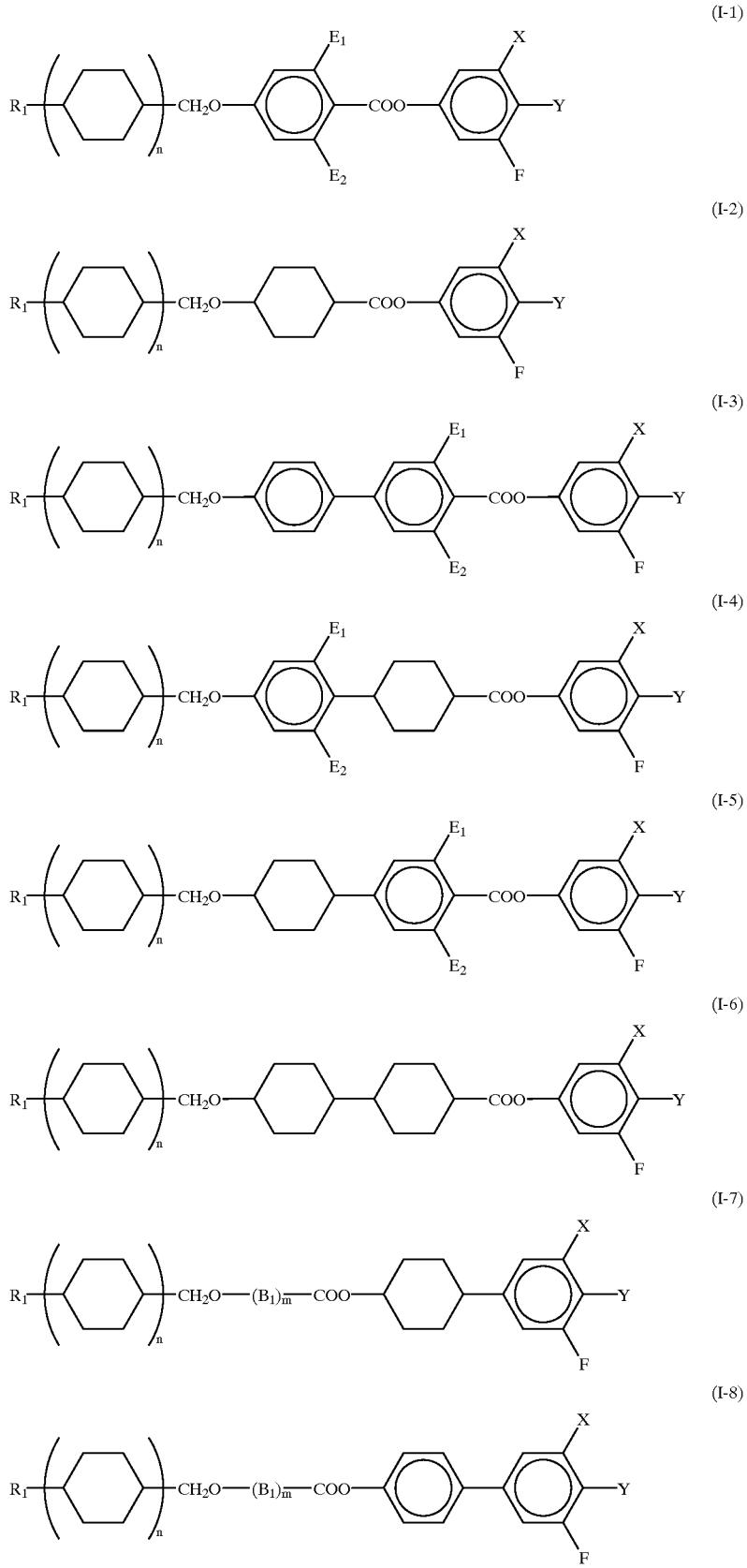

wherein $R_1$, $B_1$, m, n, X, Y are defined as above, and $E_1$ and $E_2$ represent independently a halogen atom or a hydrogen atom.

Among these compounds, particularly preferred are the compounds represented by the formulas (I-1) and (I-2) in attaining the object of the present invention. Further, the formula (I-1) falls into the following formulas (I-1a) to (I-1i) and the formula (I-2) falls into the following formulas (I-2a) to (I-2c).

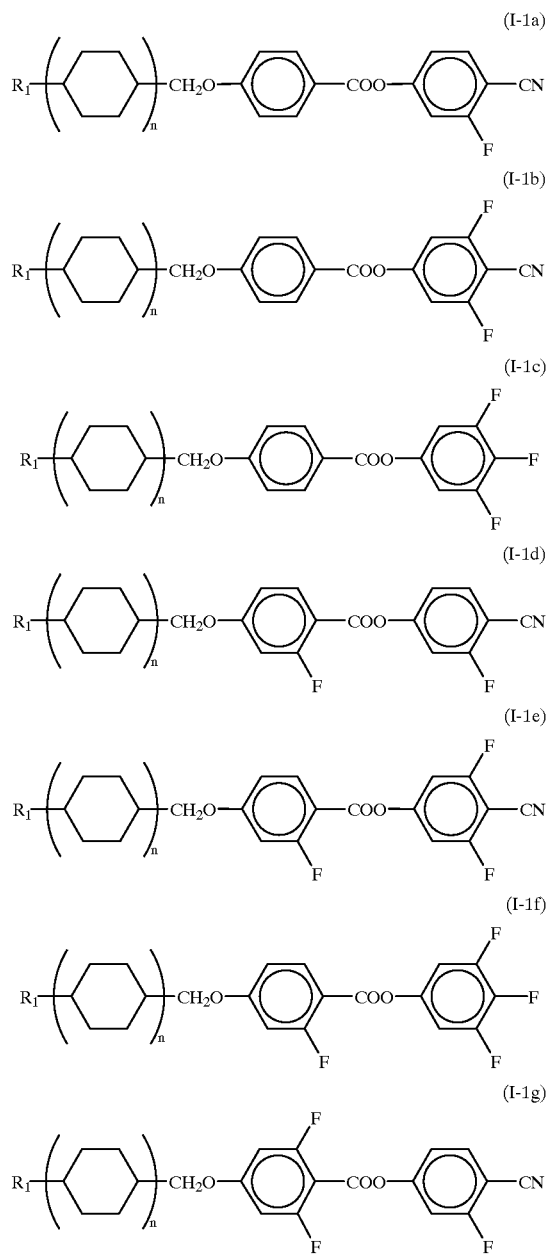

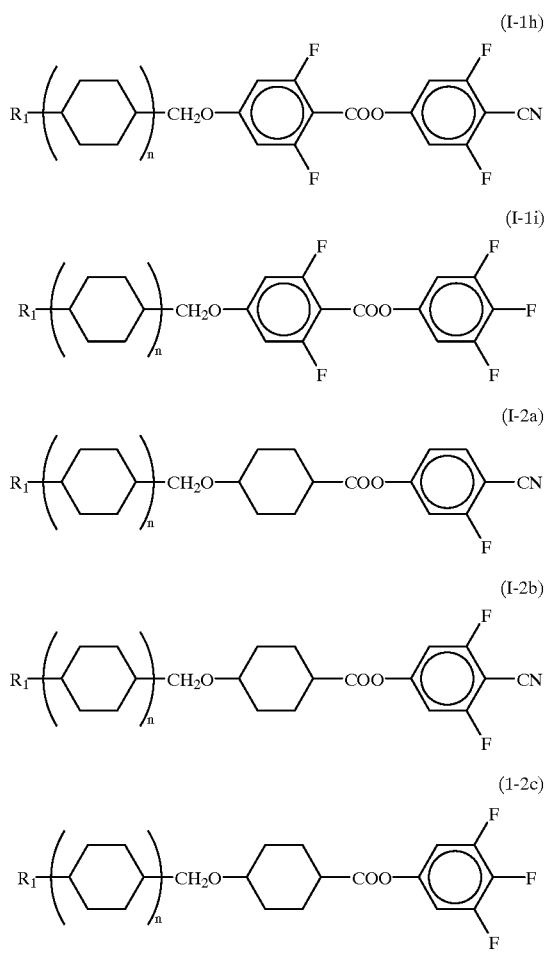

wherein $R_1$ and n are defined as above.

In the compound of the present invention, when Y represents a halogen-substituted alkyl group having 1 to 3 carbon atoms or a halogen-substituted alkoxy group having 1 to 3 carbon atoms, a preferred halogen is fluorine or chlorine, and fluorine is particularly preferred.

The most preferred groups include specifically $CF_3$, $CH_2CF_3$, $C_2F_5$, $OCF_3$, $OCF_2H$, $OCF_2CF_2H$, $OCF_2CF_3$, $OCFHCF_3$, $OCH_2CF_3$, $OCF_2CH_3$, $OCH_2CF_2H$, $OCF_2CFHCF_3$ and the like.

The compound represented by the general formula (I) according to the present invention may be prepared, for example, by the following steps.

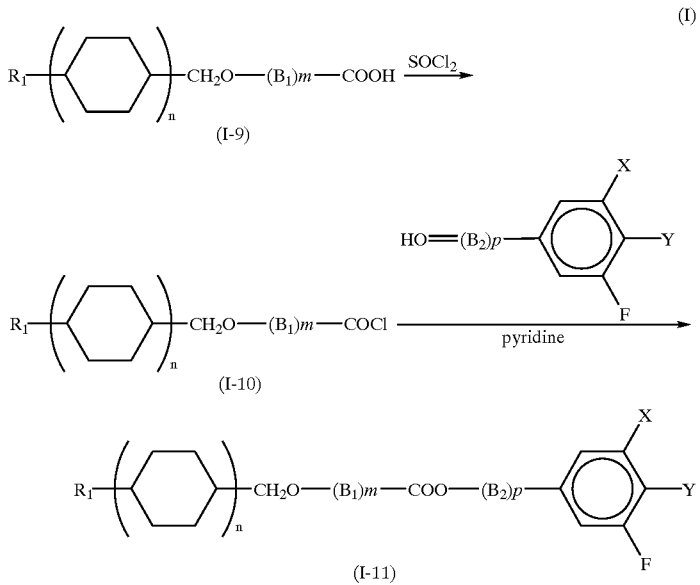

wherein $R_1$, n, m, p, $B_1$, $B_2$, X and Y are defined as above.

A carboxylic acid derivative (I-9) is chlorinated with thionyl chloride, and an acid chloride derivative (I-10) is synthesized. Further, the acid chloride derivative (I-10) is reacted with phenol derivative (I-11) in the presence of pyridine to give the liquid crystal compound represented by the general formula (I).

Incidentally, the starting materials, a carboxylic acid derivative represented by the formula (I-9) and a phenol derivative represented by the formula (I-11) may be prepared, for example, by the following method.

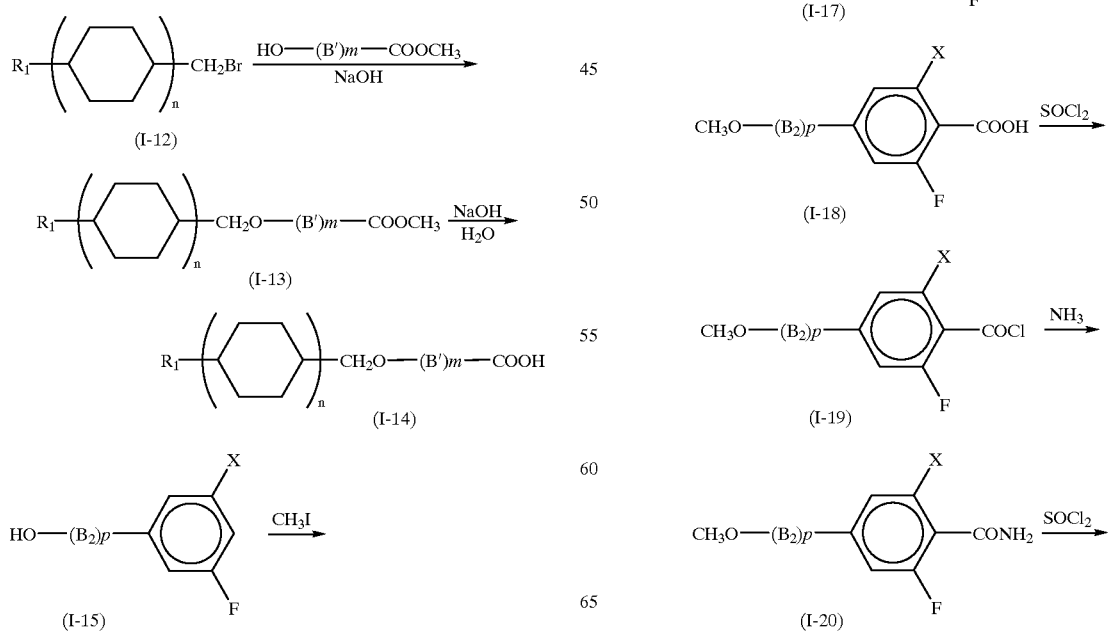

-continued

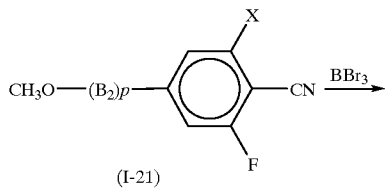

(I-21)

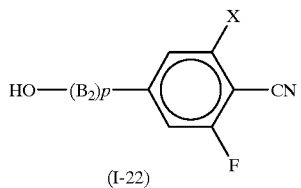

(I-22)

wherein $R_1$, $B_1$, n, m, p, X are defined as above, B' represents 1,4-phenylene group wherein one or more hydrogen atoms on six-membered ring may be substituted by halogen atoms.

A cyclohexylmethylbromide derivative (I-12) is reacted with a phenol derivative to give an ether derivative (I-13), and then the ether derivative (I-13) is hydrolyzed in the presence of an alkali to give a carboxylic acid derivative (I-14). The formula (I-14) is encompassed by a carboxylic acid derivative represented by the formula (I-9).

An anisol derivative (I-16) is synthesized from a phenol derivative (I-15), and then via a phenyl lithium derivative (I-17), a carboxylic acid derivative (I-18) is obtained. Then, via an acid chloride derivative (I-19) and an acid amide derivative (I-20), benzonitrile derivative (I-21) is synthesized, and further a cyanophenol derivative (I-22) is obtained.

The formula (I-22) is encompassed by a phenol derivative represented by formula (I-11).

The liquid crystal composition of the present invention may be the one which comprises at least one of the compound represented by the general formula (I) (hereinafter also referred to as "a first component") and more preferred is the one which comprises additionally as a second component at least one compound selected from the group consisting of the compounds of the formulas (II), (III) and (IV) (hereinafter also referred to as "a second component A") and/or at least one compound selected from the group consisting of the compounds of the formulas (V), (VI), (VII), (VIII) and (IX) (hereinafter also referred to as "a second component B").

Further, the composition may contain one or more known compounds, as a third component, to adjust threshold voltage, liquid crystal phase temperature range, optical anisotropy, dielectric anisotropy, and viscosity.

Among the second component A, preferred examples of the formula (II) are the following (II-1) to (II-15), preferred examples of the formula (III) are the following (III-1) to (III-48), and preferred examples of the formula (IV) are (IV-1) to (IV-39).

II-1

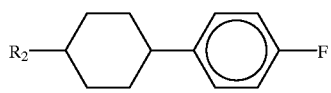

II-2

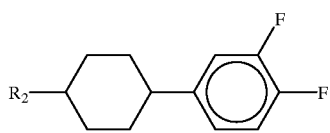

II-3

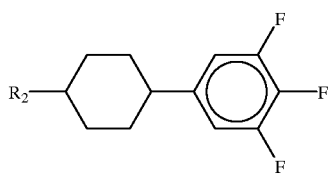

II-4

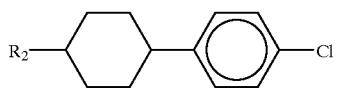

II-5

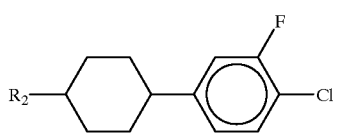

II-6

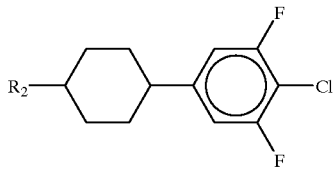

II-7

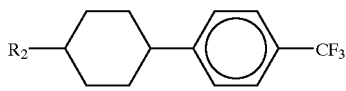

II-8

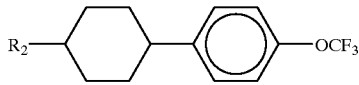

II-9

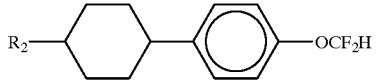

II-10

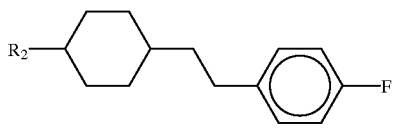

II-11

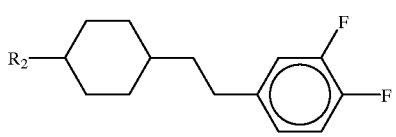

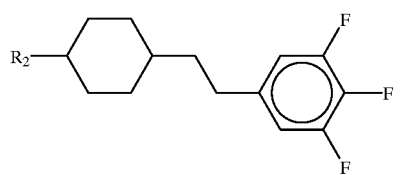
II-12
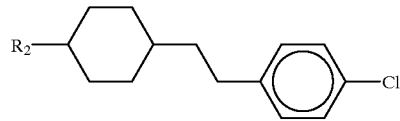
II-13
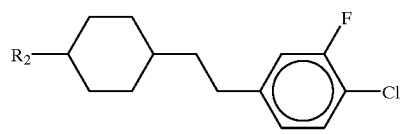
II-14
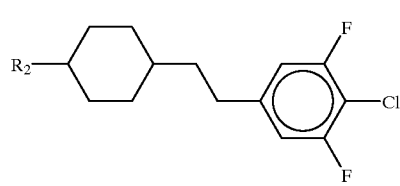
II-15
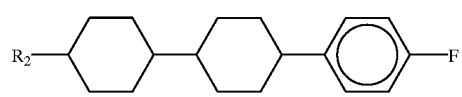
III-1
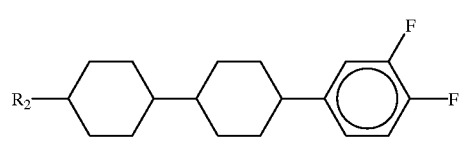
III-2
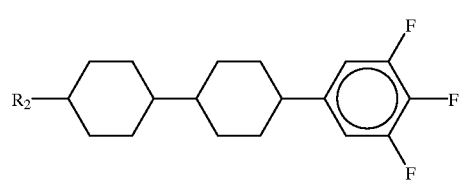
III-3
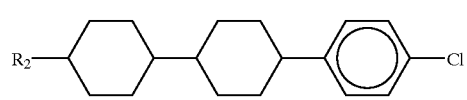
III-4
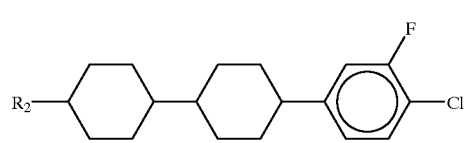
III-5
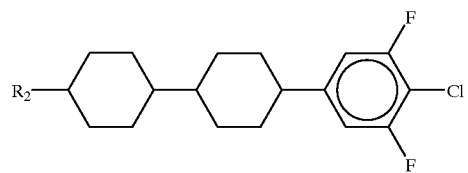
III-6
III-7
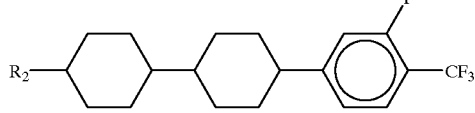
III-8
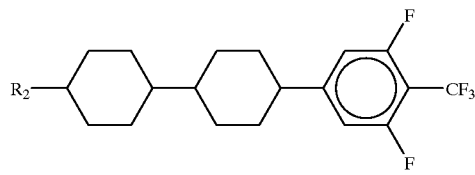
III-9
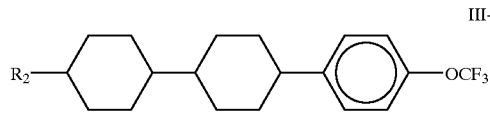
III-10
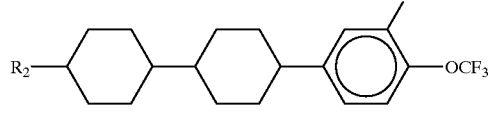
III-11
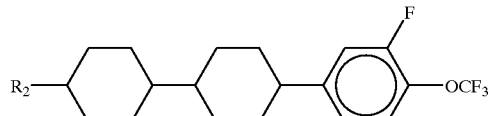
III-12
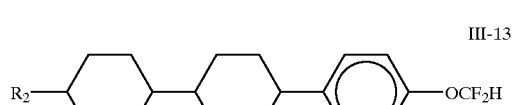
III-13
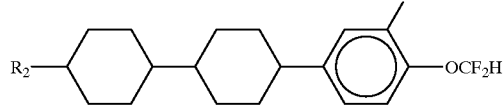
III-13
III-14
III-15
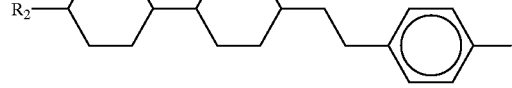
III-16

-continued
III-17
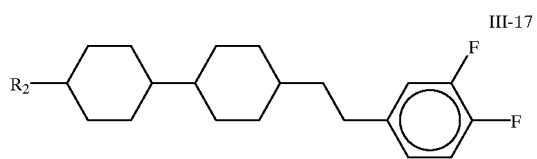
III-18
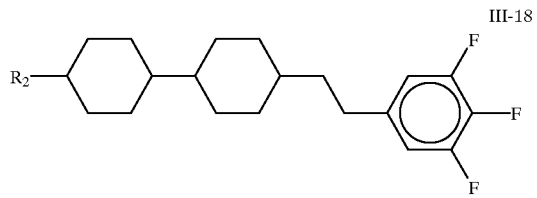
III-19
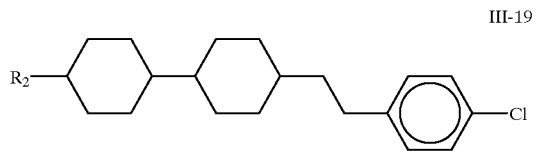
III-20
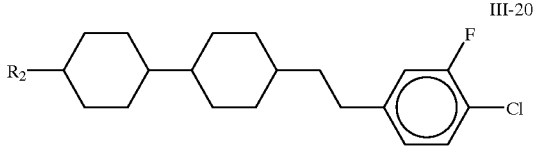
III-21
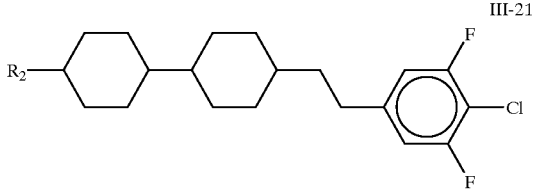
III-22
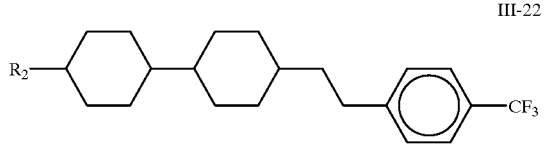
III-23
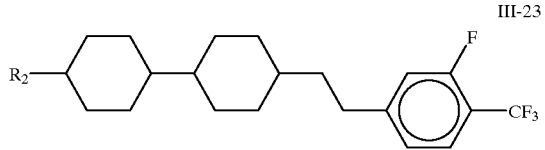
III-24
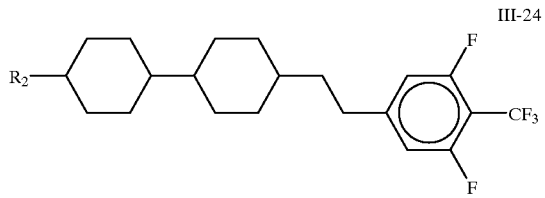
III-25
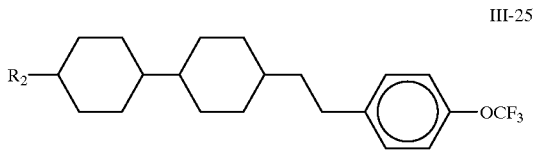
-continued
III-26
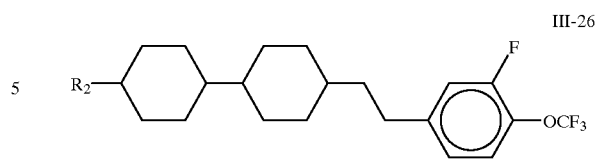
III-27
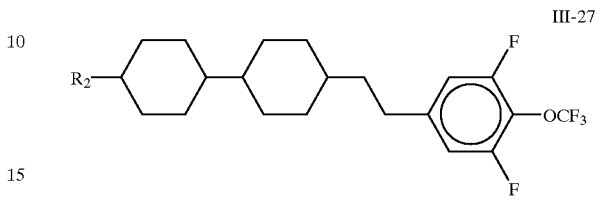
III-28
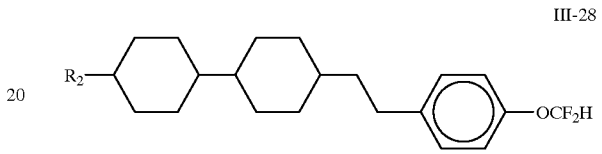
III-29
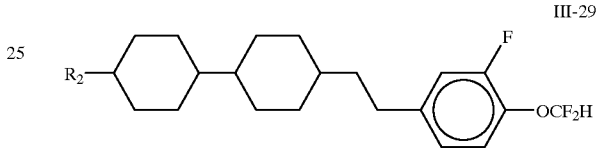
III-30
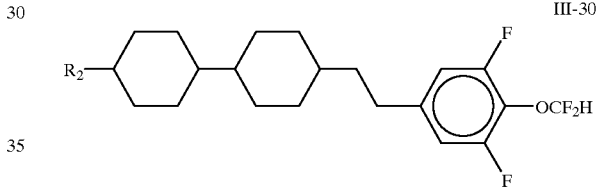
III-31
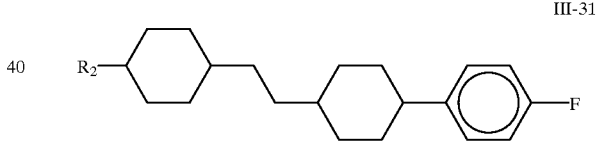
III-32
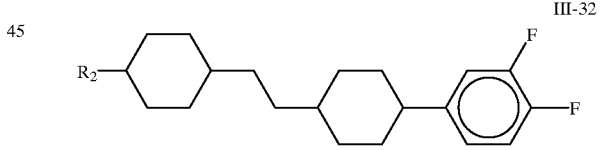
III-33
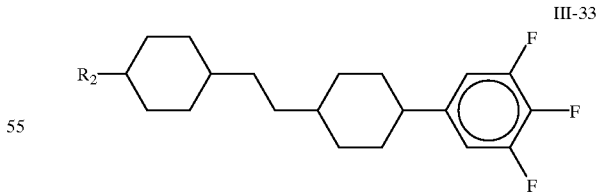
III-34
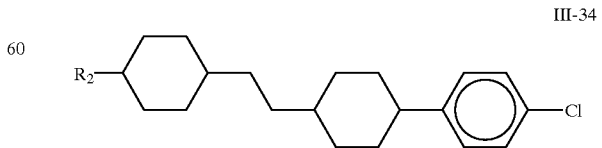

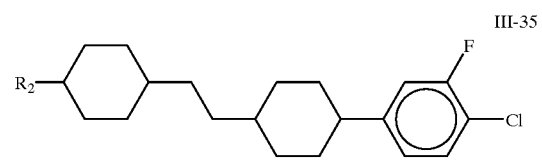
III-35
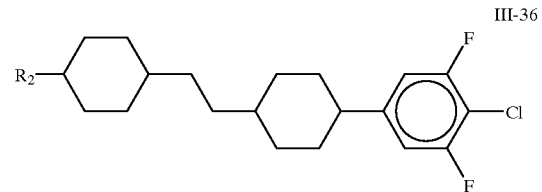
III-36
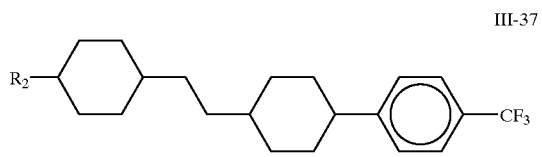
III-37
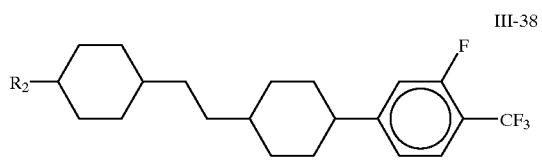
III-38
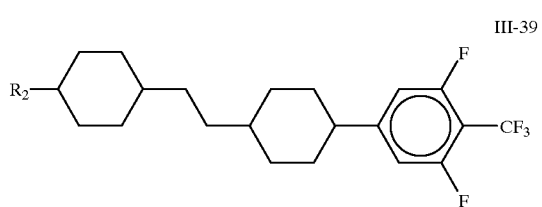
III-39
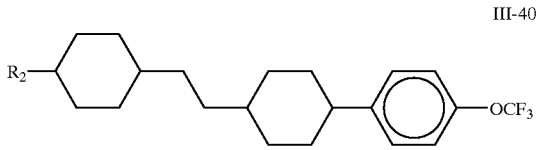
III-40
III-41
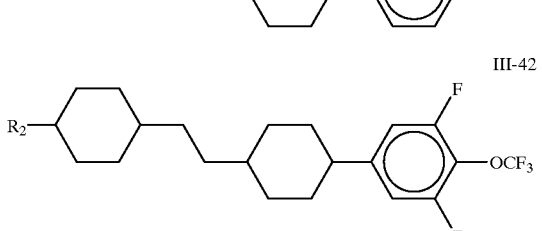
III-42
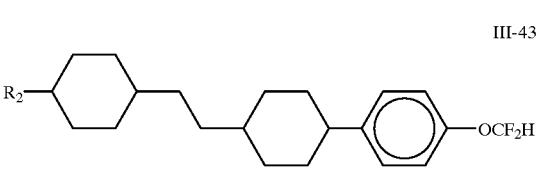
III-43
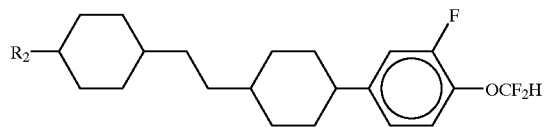
III-44
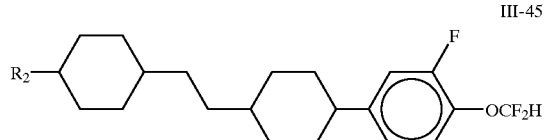
III-45
III-46
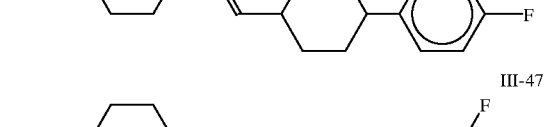
III-47
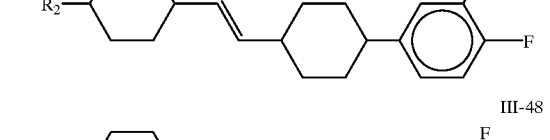
III-48
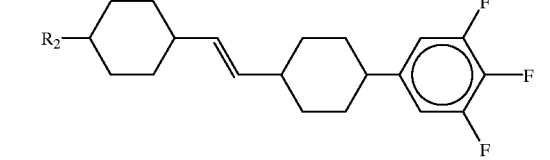
IV-1
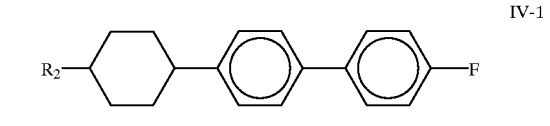
IV-2
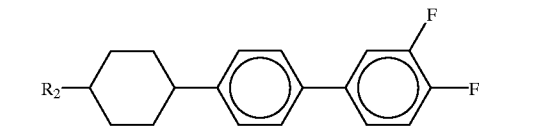
IV-3
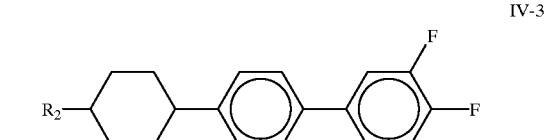
IV-4
IV-5

-continued
IV-6
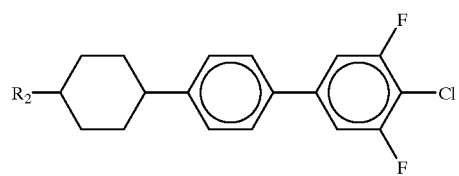
IV-7
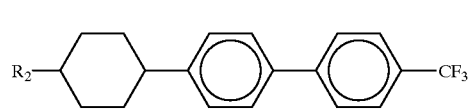
IV-8
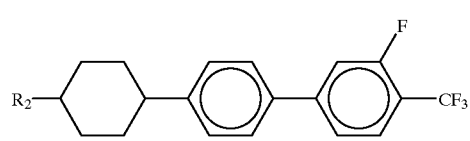
IV-9
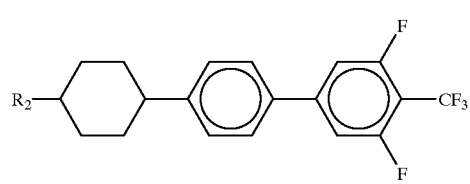
IV-10
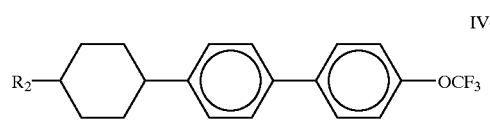
IV-11
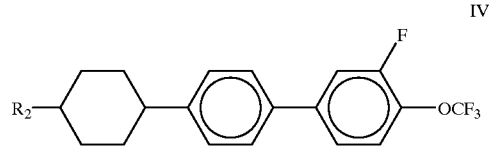
IV-12
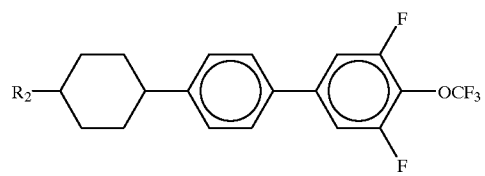
IV-13
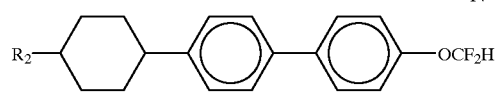
IV-14
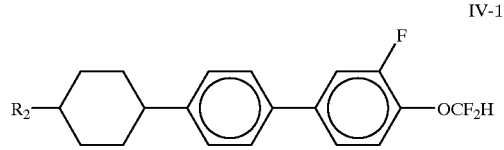
IV-15
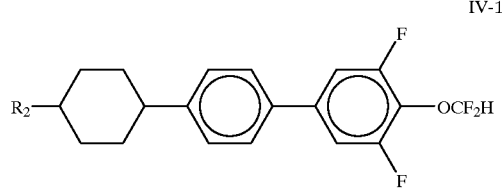
-continued
IV-16
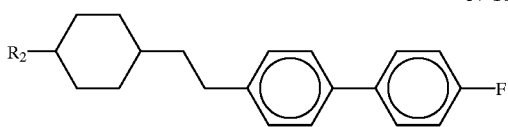
IV-17
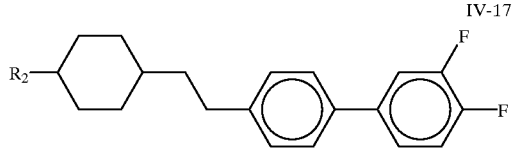
IV-18
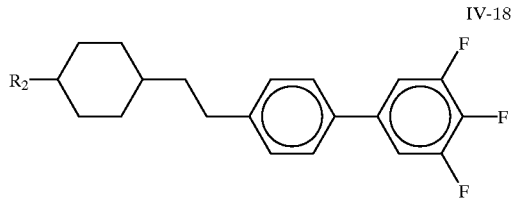
IV-19
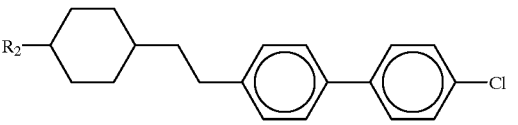
IV-20
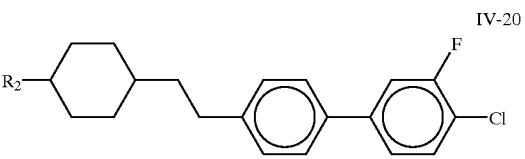
IV-21
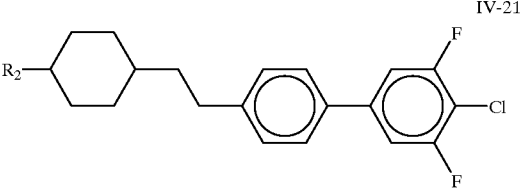
IV-22
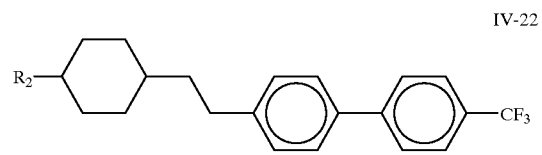
IV-23
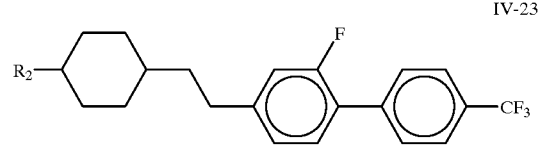
IV-24
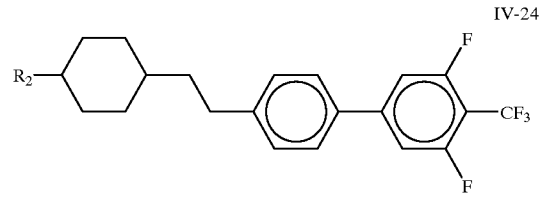

-continued

IV-25
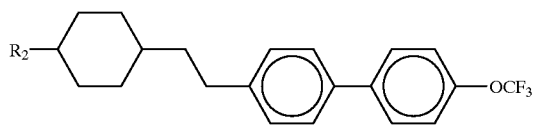

IV-26
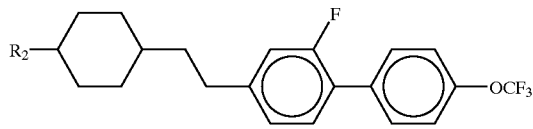

IV-27
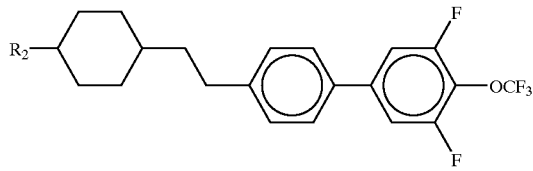

IV-28
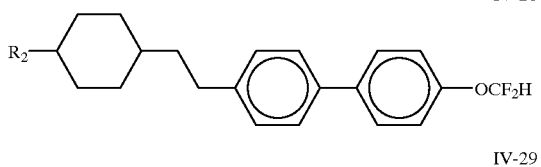

IV-29
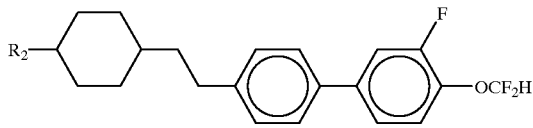

IV-30
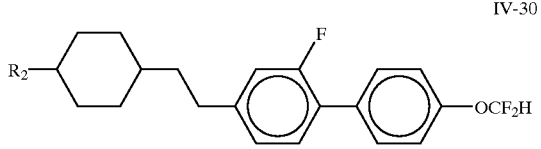

IV-31
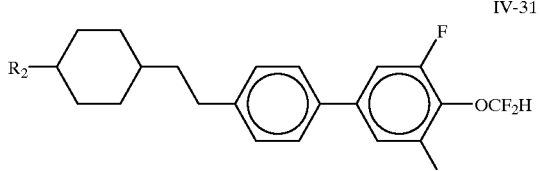

IV-32
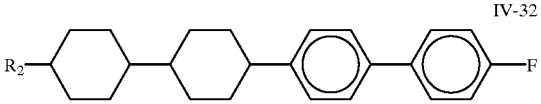

IV-33
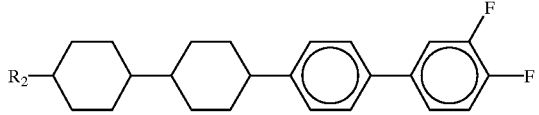

IV-34
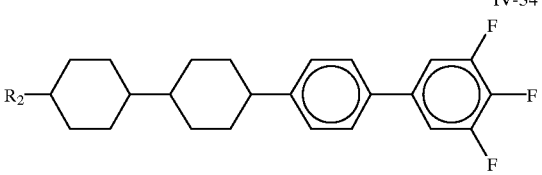

-continued

IV-35
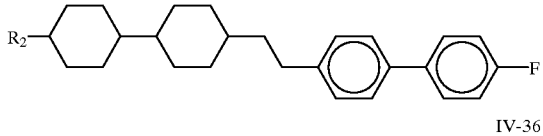

IV-36
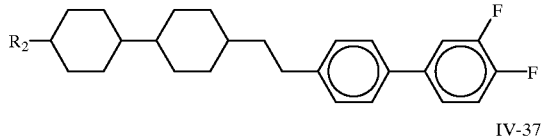

IV-37
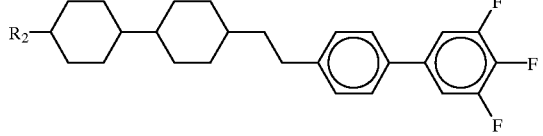

IV-38
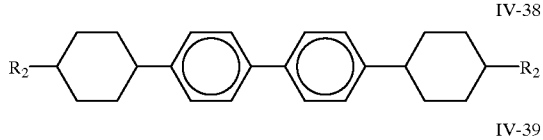

IV-39
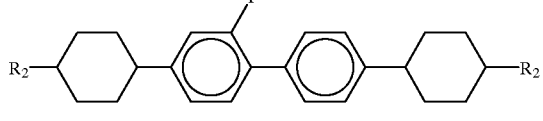

The compounds represented by the formulas (II) to (IV) show positive dielectric anisotropy and have very good heat stability. Thus these compounds are essential to prepare a liquid crystal composition suitable for AM-LCD (TFT) which requires a large voltage holding ratio and high reliability.

The amount of the compounds of the formulas (II) to (IV) is suitably 1 to 99% by weight, preferably 10 to 97% by weight, and more preferably 40 to 95% by weight based on the total weight of the liquid crystal composition.

Among the second component B, preferred examples of the compounds of the formulas (V), (VI) and (VII) are (V-1) to (V-27), (VI-1) to (VI-3) and (VII-1) to (VII-13), respectively. In the formulas, R' represents an alkylene group.

V-1
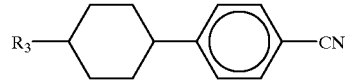

V-2
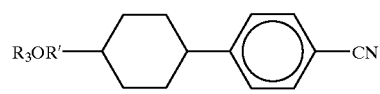

V-3
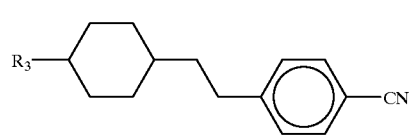

V-4
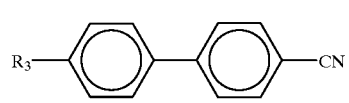

V-5 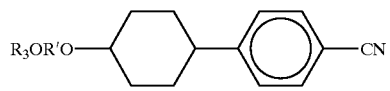
V-6 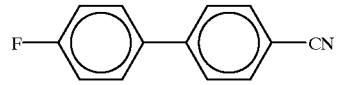
V-7 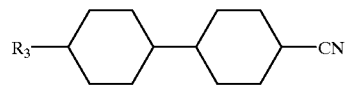
V-8 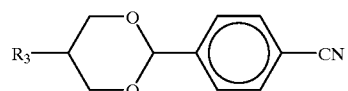
V-9 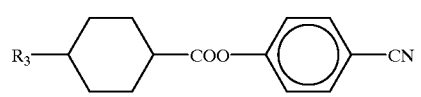
V-10 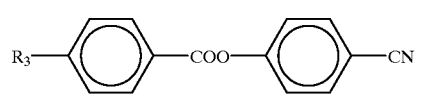
V-11 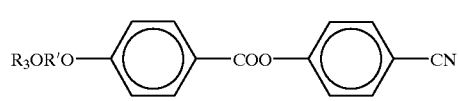
V-12 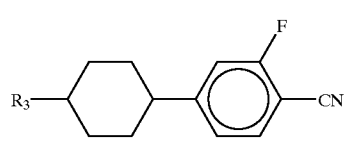
V-13 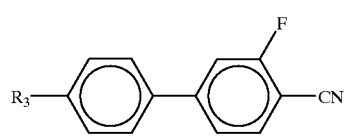
V-14 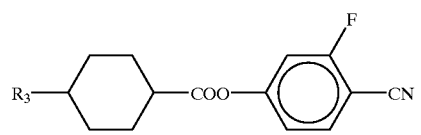
V-15 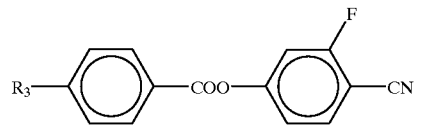
V-16 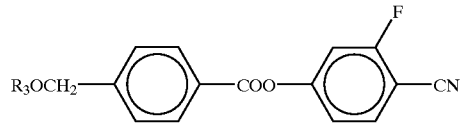
V-17 
V-18 
V-19 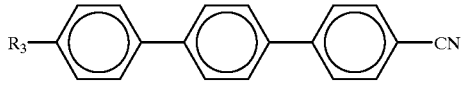
V-20 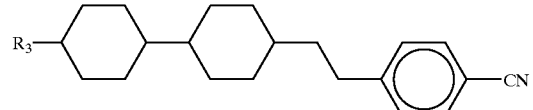
V-21 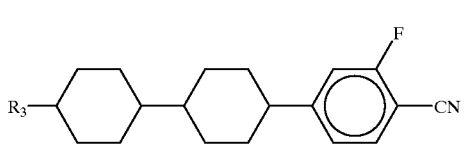
V-22 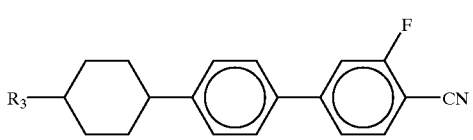
V-23 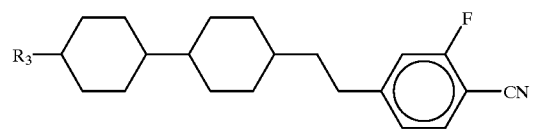
V-24 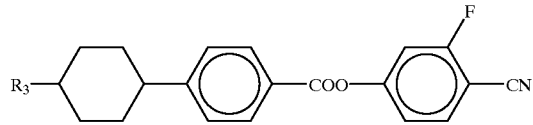
V-25 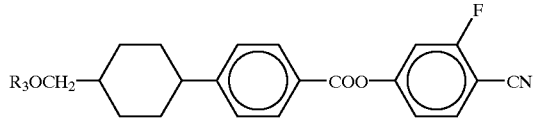
V-26 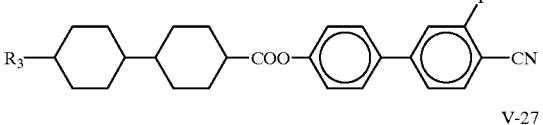
V-27 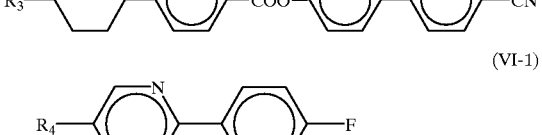
(VI-1)

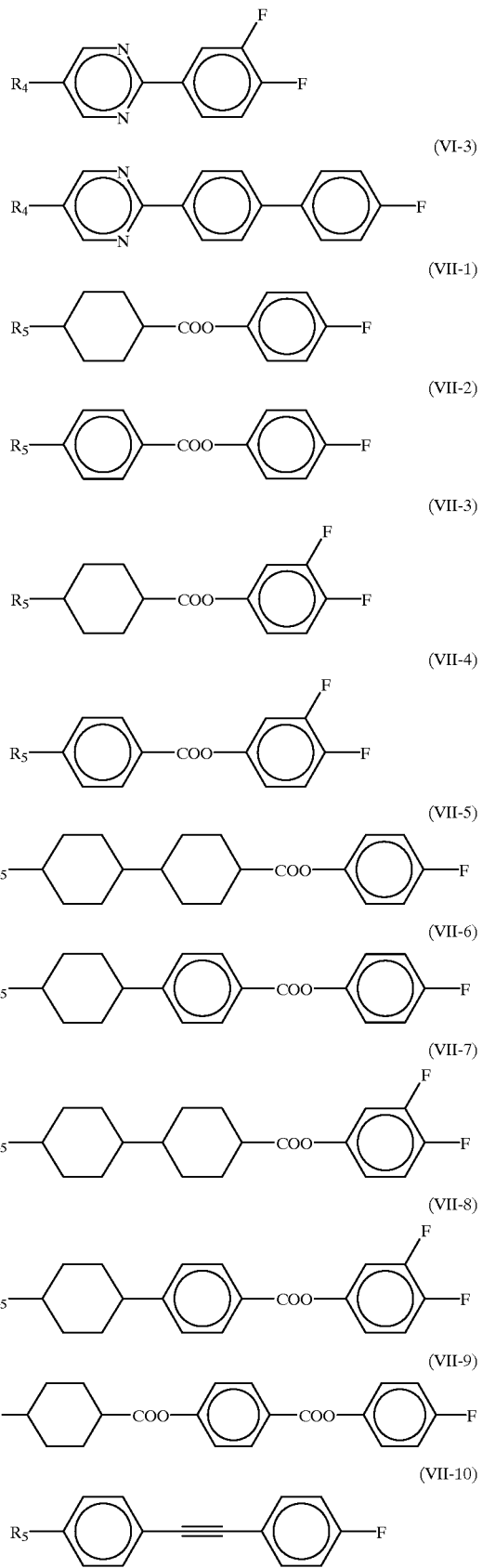
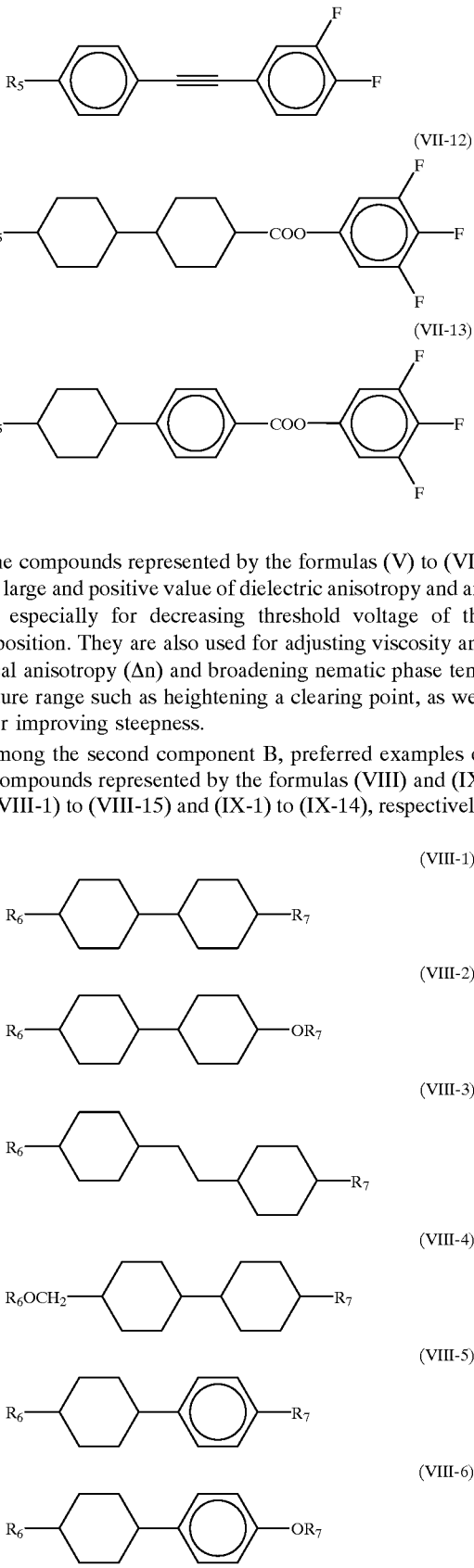

The compounds represented by the formulas (V) to (VII) have large and positive value of dielectric anisotropy and are used especially for decreasing threshold voltage of the composition. They are also used for adjusting viscosity and optical anisotropy (Δn) and broadening nematic phase temperature range such as heightening a clearing point, as well as for improving steepness.

Among the second component B, preferred examples of the compounds represented by the formulas (VIII) and (IX) are (VIII-1) to (VIII-15) and (IX-1) to (IX-14), respectively.

(VIII-7)
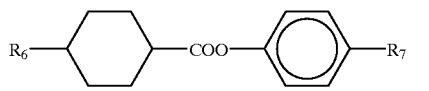

(VIII-8)
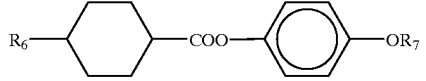

(VIII-9)
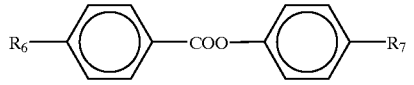

(VIII-10)
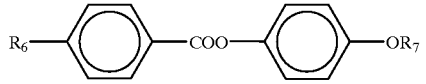

(VIII-11)
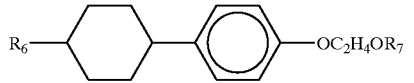

(VIII-12)
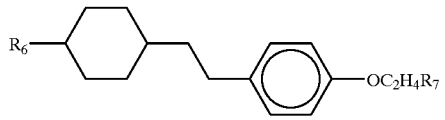

(VIII-13)
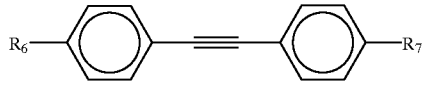

(VIII-14)
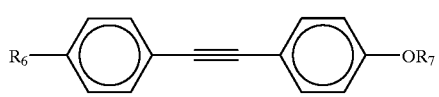

(VIII-15)
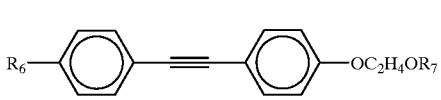

(IX-1)
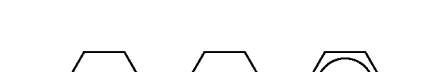

(IX-2)
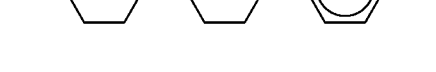

(IX-3)
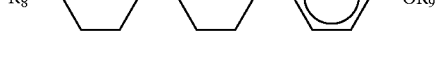

(IX-4)

(IX-5)
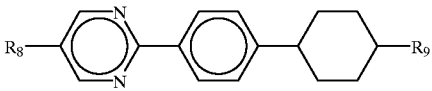

(IX-6)
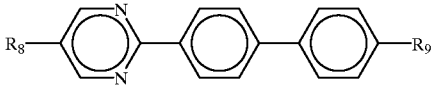

(IX-7)
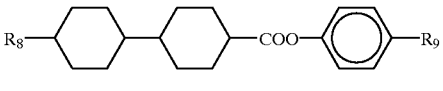

(IX-8)
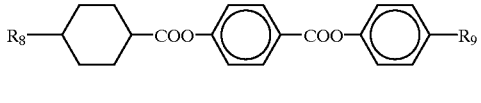

(IX-9)

(IX-10)
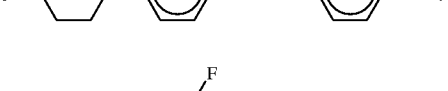

(IX-11)

(IX-12)
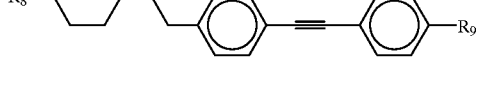

(IX-13)
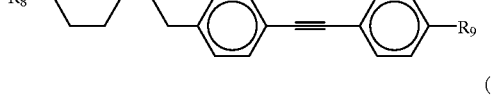

(IX-14)
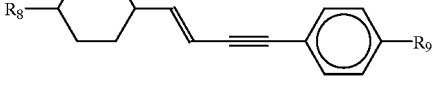

The compounds represented by the formulas (VIII) and (IX) have negative or weakly positive dielectric anisotropy. The compounds of the formula (VIII) are used for lowering viscosity or adjusting optical anisotropy ($\Delta n$), and the compounds of the formula (IX) are used for broadening temperature range of nematic phase such as heightening a clearing point and for adjusting optical anisotropy ($\Delta n$) in the composition.

The compounds of the formulas (V) to (IX) are essential for preparing a liquid crystal composition for STN display mode or TN display mode. The amount of the compounds used for the preparation of a liquid crystal composition for STN display mode or TN display mode is suitably 1 to 99% by weight, preferably 10 to 97% by weight, more preferably 40 to 95% by weight based on the total weight of the liquid crystal composition.

As mentioned above, a liquid crystal composition for TFT may be prepared from the first component and the second component A, and may also contain additionally the second component B. A liquid crystal composition for STN display mode or TN display mode may be prepared from the first component and the second component B, and may also contain additionally the second component A.

The liquid crystal composition of the present invention preferably includes at least one compound of the formula (I) in the amount of 0.1 to 99% by weight to exhibit excellent characteristics. The liquid crystal composition of the present invention can be prepared by conventional methods. Generally, they may be prepared by dissolving various components at an elevated temperature. Further, the liquid crystal composition of the present invention may be improved and optimized by the addition of an additive suitable for an intended purpose. Such additives are well known by a person skilled in the art and described in detail in literature. Typically, a chiral dopant is added to induce spiral structure of the liquid crystal so as to adjust a desired degree of twist angle and to avoid reverse twist.

The liquid crystal composition of the present invention can be used for guest-host (GH) mode if a dichroic dye such as merocyanine, styryl, azo, azomethine, azoxy, quinophthalone, anthraquinone and tetrazine dyes is added thereto. Further, the composition of the present invention can be used as a liquid crystal composition for polymer dispersed type liquid crystal display element (PDLCD) represented by NCAP (Nematic Curvilinear Aligned Phases) which is obtained by microencapsulating nematic liquid crystals, and for polymer network liquid crystal display element (PNLCD) which is obtained by forming a three dimensional polymer network in liquid crystals. In addition, the composition of the present invention can also be used as a liquid crystal composition for electrically controlled birefringence (ECB) mode and dynamic scattering (DS) mode.

EXAMPLES

The following examples explain in detail the present invention and the examples are not intended to limit the scope of the present invention.

In the examples, CN means a transition temperature (° C.) between a crystal phase and a nematic phase, NI means a transition temperature (° C.) between a nematic phase and an isotropic phase, and CI means a transition temperature (° C.) between a crystal phase and an isotropic phase.

Example 1

3-Fluoro-4-cyanophenyl 4-(trans-4-ethylcyclohexylmethoxy)benzoate (Preparation of compound (1) represented by the formula (I) wherein $B_1$ is 1,4-phenylene, Y is a cyano group, X is a hydrogen atom, $R_1$ is an ethyl group, n is 1, m is 1, and p is 0)

1) A solution of potassium hydroxide (56.1 g) dissolved in 30 ml of water, and methyl 4-hydroxybenzoate (152 g) were suspended in 1500 ml of ethyleneglycolmonoethylether. To this mixture was dropped trans-4-ethylcyclohexylmethylbromide (200 g), and then the mixture formed was stirred under reflux for 4 hours. After cooling to room temperature, a solution of sodium hydroxide (80 g) dissolved in water (400 ml) was added with stirring and was refluxed for 2 hours. After the reaction was completed, the mixture was cooled, added with diluted hydrochloric acid (1 liter), and extracted with toluene (5 liters). The organic layer separated was washed with water, dried over anhydrous magnesium sulfate, and then the solvent was distilled off under reduced pressure to obtain 4-(trans-4-ethylcyclohexylmethoxy)benzoic acid (147 g).

2) To toluene (300 ml) was suspended 4-(trans-4-ethylcyclohexylmethoxy)benzoic acid (147 g), and then thionyl chloride (68.1 g) was added with stirring and refluxed for 2 hours. After cooling to room temperature, a solution of 3-fluoro-4-cyanophenol (78.6 g) dissolved in pyridine (45.3 g) was added with stirring and refluxed for 2 hours. After the reaction was completed, the mixture was added with diluted hydrochloric acid (700 ml) and was extracted with toluene (1 liters). The organic layer separated was washed with water, dried over anhydrous magnesium sulfate, and then the solvent was distilled off under reduced pressure to give cinnamon-colored oil. The oil was recrystallized from ethyl acetate to give the above-captioned compound (88 g). CN: 95.1° C., NI: 151.0° C.

In the similar manner to those of Example 1, the following compounds (2) to (108), (228) and (229) can be prepared.

(2) 3-Fluoro-4-cyanophenyl 4-(trans-4-methylcyclohexylmethoxy)benzoate
(3) 3-Fluoro-4-cyanophenyl 4-(trans-4-propylcyclohexylmethoxy)benzoate
(4) 3-Fluoro-4-cyanophenyl 4-(trans-4-butylcyclohexylmethoxy)benzoate
(5) 3-Fluoro-4-cyanophenyl 4-(trans-4-pentylcyclohexylmethoxy)benzoate
(6) 3-Fluoro-4-cyanophenyl 4-(trans-4-hexylcyclohexylmethoxy)benzoate
(7) 3-Fluoro-4-cyanophenyl 4-(trans-4-heptylcyclohexylmethoxy)benzoate
(8) 3-Fluoro-4-cyanophenyl 4-(trans-4-octylcyclohexylmethoxy)benzoate
(9) 3-Fluoro-4-cyanophenyl 4-(trans-4-nonylcyclohexylmethoxy)benzoate
(10) 3-Fluoro-4-cyanophenyl 4-(trans-4-decylcyclohexylmethoxy)benzoate
(11) 3-Fluoro-4-cyanophenyl 4-(trans-4-propoxycyclohexylmethoxy)benzoate
(12) 3-Fluoro-4-cyanophenyl 4-(trans-4-butoxycyclohexylmethoxy)benzoate
(13) 3-Fluoro-4-cyanophenyl 4-(trans-4-pentyloxycyclohexylmethoxy) benzoate
(14) 3-Fluoro-4-cyanophenyl 4-(trans-4-hexyloxycyclohexylmethoxy) benzoate
(15) 3-Fluoro-4-cyanophenyl 4-(trans-4-(trans-4-ethylcyclohexyl) cyclohexylmethoxy)benzoate
(16) 3-Fluoro-4-cyanophenyl 4-(trans-4-(trans-4-propylcyclohexyl) cyclohexylmethoxy)benzoate
(17) 3-Fluoro-4-cyanophenyl 4-(trans-4-(trans-4-butylcyclohexyl) cyclohexylmethoxy)benzoate
(18) 3-Fluoro-4-cyanophenyl 4-(trans-4-(trans-4-pentylcyclohexyl) cyclohexylmethoxy)benzoate
(19) 3,5-Difluoro-4-cyanophenyl 4-(trans-4-methylcyclohexylmethoxy) benzoate
(20) 3,5-Difluoro-4-cyanophenyl 4-(trans-4-ethylcyclohexylmethoxy) benzoate
(21) 3,5-Difluoro-4-cyanophenyl 4-(trans-4-propylcyclohexylmethoxy) benzoate
(22) 3,5-Difluoro-4-cyanophenyl 4-(trans-4-butylcyclohexylmethoxy) benzoate
(23) 3,5-Difluoro-4-cyanophenyl 4-(trans-4-pentylcyclohexylmethoxy) benzoate
(24) 3,5-Difluoro-4-cyanophenyl 4-(trans-4-hexylcyclohexylmethoxy) benzoate
(25) 3,5-Difluoro-4-cyanophenyl 4-(trans-4-heptylcyclohexylmethoxy) benzoate
(26) 3,5-Difluoro-4-cyanophenyl 4-(trans-4-octylcyclohexylmethoxy) benzoate
(27) 3,5-Difluoro-4-cyanophenyl 4-(trans-4-nonylcyclohexylmethoxy) benzoate

(28) 3,5-Difluoro-4-cyanophenyl 4-(trans-4-decylcyclohexylmethoxy) benzoate
(29) 3,5-Difluoro-4-cyanophenyl 4-(trans-4-propoxycyclohexylmethoxy) benzoate
(30) 3,5-Difluoro-4-cyanophenyl 4-(trans-4-butoxycyclohexylmethoxy) benzoate
(31) 3,5-Difluoro-4-cyanophenyl 4-(trans-4-pentyloxycyclohexylmethoxy) benzoate
(32) 3,5-Difluoro-4-cyanophenyl 4-(trans-4-hexyloxycyclohexylmethoxy) benzoate
(33) 3,5-Difluoro-4-cyanophenyl 4-(trans-4-(trans-4-ethylcyclohexyl) cyclohexylmethoxy)benzoate
(34) 3,5-Difluoro-4-cyanophenyl 4-(trans-4-(trans-4-propylcyclohexyl) cyclohexylmethoxy)benzoate
(35) 3,5-Difluoro-4-cyanophenyl 4-(trans-4-(trans-4-butylcyclohexyl) cyclohexylmethoxy)benzoate
(36) 3,5-Difluoro-4-cyanophenyl 4-(trans-4-(trans-4-pentylcyclohexyl) cyclohexylmethoxy)benzoate
(37) 3,4,5-Trifluorophenyl 4-(trans-4-methylcyclohexylmethoxy)benzoate
(38) 3,4,5-Trifluorophenyl 4-(trans-4-ethylcyclohexylmethoxy)benzoate
(39) 3,4,5-Trifluorophenyl 4-(trans-4-propylcyclohexylmethoxy)benzoate
(40) 3,4,5-Trifluorophenyl 4-(trans-4-butylcyclohexylmethoxy)benzoate
(41) 3,4,5-Trifluorophenyl 4-(trans-4-pentylcyclohexylmethoxy)benzoate
(42) 3,4,5-Trifluorophenyl 4-(trans-4-hexylcyclohexylmethoxy)benzoate
(43) 3,4,5-Trifluorophenyl 4-(trans-4-heptylcyclohexylmethoxy)benzoate
(44) 3,4,5-Trifluorophenyl 4-(trans-4-octylcyclohexylmethoxy)benzoate
(45) 3,4,5-Trifluorophenyl 4-(trans-4-nonylcyclohexylmethoxy)benzoate
(46) 3,4,5-Trifluorophenyl 4-(trans-4-decylcyclohexylmethoxy)benzoate
(47) 3,4,5-Trifluorophenyl 4-(trans-4-propoxycyclohexylmethoxy)benzoate
(48) 3,4,5-Trifluorophenyl 4-(trans-4-butoxycyclohexylmethoxy)benzoate
(49) 3,4,5-Trifluorophenyl 4-(trans-4-pentylcyclohexylmethoxy)benzoate
(50) 3,4,5-Trifluorophenyl 4-(trans-4-hexyloxycyclohexylmethoxy)benzoate
(51) 3,4,5-Trifluorophenyl 4-(trans-4-(trans-4-ethylcyclohexyl) cyclohexylmethoxy)benzoate
(52) 3,4,5-Trifluorophenyl 4-(trans-4-(trans-4-propylcyclohexyl) cyclohexylmethoxy)benzoate
(53) 3,4,5-Trifluorophenyl 4-(trans-4-(trans-4-butylcyclohexyl) cyclohexylmethoxy)benzoate
(54) 3,4,5-Trifluorophenyl 4-(trans-4-(trans-4-pentylcyclohexyl) cyclohexylmethoxy)benzoate
(55) 3-Fluoro-4-cyanophenyl 2-fluoro-4-(trans-4-methylcyclohexylmethoxy) benzoate
(56) 3-Fluoro-4-cyanophenyl 2-fluoro-4-(trans-4-ethylcyclohexylmethoxy) benzoate
(57) 3-Fluoro-4-cyanophenyl 2-fluoro-4-(trans-4-propylcyclohexylmethoxy) benzoate CN: 82.4° C., NI: 152.0° C.
(58) 3-Fluoro-4-cyanophenyl 2-fluoro-4-(trans-4-butylcyclohexylmethoxy) benzoate
(59) 3-Fluoro-4-cyanophenyl 2-fluoro-4-(trans-4-pentylcyclohexylmethoxy) benzoate
(60) 3-Fluoro-4-cyanophenyl 2-fluoro-4-(trans-4-hexylcyclohexylmethoxy) benzoate
(61) 3-Fluoro-4-cyanophenyl 2-fluoro-4-(trans-4-heptylcyclohexylmethoxy) benzoate
(62) 3-Fluoro-4-cyanophenyl 2-fluoro-4-(trans-4-octylcyclohexylmethoxy) benzoate
(63) 3-Fluoro-4-cyanophenyl 2-fluoro-4-(trans-4-nonylcyclohexylmethoxy) benzoate
(64) 3-Fluoro-4-cyanophenyl 2-fluoro-4-(trans-4-decylcyclohexylmethoxy) benzoate
(65) 3-Fluoro-4-cyanophenyl 2-fluoro-4-(trans-4-propoxycyclohexyl methoxy)benzoate
(66) 3-Fluoro-4-cyanophenyl 2-fluoro-4-(trans-4-butoxycyclohexylmethoxy) benzoate
(67) 3-Fluoro-4-cyanophenyl 2-fluoro-4-(trans-4-pentyloxycyclohexyl methoxy)benzoate
(68) 3-Fluoro-4-cyanophenyl 2-fluoro-4-(trans-4-hexyloxycyclohexyl methoxy)benzoate
(69) 3-Fluoro-4-cyanophenyl 2-fluoro-4-(trans-4-(trans-4-ethylcyclo hexyl)cyclohexylmethoxy)benzoate
(70) 3-Fluoro-4-cyanophenyl 2-fluoro-4-(trans-4-(trans-4-propylcyclo hexyl)cyclohexylmethoxy)benzoate
(71) 3-Fluoro-4-cyanophenyl 2-fluoro-4-(trans-4-(trans-4-butylcyclo hexyl)cyclohexylmethoxy)benzoate
(72) 3-Fluoro-4-cyanophenyl 2-fluoro-4-(trans-4-(trans-4-pentylcyclo hexyl)cyclohexylmethoxy)benzoate
(73) 3,5-Difluoro-4-cyanophenyl 2-fluoro-4-(trans-4-methylcyclohexyl methoxy)benzoate
(74) 3,5-Difluoro-4-cyanophenyl 2-fluoro-4-(trans-4-ethylcyclohexyl methoxy)benzoate
(75) 3,5-Difluoro-4-cyanophenyl 2-fluoro-4-(trans-4-propylcyclohexyl methoxy)benzoate
(76) 3,5-Difluoro-4-cyanophenyl 2-fluoro-4-(trans-4-butylcyclohexyl methoxy)benzoate
(77) 3,5-Difluoro-4-cyanophenyl 2-fluoro-4-(trans-4-pentylcyclohexyl methoxy)benzoate
(78) 3,5-Difluoro-4-cyanophenyl 2-fluoro-4-(trans-4-hexylcyclohexyl methoxy)benzoate
(79) 3,5-Difluoro-4-cyanophenyl 2-fluoro-4-(trans-4-heptylcyclohexyl methoxy)benzoate
(80) 3,5-Difluoro-4-cyanophenyl 2-fluoro-4-(trans-4-octylcyclohexyl methoxy)benzoate
(81) 3,5-Difluoro-4-cyanophenyl 2-fluoro-4-(trans-4-nonylcyclohexyl methoxy)benzoate
(82) 3,5-Difluoro-4-cyanophenyl 2-fluoro-4-(trans-4-decylcyclohexyl methoxy)benzoate
(83) 3,5-Difluoro-4-cyanophenyl 2-fluoro-4-(trans-4-propoxycyclohexyl methoxy)benzoate
(84) 3,5-Difluoro-4-cyanophenyl 2-fluoro-4-(trans-4-butoxycyclohexyl methoxy)benzoate
(85) 3,5-Difluoro-4-cyanophenyl 2-fluoro-4-(trans-4-pentyloxycyclohexyl methoxy)benzoate
(86) 3,5-Difluoro-4-cyanophenyl 2-fluoro-4-(trans-4-hexyloxycyclohexyl methoxy)benzoate
(87) 3,5-Difluoro-4-cyanophenyl 2-fluoro-4-(trans-4-(trans-4-ethylcyclo hexyl)cyclohexylmethoxy)benzoate
(88) 3,5-Difluoro-4-cyanophenyl 2-fluoro-4-(trans-4-(trans-4-propylcyclo hexyl)cyclohexylmethoxy)benzoate
(89) 3,5-Difluoro-4-cyanophenyl 2-fluoro-4-(trans-4-(trans-4-butylcyclo hexyl)cyclohexylmethoxy)benzoate
(90) 3,5-Difluoro-4-cyanophenyl 2-fluoro-4-(trans-4-(trans-4-pentylcyclo hexyl)cyclohexylmethoxy)benzoate
(91) 3,4,5-Trifluorophenyl 2-fluoro-4-(trans-4-methylcyclohexylmethoxy) benzoate
(92) 3,4,5-Trifluorophenyl 2-fluoro-4-(trans-4-ethylcyclohexylmethoxy) benzoate CI: 80.6° C., NI: 48.8° C.
(93) 3,4,5-Trifluorophenyl 2-fluoro-4-(trans-4-propylcyclohexylmethoxy) benzoate

(94) 3,4,5-Trifluorophenyl 2-fluoro-4-(trans-4-butylcyclohexylmethoxy) benzoate
(95) 3,4,5-Trifluorophenyl 2-fluoro-4-(trans-4-pentylcyclohexylmethoxy) benzoate
(96) 3,4,5-Trifluorophenyl 2-fluoro-4-(trans-4-hexylcyclohexylmethoxy) benzoate
(97) 3,4,5-Trifluorophenyl 2-fluoro-4-(trans-4-heptylcyclohexylmethoxy) benzoate
(98) 3,4,5-Trifluorophenyl 2-fluoro-4-(trans-4-octylcyclohexylmethoxy) benzoate
(99) 3,4,5-Trifluorophenyl 2-fluoro-4-(trans-4-nonylcyclohexylmethoxy) benzoate
(100) 3,4,5-Trifluorophenyl 2-fluoro-4-(trans-4-decylcyclohexylmethoxy) benzoate
(101) 3,4,5-Trifluorophenyl 2-fluoro-4-(trans-4-propoxycyclohexyl methoxy)benzoate
(102) 3,4,5-Trifluorophenyl 2-fluoro-4-(trans-4-butoxycyclohexylmethoxy) benzoate
(103) 3,4,5-Trifluorophenyl 2-fluoro-4-(trans-4-pentyloxycyclohexyl methoxy)benzoate
(104) 3,4,5-Trifluorophenyl 2-fluoro-4-(trans-4-hexyloxycyclohexyl methoxy)benzoate
(105) 3,4,5-Trifluorophenyl 2-fluoro-4-(trans-4-(trans-4-ethylcyclo hexyl)cyclohexylmethoxy)benzoate
(106) 3,4,5-Trifluorophenyl 2-fluoro-4-(trans-4-(trans-4-propylcyclo hexyl)cyclohexylmethoxy)benzoate
(107) 3,4,5-Trifluorophenyl 2-fluoro-4-(trans-4-(trans-4-butylcyclo hexyl)cyclohexylmethoxy)benzoate
(108) 3,4,5-Trifluorophenyl 2-fluoro-4-(trans-4-(trans-4-pentylcyclo hexyl)cyclohexylmethoxy)benzoate
(228) 3,5-Difluoro-4-trifluoromethylphenyl 4-(trans-4-pentylcyclo hexylmethoxy)benzoate
(229) 3,5-Difluoro-4-trifluoromethoxylphenyl 4-(trans-4-pentylcyclohexyl methoxy)benzoate Example 2

3-Fluoro-4-cyanophenyl 2,6-difluoro-4-(trans-4-prolylcyclohexyl methoxy)benzoate (Preparation of compound (109) represented by the formula (I) wherein $B_1$ is 2,6-difluoro-1,4-phenylene, Y is a cyano group, X is a hydrogen atom, $R_1$ is a n-propyl group, n is 1, m is 1, and p is 0)

1) Potassium-t-butoxide (176 g) and 3,5-difluorophenol (200 g) were suspended in tetrahydrofuran (hereinafter referred to as "THF") (500 ml).

To this mixture was dropped methyl iodide (222 g), and then the resulting was stirred under reflux for 4 hours. After the reaction, the mixture was cooled, added with diluted hydrochloric acid (500 ml) and extracted with ethyl acetate (1 liter). The organic layer separated was washed with water, dried over anhydrous magnesium sulfate, and then the solvent was distilled off under reduced pressure to give 3,5-difluoroanisol (134 g).

2) To THF (200 ml) was dissolved 3,5-difluoroanisol (134 g) and then 1.64 M of n-butyllithium/hexane (568 ml) was added and stirred for 1 hour. The mixture formed was added to a solution of dryice (9.4 g) dissolved in THF (100 ml), and was stirred at room temperature for 2 hours.

After the reaction, the mixture was added with diluted hydrochloric acid (700 ml) and extracted with ethyl acetate (700 ml). The organic layer separated was washed with water, dried over anhydrous magnesium sulfate, and then the solvent was distilled off under reduced pressure to give 2,6-difluoro-4-methoxybenzoic acid (102 g).

3) To methanol (300 ml) was dissolved 2,6-difluoro-4-methoxybenzoic acid (102 g) and then concentrated sulfuric acid (1 ml) was added and stirred under reflux for 3 hours. After the reaction, the mixture was extracted with ethyl acetate (400 ml). The organic layer separated was washed with water, dried over anhydrous magnesium sulfate, and then the solvent was distilled off under reduced pressure to give methyl 2,6-difluoro-4-methoxybenzoate (90 g).

4) To the above methyl 2,6-difluoro-4-methoxybenzoate (90 g) was added boron tribromide (224 g) under cooling, and then the mixture was stirred for 2 hours at room temperature. After the reaction, the reaction mixture was extracted with ethyl acetate (300 ml). The organic layer separated was washed with water, dried over anhydrous magnesium sulfate, and then the solvent was distilled off under reduced pressure. The residue was distilled under reduced pressure to give methyl 2,6-difluoro-4-hydroxybenzoate (56 g).

5) A solution of potassium hydroxide (17 g) dissolved in water (10 ml), and the above methyl 2,6-difluoro-4-hydroxybenzoate (56 g) were suspended in 500 ml of ethyleneglycolmonoethylether. To this mixture was added trans-4-propylcyclohexylmethylbromide (66.5 g), and then the resulting mixture was stirred under reflux for 4 hours. After cooling to room temperature, a solution of sodium hydroxide (24 g) dissolved in water (120 ml) was added with stirring and refluxed for 2 hours. After the reaction, the mixture was cooled, added with diluted hydrochloric acid (300 ml), and then extracted with toluene (500 ml). The organic layer separated was washed with water, dried over anhydrous magnesium sulfate, and then the solvent was distilled off under reduced pressure to obtain 2,6-difluoro-4-(trans-4-propylcyclohexylmethoxy)benzoate (49 g).

6) To toluene (150 ml) was suspended the above 2,6-difluoro-4-(trans-4-propylcyclohexylmethoxy)benzoic acid (49 g), and then thionyl chloride (19 g) was added with stirring and refluxed for 2 hours. After cooling to room temperature, a solution of 3-fluoro-4-cyanophenol (22 g) dissolved in pyridine (13 g) was added and stirred at room temperature for 2 hours. After the reaction, diluted hydrochloric acid (200 ml) was added to the mixture and was extracted with toluene (400 ml). The organic layer separated was washed with water, dried over anhydrous magnesium sulfate, and then the solvent was distilled off under reduced pressure to give cinnamon-colored oil. The oil was recrystallized from ethyl acetate to give the above-captioned compound (29 g).

In the similar manner to those of Example 2, the following compounds (110) to (161) can be prepared.
(110) 3-Fluoro-4-cyanophenyl 2,6-difluoro-4-(trans-4-methylcyclohexyl methoxy)benzoate
(111) 3-Fluoro-4-cyanophenyl 2,6-difluoro-4-(trans-4-ethylcyclohexyl methoxy)benzoate
(112) 3-Fluoro-4-cyanophenyl 2,6-difluoro-4-(trans-4-butylcyclohexyl methoxy)benzoate
(113) 3-Fluoro-4-cyanophenyl 2,6-difluoro-4-(trans-4-pentylcyclohexyl methoxy)benzoate
(114) 3-Fluoro-4-cyanophenyl 2,6-difluoro-4-(trans-4-hexylcyclohexyl methoxy)benzoate
(115) 3-Fluoro-4-cyanophenyl 2,6-difluoro-4-(trans-4-heptylcyclohexyl methoxy)benzoate
(116) 3-Fluoro-4-cyanophenyl 2,6-difluoro-4-(trans-4-octylcyclohexyl methoxy)benzoate
(117) 3-Fluoro-4-cyanophenyl 2,6-difluoro-4-(trans-4-nonylcyclohexyl methoxy)benzoate
(118) 3-Fluoro-4-cyanophenyl 2,6-difluoro-4-(trans-4-decylcyclohexyl methoxy)benzoate
(119) 3-Fluoro-4-cyanophenyl 2,6-difluoro-4-(trans-4-propoxycyclohexyl methoxy)benzoate (120) 3-Fluoro-4-cyanophenyl 2,6-difluoro-4-(trans-4-butoxycyclohexyl methoxy)benzoate
(121) 3-Fluoro-4-cyanophenyl 2,6-difluoro-4-(trans-4-pentyloxycyclohexyl methoxy)benzoate
(122) 3-Fluoro-4-cyanophenyl 2,6-difluoro-4-(trans-4-hexyloxycyclohexyl methoxy)benzoate
(123) 3-Fluoro-4-cyanophenyl 2,6-difluoro-4-(trans-4-(trans-4-ethylcyclo hexyl)cyclohexylmethoxy)benzoate
(124) 3-Fluoro-4-cyanophenyl 2,6-difluoro-4-(trans-4-(trans-4-propyl cyclohexyl)cyclohexylmethoxy)benzoate
(125) 3-Fluoro-4-cyanophenyl 2,6-difluoro-4-(trans-4-(trans-4-butylcyclo hexyl)cyclohexylmethoxy)benzoate
(126) 3-Fluoro-4-cyanophenyl 2,6-difluoro-4-(trans-4-(trans-4-pentyl cyclohexyl)cyclohexylmethoxy)benzoate
(127) 3,5-Difluoro-4-cyanophenyl 2,6-difluoro-4-(trans-4-methylcyclo hexylmethoxy)benzoate
(128) 3,5-Difluoro-4-cyanophenyl 2,6-difluoro-4-(trans-4-ethylcyclohexyl methoxy)benzoate
(129) 3,5-Difluoro-4-cyanophenyl 2,6-difluoro-4-(trans-4-propylcyclo hexylmethoxy)benzoate
(130) 3,5-Difluoro-4-cyanophenyl 2,6-difluoro-4-(trans-4-butylcyclo hexylmethoxy)benzoate
(131) 3,5-Difluoro-4-cyanophenyl 2,6-difluoro-4-(trans-4-pentylcyclo hexylmethoxy)benzoate
(131) 3,5-Difluoro-4-cyanophenyl 2,6-difuluoro-4-(trans-4-hexylcyclo hexylmethoxy)benzoate
(132) 3,5-Difluoro-4-cyanophenyl 2,6-difuluoro-4-(trans-4-heptylcyclo hexylmethoxy)benzoate
(133) 3,5-Difluoro-4-cyanophenyl 2,6-difuluoro-4-(trans-4-octylcyclo hexylmethoxy)benzoate
(134) 3,5-Difluoro-4-cyanophenyl 2,6-difuluoro-4-(trans-4-nonylcyclo hexylmethoxy)benzoate
(135) 3,5-Difluoro-4-cyanophenyl 2,6-difuluoro-4-(trans-4-decylcyclo hexylmethoxy)benzoate
(136) 3,5-Difluoro-4-cyanophenyl 2,6-difuluoro-4-(trans-4-propoxycyclo hexylmethoxy)benzoate
(137) 3,5-Difluoro-4-cyanophenyl 2,6-difuluoro-4-(trans-4-butoxycyclo hexylmethoxy)benzoate
(138) 3,5-Difluoro-4-cyanophenyl 2,6-difuluoro-4-(trans-4-butoxycyclo hexylmethoxy)benzoate
(139) 3,5-Difluoro-4-cyanophenyl 2,6-difuluoro-4-(trans-4-hexyloxycyclo hexylmethoxy)benzoate
(140) 3,5-Difluoro-4-cyanophenyl 2,6-difuluoro-4-(trans-4-(trans-4-ethyl cyclohexyl)cyclohexylmethoxy)benzoate
(141) 3,5-Difluoro-4-cyanophenyl 2,6-difuluoro-4-(trans-4-(trans-4-propyl cyclohexyl)cyclohexylmethoxy)benzoate
(142) 3,5-Difluoro-4-cyanophenyl 2,6-difuluoro-4-(trans-4-(trans-4-butyl cyclohexyl)cyclohexylmethoxy)benzoate
(143) 3,5-Difluoro-4-cyanophenyl 2,6-difuluoro-4-(trans-4-(trans-4-pentyl cyclohexyl)cyclohexylmethoxy)benzoate
(144) 3,4,5-Trifluorophenyl 2,6-difuluoro-4-(trans-4-methylcyclohexyl methoxy)benzoate
(145) 3,4,5-Trifluorophenyl 2,6-difuluoro-4-(trans-4-ethylcyclohexyl methoxy)benzoate
(146) 3,4,5-Trifluorophenyl 2,6-difuluoro-4-(trans-4-propylcyclohexyl methoxy)benzoate
(147) 3,4,5-Trifluorophenyl 2,6-difuluoro-4-(trans-4-butylcyclohexyl methoxy)benzoate
(148) 3,4,5-Trifluorophenyl 2,6-difuluoro-4-(trans-4-pentylcyclohexyl methoxy)benzoate
(149) 3,4,5-Trifluorophenyl 2,6-difuluoro-4-(trans-4-hexylcyclohexyl methoxy)benzoate
(150) 3,4,5-Trifluorophenyl 2,6-difuluoro-4-(trans-4-heptylcyclohexyl methoxy)benzoate
(151) 3,4,5-Trifluorophenyl 2,6-difuluoro-4-(trans-4-octylcyclohexyl methoxy)benzoate
(152) 3,4,5-Trifluorophenyl 2,6-difuluoro-4-(trans-4-nonylcyclohexyl methoxy)benzoate
(153) 3,4,5-Trifluorophenyl 2,6-difuluoro-4-(trans-4-decylcyclohexyl methoxy)benzoate
(154) 3,4,5-Trifluorophenyl 2,6-difuluoro-4-(trans-4-propoxycyclohexyl methoxy)benzoate
(155) 3,4,5-Trifluorophenyl 2,6-difuluoro-4-(trans-4-butoxycyclohexyl methoxy)benzoate
(156) 3,4,5-Trifluorophenyl 2,6-difuluoro-4-(trans-4-pentyloxycyclohexyl methoxy)benzoate
(157) 3,4,5-Trifluorophenyl 2,6-difuluoro-4-(trans-4-hexyloxycyclohexyl methoxy)benzoate
(158) 3,4,5-Trifluorophenyl 2,6-difuluoro-4-(trans-4-(trans-4-ethylcyclo hexyl)cyclohexylmethoxy)benzoate
(159) 3,4,5-Trifluorophenyl 2,6-difuluoro-4-(trans-4-(trans-4-propylcyclo hexyl)cyclohexylmethoxy)benzoate
(160) 3,4,5-Trifluorophenyl 2,6-difuluoro-4-(trans-4-(trans-4-butylcyclo hexyl)cyclohexylmethoxy)benzoate
(161) 3,4,5-Trifluorophenyl 2,6-difuluoro-4-(trans-4-(trans-4-pentylcyclo hexyl)cyclohexylmethoxy)benzoate Example 3

3-Fluoro-4-cyanophenyl trans-4-(trans-4-propylcyclohexylmethoxy) cyclohexanecarboxylate (Preparation of compound (162) represented by the formula (I) wherein $B_1$ is trans-1,4-cyclohexylene, Y is a cyano group, X is a hydrogen atom, $R_1$ is a n-propyl group, n is 1, m is 1, and p is 0)

1) A solution of potassium hydroxide (52.3 g) dissolved in 30 ml of water, and methyl 4-hydroxybenzoate (142 g) were suspended in 1500 ml of ethyleneglycolmonoethylether. To this mixture was added trans-4-propylclohexylmethylbromide (200 g), and then the mixture formed was stirred under reflux for 4 hours. After cooling to room temperature, a solution of sodium hydroxide (80 g) dissolved in water (400 ml) was added with stirring and refluxed for 2 hours. After the reaction, the mixture was cooled, added with diluted hydrochloric acid (1 liter), and extracted with toluene (5 liters). The organic layer separated was washed with water, dried over anhydrous magnesium sulfate, and the solvent was distilled off under reduced pressure to give 4-(trans-4-prolylcyclohexylmethoxy) benzoic acid (166 g).

2) The 4-(trans-4-prolylcyclohexylmethoxy)benzoic acid (166 g) above was suspended in a solution of sodium hydroxide (24 g) dissolved in 1 liter of water, ruthenium/carbon (5%) as a catalyst was added thereto, and catalytic reduction was carried out under atmosphere of hydrogen. After the reaction, the catalyst was filtered. The mixture was added with diluted hydrochloric acid (1 liter), and extracted with toluene (1 liter).

The organic layer separated was washed with water, dried over anhydrous magnesium sulfate, and then the solvent was distilled off under reduced pressure to give cinnamon-colored oil. The oil was recrystallized from ethanol to give trans-4-(trans-4-propylcyclohexylmethoxy)cyclohexane carboxylic acid (50 g).

3) To toluene (150 ml) was suspended the above trans-4-(trans-4-propylcyclohexylmethoxy)cyclohexane carboxylic acid (50 g), and then thionyl chloride (21.5 g) was added with stirring and refluxed for 2 hours. After cooling to room temperature, a solution of 3-fluoro-4-cyanophenol (24.8 g) dissolved in pyridine (14.3 g) was added and stirred at room temperature for 2 hours. After the reaction, the mixture was added with diluted hydrochloric acid (200 ml) and extracted with toluene (400 ml). The organic layer separated was washed with water, dried over anhydrous magnesium sulfate, and then the solvent was distilled off under reduced pressure to give cinnamon-colored oil. The oil was recrystallized from ethyl acetate to give the above-captioned compound (32 g). CN: 71.7° C., NI: 161.9° C.

In the similar manner to those of Example 3, the following compounds (163) to (227) can be prepared.

(163) 3-Fluoro-4-cyanophenyl trans-4-(trans-4-methylcyclohexylmethoxy) cyclohexane carboxylate
(164) 3-Fluoro-4-cyanophenyl trans-4-(trans-4-ethylcyclohexylmethoxy) cyclohexane carboxylate
(165) 3-Fluoro-4-cyanophenyl trans-4-(trans-4-butylcyclohexylmethoxy) cyclohexane carboxylate
(166) 3-Fluoro-4-cyanophenyl trans-4-(trans-4-pentylcyclohexylmethoxy) cyclohexane carboxylate
(167) 3-Fluoro-4-cyanophenyl trans-4-(trans-4-hexylcyclohexylmethoxy) cyclohexane carboxylate
(168) 3-Fluoro-4-cyanophenyl trans-4-(trans-4-heptylcyclohexylmethoxy) cyclohexane carboxylate
(169) 3-Fluoro-4-cyanophenyl trans-4-(trans-4-octylcyclohexylmethoxy) cyclohexane carboxylate
(170) 3-Fluoro-4-cyanophenyl trans-4-(trans-4-nonylcyclohexylmethoxy) cyclohexane carboxylate
(171) 3-Fluoro-4-cyanophenyl trans-4-(trans-4-decylcyclohexylmethoxy) cyclohexane carboxylate
(172) 3-Fluoro-4-cyanophenyl trans-4-(trans-4-propoxycyclohexylmethoxy) cyclohexane carboxylate
(173) 3-Fluoro-4-cyanophenyl trans-4-(trans-4-butoxycyclohexylmethoxy) cyclohexane carboxylate
(174) 3-Fluoro-4-cyanophenyl trans-4-(trans-4-pentyloxycyclohexylmethoxy cyclohexane carboxylate
(175) 3-Fluoro-4-cyanophenyl trans-4-(trans-4-hexyloxycyclohexylmethoxy) cyclohexane carboxylate
(176) 3-Fluoro-4-cyanophenyl trans-4-(trans-4-(trans-4-ethylcyclohexyl) cyclohexylmethoxy)cyclohexane carboxylate
(177) 3-Fluoro-4-cyanophenyl trans-4-(trans-4-(trans-4-propylcyclohexyl) cyclohexylmethoxy)cyclohexane carboxylate
(178) 3-Fluoro-4-cyanophenyl trans-4-(trans-4-(trans-4-butylcyclohexyl) cyclohexylmethoxy)cyclohexane carboxylate
(179) 3-Fluoro-4-cyanophenyl trans-4-(trans-4-(trans-4-pentylcyclohexyl) cyclohexylmethoxy)cyclohexane carboxylate
(180) 3-Fluoro-4-cyanophenyl trans-4-(trans-4-(trans-4-ethylcyclohexyl methoxy)cyclohexyl)cyclohexane carboxylate
(181) 3-Fluoro-4-cyanophenyl trans-4-(trans-4-(trans-4-propylclohexyl methoxy)cyclohexyl)cyclohexane carboxylate
(182) 3-Fluoro-4-cyanophenyl trans-4-(trans-4-(trans-4-butylclohexyl methoxy)cyclohexyl)cyclohexane carboxylate
(183) 3-Fluoro-4-cyanophenyl trans-4-(trans-4-(trans-4-pentylcyclohexyl methoxy)cyclohexyl)cyclohexane carboxylate
(184) 3,5-Difluoro-4-cyanophenyl trans-4-(trans-4-methylcyclohexyl methoxy)cyclohexane carboxylate
(185) 3,5-Difluoro-4-cyanophenyl trans-4-(trans-4-ethylcyclohexylmethoxy) cyclohexane carboxylate
(186) 3,5-Difluoro-4-cyanophenyl trans-4-(trans-4-propylcyclohexyl methoxy)cyclohexane carboxylate
(187) 3,5-Difluoro-4-cyanophenyl trans-4-(trans-4-butylcyclohexylmethoxy) cyclohexane carboxylate
(188) 3,5-Difluoro-4-cyanophenyl trans-4-(trans-4-pentylcyclohexyl methoxy)cyclohexane carboxylate
(189) 3,5-Difluoro-4-cyanophenyl trans-4-(trans-4-hexylcyclohexylmethoxy) cyclohexane carboxylate
(190) 3,5-Difluoro-4-cyanophenyl trans-4-(trans-4-heptylcyclohexyl methoxy)cyclohexane carboxylate
(191) 3,5-Difluoro-4-cyanophenyl trans-4-(trans-4-octylcyclohexylmethoxy) cyclohexane carboxylate
(192) 3,5-Difluoro-4-cyanophenyl trans-4-(trans-4-nonylcyclohexylmethoxy) cyclohexane carboxylate
(193) 3,5-Difluoro-4-cyanophenyl trans-4-(trans-4-decylcyclohexyl methoxy)cyclohexane carboxylate
(194) 3,5-Difluoro-4-cyanophenyl trans-4-(trans-4-propoxycyclohexyl methoxy)cyclohexane carboxylate
(195) 3,5-Difluoro-4-cyanophenyl trans-4-(trans-4-butoxycyclohexyl methoxy)cyclohexane carboxylate
(196) 3,5-Difluoro-4-cyanophenyl trans-4-(trans-4-pentyloxycyclohexyl methoxy)cyclohexane carboxylate
(197) 3,5-Difluoro-4-cyanophenyl trans-4-(trans-4-hexyloxycyclohexyl methoxy)cyclohexane carboxylate
(198) 3,5-Difluoro-4-cyanophenyl trans-4-(trans-4-(trans-4-ethylcyclohexyl)cyclohexylmethoxy)cyclohexane carboxylate
(199) 3,5-Difluoro-4-cyanophenyl trans-4-(trans-4-(trans-4-propylcyclo hexyl)cyclohexylmethoxy)cyclohexane carboxylate
(200) 3,5-Difluoro-4-cyanophenyl trans-4-(trans-4-(trans-4-butylcyclo hexyl)cyclohexylmethoxy)cyclohexane carboxylate
(201) 3,5-Difluoro-4-cyanophenyl trans-4-(trans-4-(trans-4-pentylcyclo hexyl)cyclohexylmethoxy)cyclohexane carboxylate
(202) 3,5-Difluoro-4-cyanophenyl trans-4-(trans-4-(trans-4-ethylcyclo hexylmethoxy)cyclohexyl)cyclohexane carboxylate
(203) 3,5-Difluoro-4-cyanophenyl trans-4-(trans-4-(trans-4-propylcyclo hexylmethoxy)cyclohexyl)cyclohexane carboxylate
(204) 3,5-Difluoro-4-cyanophenyl trans-4-(trans-4-(trans-4-butylcyclo hexylmethoxy)cyclohexyl)cyclohexane carboxylate
(205) 3,5-Difluoro-4-cyanophenyl trans-4-(trans-4-(trans-4-pentylcyclo hexylmethoxy)cyclohexyl)cyclohexane carboxylate
(206) 3,4,5-Trifluorophenyl trans-4-(trans-4-methylcyclohexylmethoxy) cyclohexane carboxylate
(207) 3,4,5-Trifluorophenyl trans-4-(trans-4-ethylcyclohexylmethoxy) cyclohexane carboxylate
(208) 3,4,5-Trifluorophenyl trans-4-(trans-4-propylcyclohexylmethoxy) cyclohexane carboxylate CI: 94.0° C., NI: 89.0° C.
(209) 3,4,5-Trifluorophenyl trans-4-(trans-4-butylcyclohexylmethoxy) cyclohexane carboxylate
(210) 3,4,5-Trifluorophenyl trans-4-(trans-4-pentylcyclohexylmethoxy) cyclohexane carboxylate
(211) 3,4,5-Trifluorophenyl trans-4-(trans-4-hexylcyclohexylmethoxy) cyclohexane carboxylate
(212) 3,4,5-Trifluorophenyl trans-4-(trans-4-heptylcyclohexylmethoxy) cyclohexane carboxylate
(213) 3,4,5-Trifluorophenyl trans-4-(trans-4-octylcyclohexylmethoxy) cyclohexane carboxylate
(214) 3,4,5-Trifluorophenyl trans-4-(trans-4-nonylcyclohexylmethoxy) cyclohexane carboxylate
(215) 3,4,5-Trifluorophenyl trans-4-(trans-4-decylcyclohexylmethoxy) cyclohexane carboxylate
(216) 3,4,5-Trifluorophenyl trans-4-(trans-4-propoxycyclohexylmethoxy) cyclohexane carboxylate
(217) 3,4,5-Trifluorophenyl trans-4-(trans-4-butoxycyclohexylmethoxy) cyclohexane carboxylate
(218) 3,4,5-Trifluorophenyl trans-4-(trans-4-pentyloxycyclohexylmethoxy) cyclohexane carboxylate (219) 3,4,5-Trifluorophenyl trans-4-(trans-4-hexyloxycyclohexylmethoxy) cyclohexane carboxylate
(220) 3,4,5-Trifluorophenyl trans-4-(trans-4-(trans-4-ethylcyclohexyl) cyclohexylmethoxy)cyclohexane carboxylate
(221) 3,4,5-Trifluorophenyl trans-4-(trans-4-(trans-4-propylcyclohexyl) cyclohexylmethoxy)cyclohexane carboxylate
(222) 3,4,5-Trifluorophenyl trans-4-(trans-4-(trans-4-butylcyclohexyl) cyclohexylmethoxy)cyclohexane carboxylate
(223) 3,4,5-Trifluorophenyl trans-4-(trans-4-(trans-4-pentylcyclohexyl) cyclohexylmethoxy)cyclohexane carboxylate
(224) 3,4,5-Trifluorophenyl trans-4-(trans-4-(trans-4-ethylcyclohexyl methoxy)cyclohexyl)cyclohexane carboxylate
(225) 3,4,5-Trifluorophenyl trans-4-(trans-4-(trans-4-ethylcyclohexyl methoxy)cyclohexyl)cyclohexane carboxylate
(226) 3,4,5-Trifluorophenyl trans-4-(trans-4-(trans-4-butylcyclohexyl methoxy)cyclohexyl)cyclohexane carboxylate
(227) 3,4,5-Trifluorophenyl trans-4-(trans-4-(trans-4-pentylcyclohexyl methoxy)cyclohexyl)cyclohexane carboxylate Example 4 (Composition Example 1)

A liquid crystal composition, ZLI-1132, which was commercially available from Merck Company had 72.4° C. of NI, 1.78 V of threshold voltage at cell thickness of 9 μm, 11.0 of dielectric anisotropy (Δε) and 0.137 of optical anisotropy (Δn). To 90 parts by weight of the above liquid crystal composition was added 10 parts by weight of the compound (1) obtained by the Example 1 according to the present invention to prepare a liquid composition. The liquid crystal composition thus prepared had 77.5° C. of NI, 1.64 V of threshold voltage at cell thickness of 9 μm, 12.4 of Δε and 0.141 of Δn. Extrapolation values calculated from the mixing ratio were 123.4° C. of NI, 25.0 of Δε and 0.179 of Δn.

Example 5 (Composition Example 2)

To 90 parts by weight of ZLI-1132 was added 10 parts by weight of the compound (39) according to the present invention to prepare a liquid crystal composition. The liquid crystal composition thus prepared had 72.3° C. of NI, 1.58 V of threshold voltage at cell thickness of 9 μm, 11.6 of Δε and 0.135 of Δn. Extrapolation values calculated from the mixing ratio were 71.4° C. of NI, 17.0 of Δε and 0.121 of Δn.

Example 6 (Composition Example 3)

To 85 parts by weight of ZLI-1132 was added 15 parts by weight of the compound (57) according to the present invention to prepare a liquid crystal composition. The liquid crystal composition thus prepared had 80.0° C. of NI, 1.60 V of threshold voltage at cell thickness of 9 μm, 13.3 of Δε and 0.143 of Δn. Extrapolation values calculated from the mixing ratio were 123.1° C. of NI, 26.3 of Δε and 0.177 of Δn.

Example 7 (Composition Example 4)

To 85 parts by weight of ZLI-1132 was added 15 parts by weight of the compound (92) according to the present invention to prepare a liquid crystal composition. The liquid crystal composition thus prepared had 67.5° C. of NI, 1.44 V of threshold voltage at cell thickness of 9 μm, 12.5 of Δε and 0.131 of Δn. Extrapolation values calculated from the mixing ratio were 39.7° C. of NI, 21.0 of Δε and 0.097 of Δn.

A liquid crystal composition comprising a compound according to the present invention is further exemplified below. A numeral in parentheses after the formula of a compound means the compound's number, and % means percentage by weight in a composition.

Example 8 (Composition Example 5)

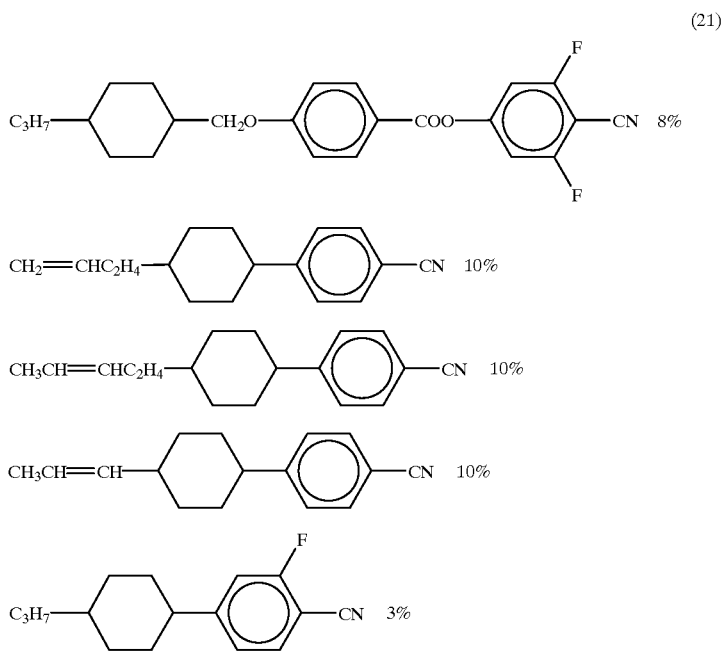

-continued
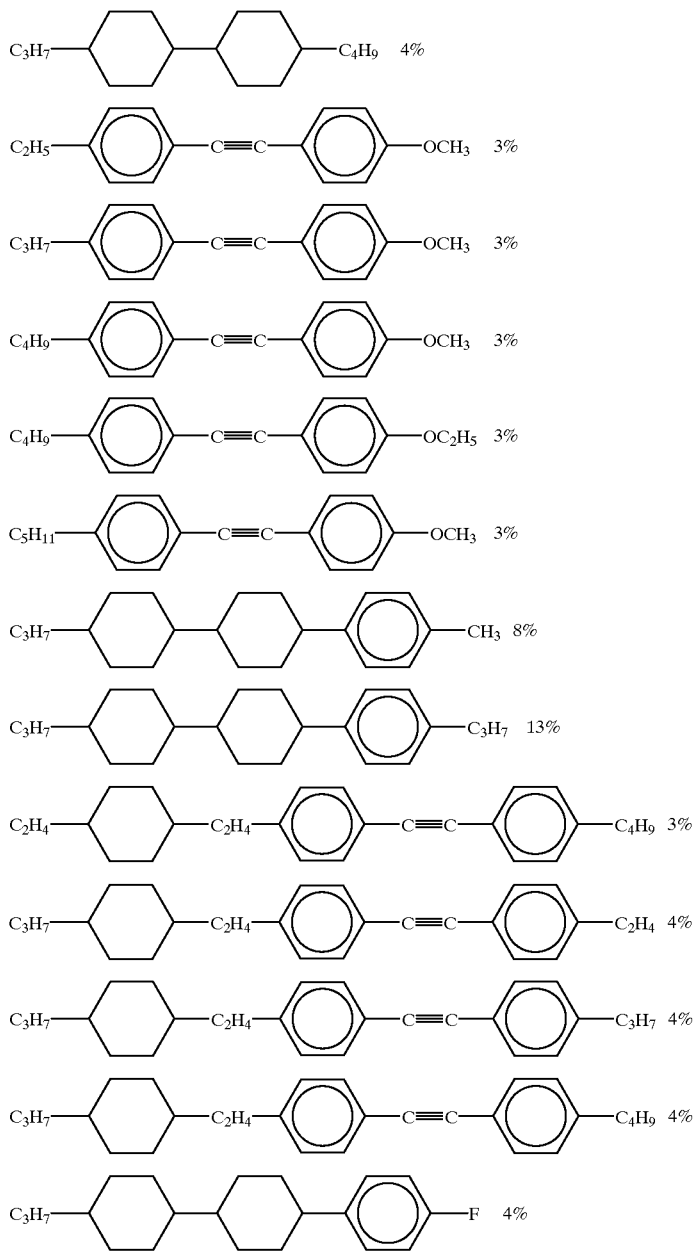
Example 9 (Composition Example 6)
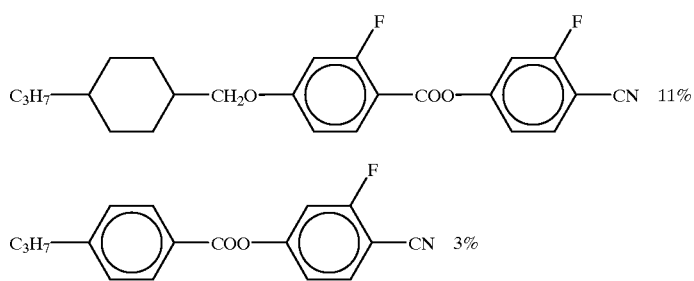
(57)

-continued
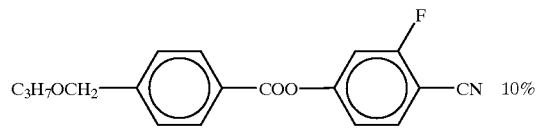 10%
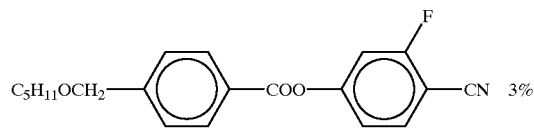 3%
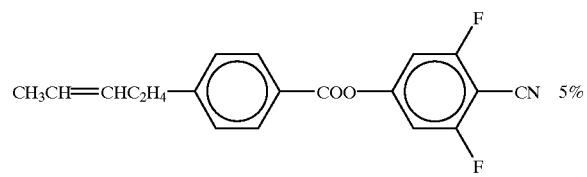 5%
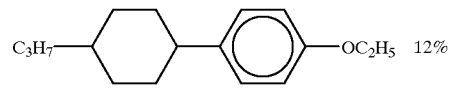 12%
 7%
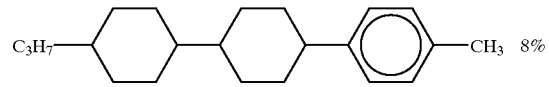 8%
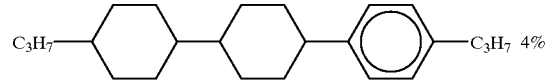 4%
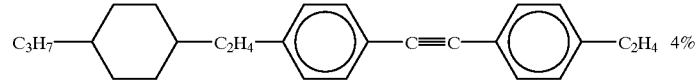 4%
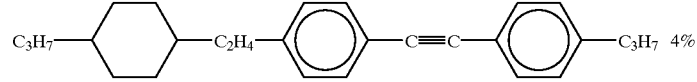 4%
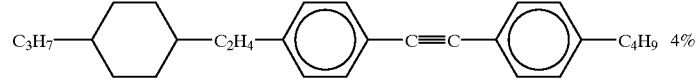 4%
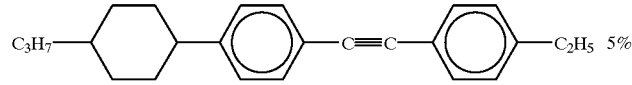 5%
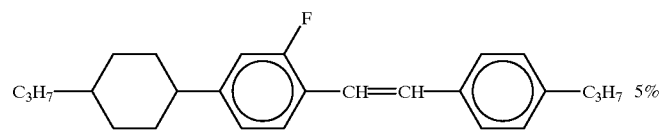 5%
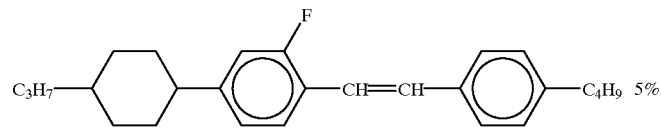 5%
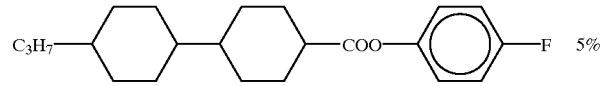 5%
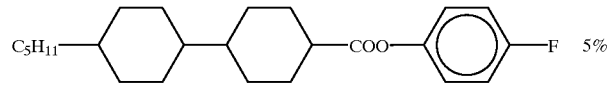 5%

Example 10 (Composition Example 7)
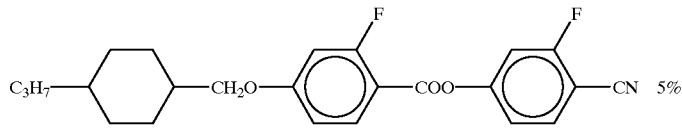 (57) 5%
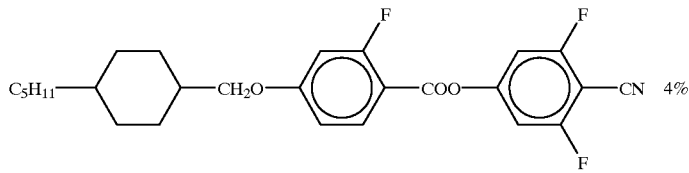 (77) 4%
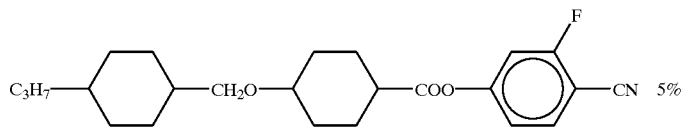 (162) 5%
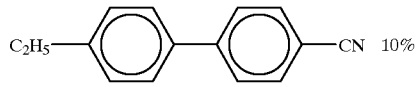 10%
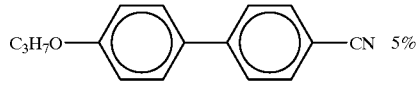 5%
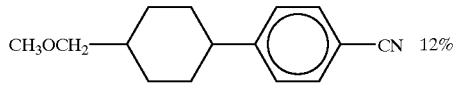 12%
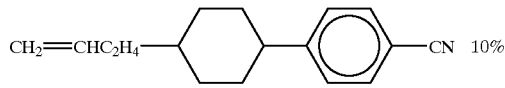 10%
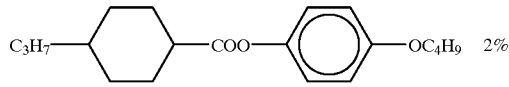 2%
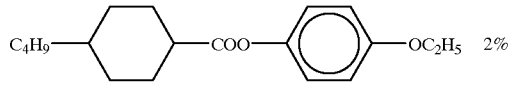 2%
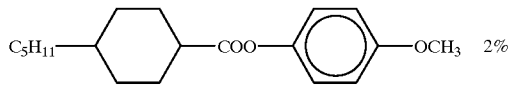 2%
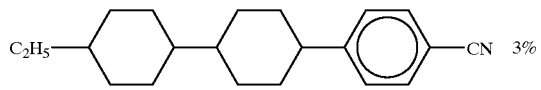 3%
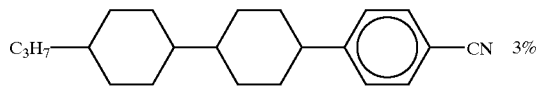 3%
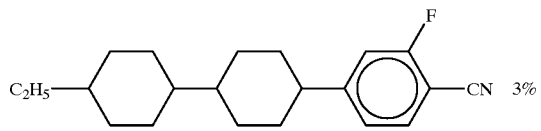 3%
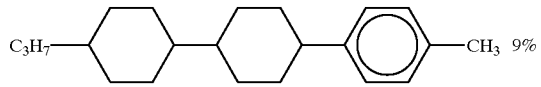 9%

-continued
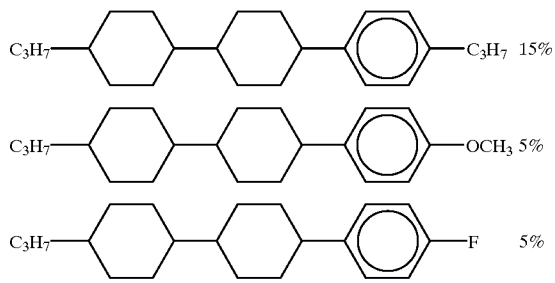
Example 11 (Composition Example 8)
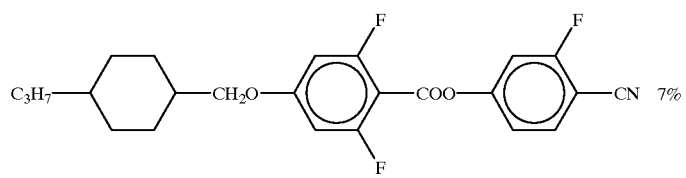  (109)
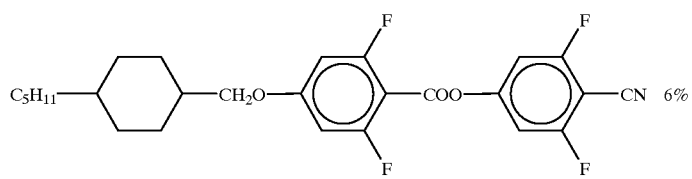  (131)
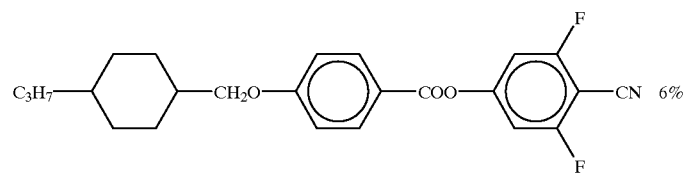  (21)
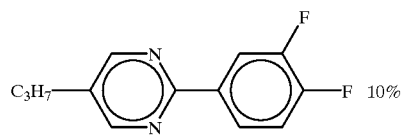  10%
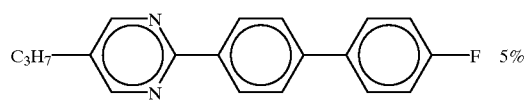  5%
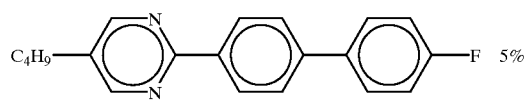  5%
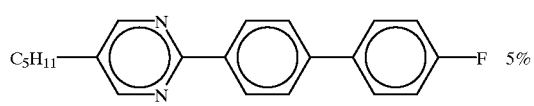  5%
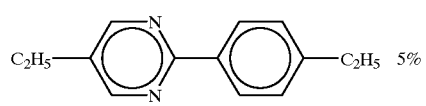  5%
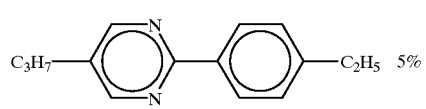  5%

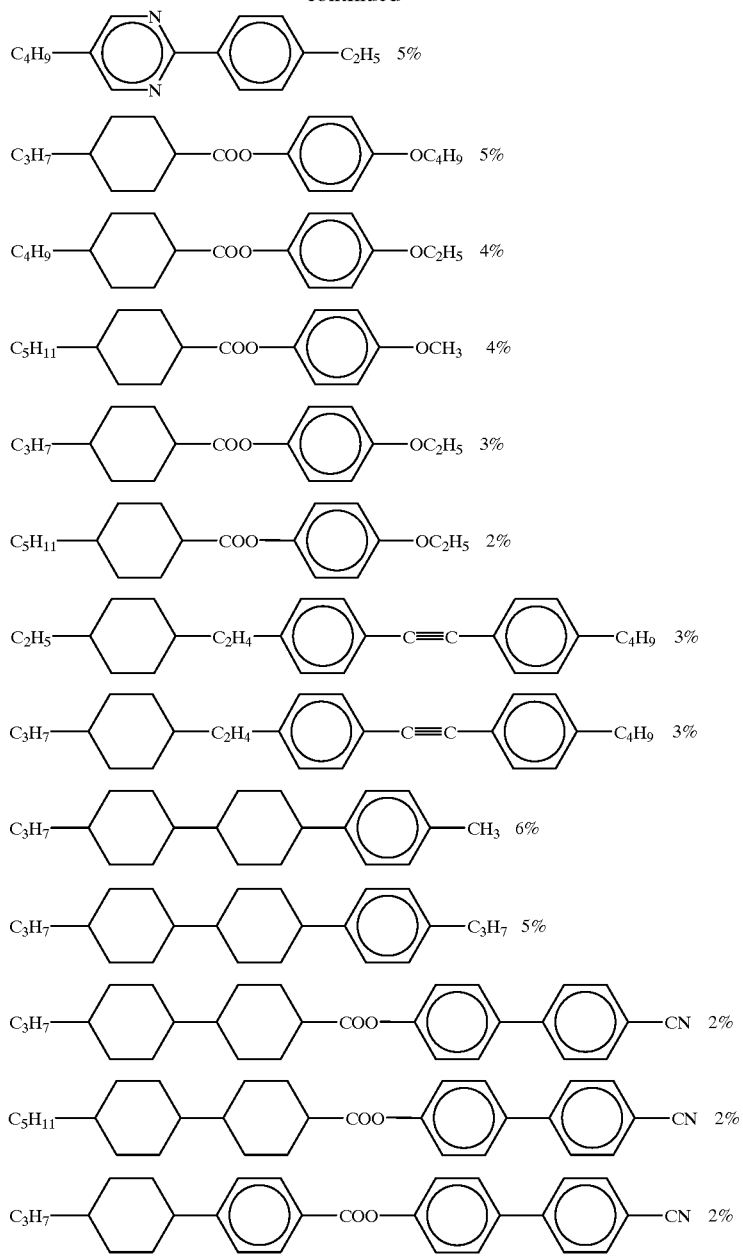
Example 12 (Composition Example 9)
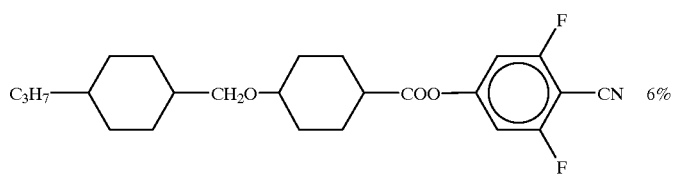
(186)

(162)
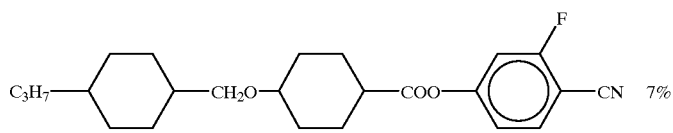 7%
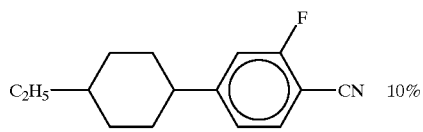 10%
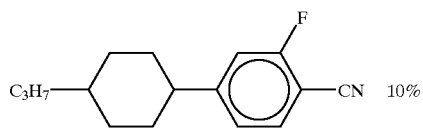 10%
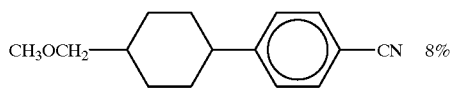 8%
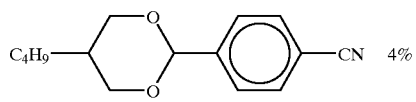 4%
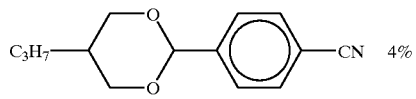 4%
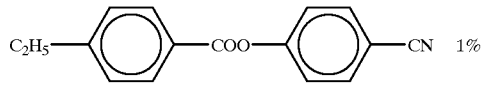 1%
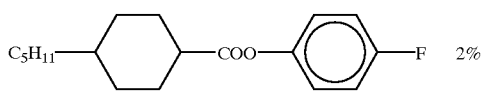 2%
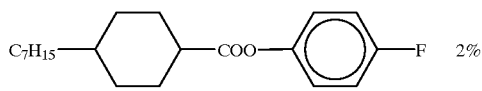 2%
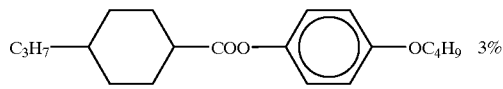 3%
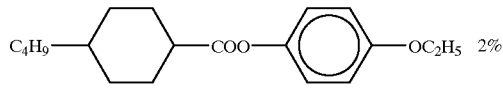 2%
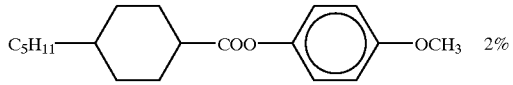 2%
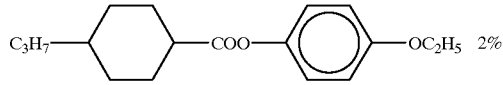 2%
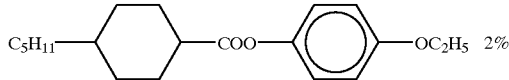 2%
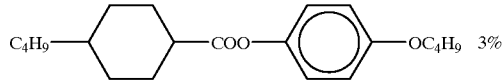 3%

-continued
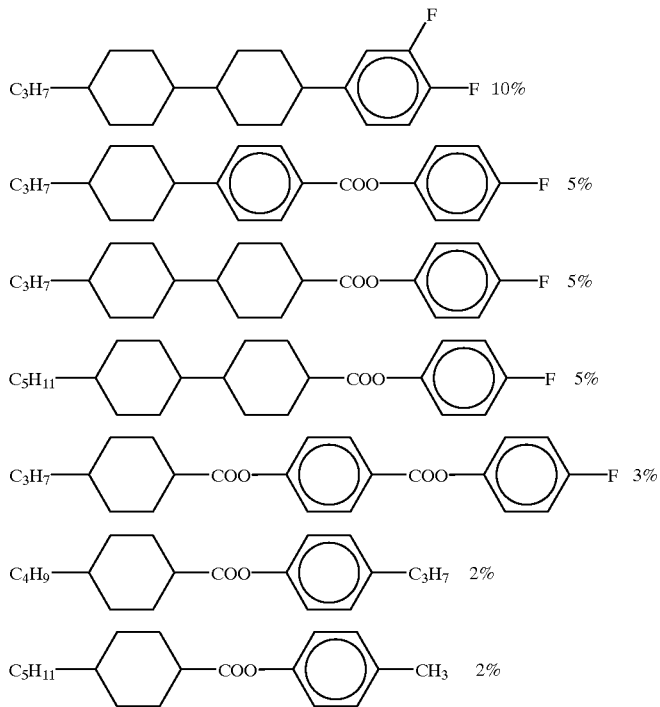
Example 13 (Composition Example 10)
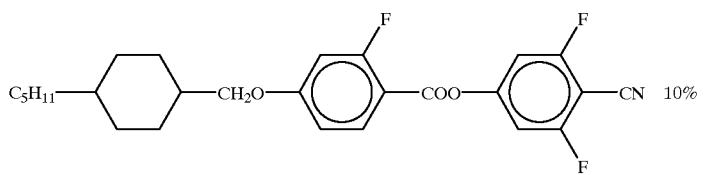
(77)
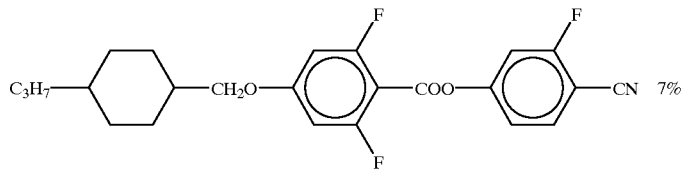
(109)
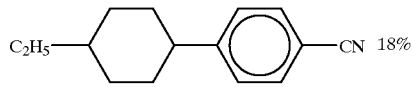
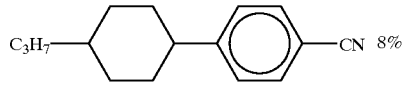
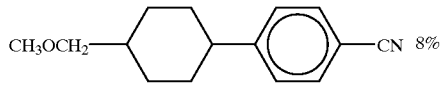
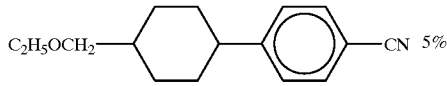

-continued
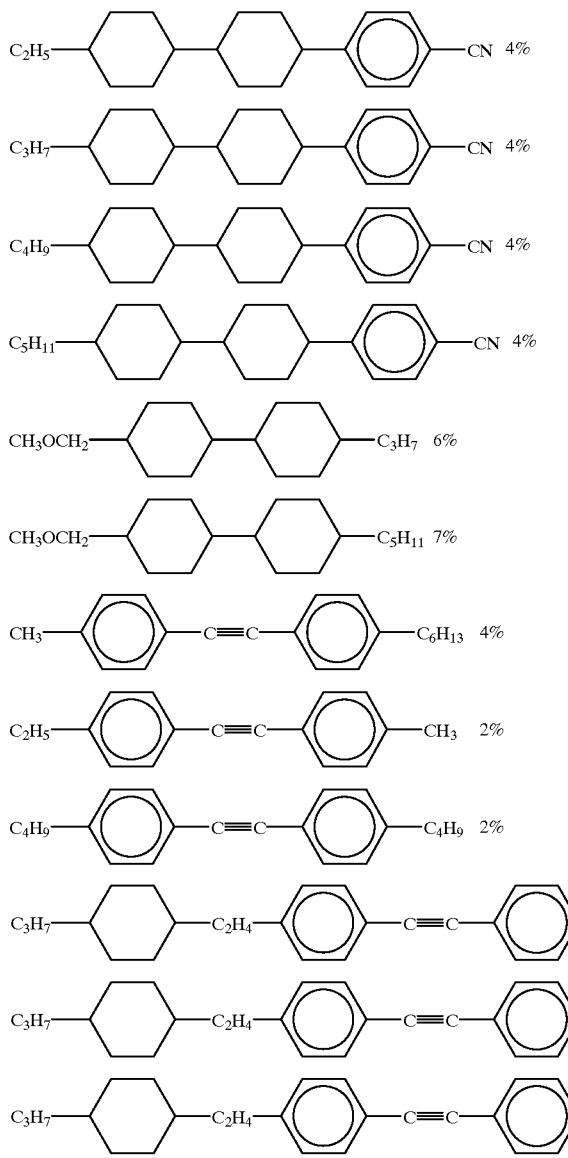
Example 14 (Composition Example 11)
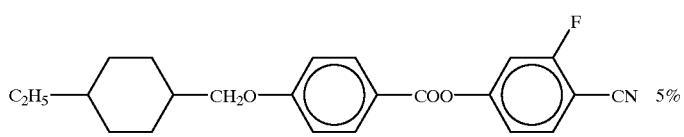
(1)
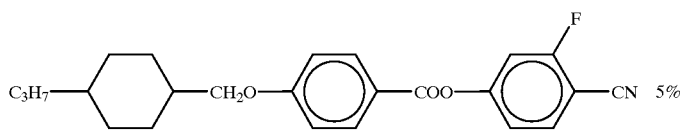
(162)

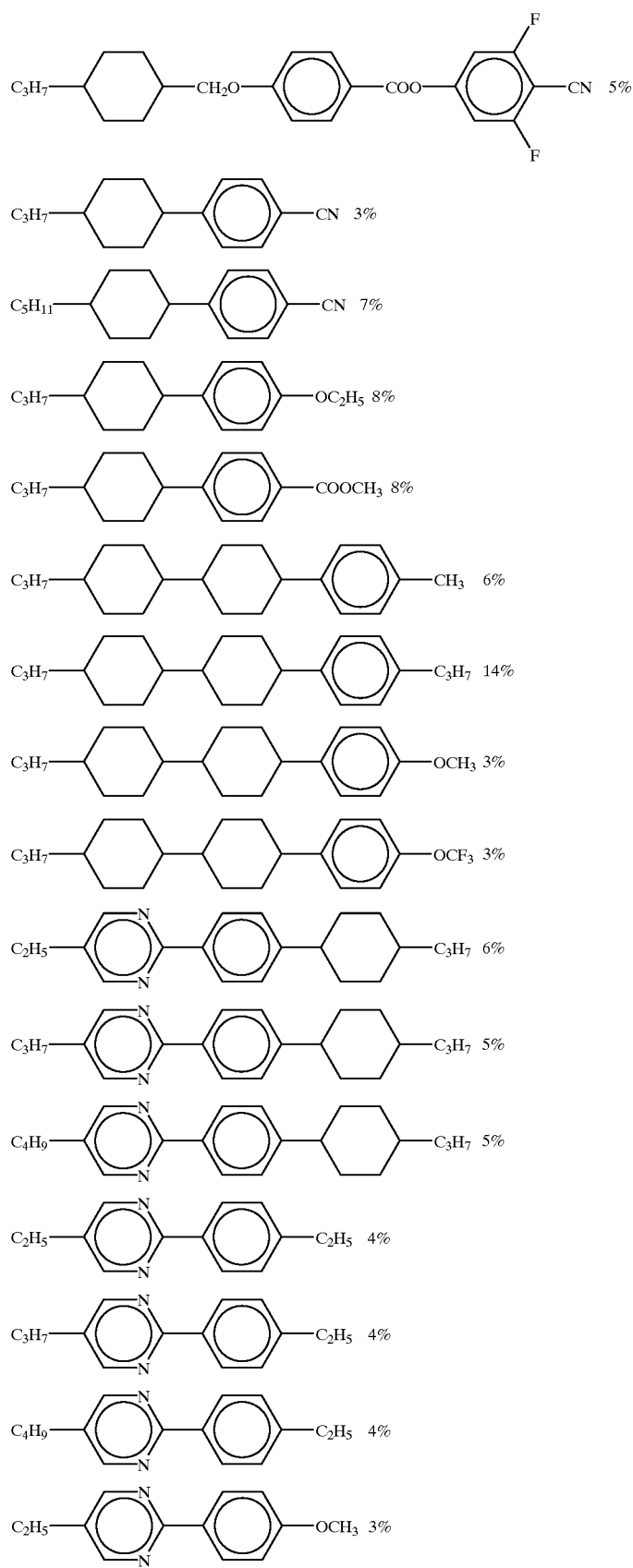

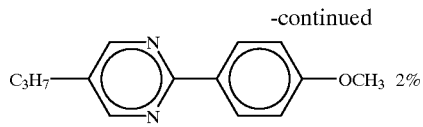 2%
Example 15 (Composition Example 12)
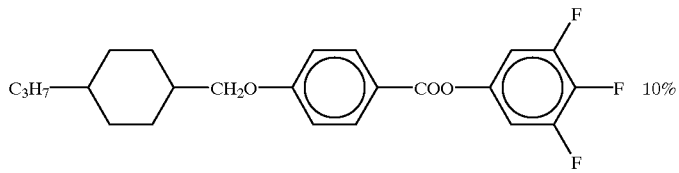 (39) 10%
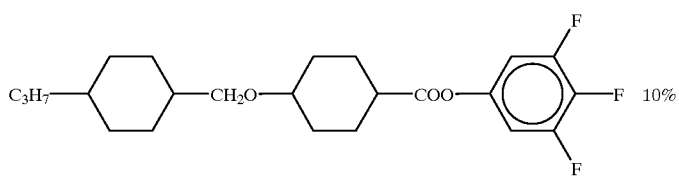 (208) 10%
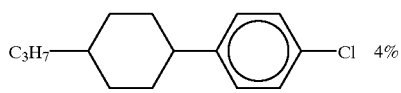 4%
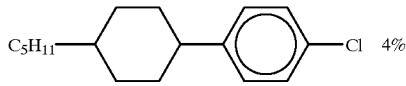 4%
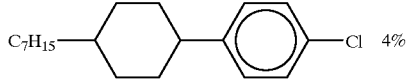 4%
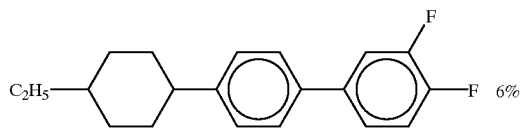 6%
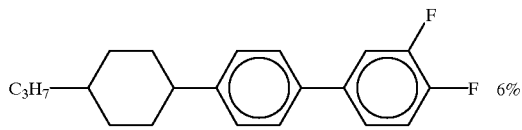 6%
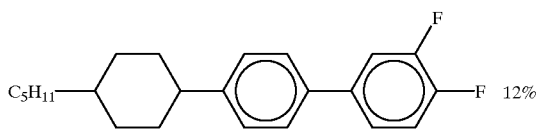 12%
 4%
 6%
 5%

-continued
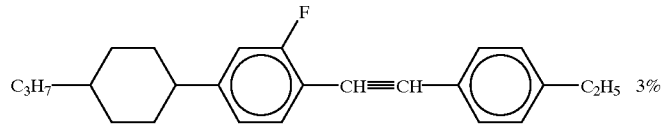 3%
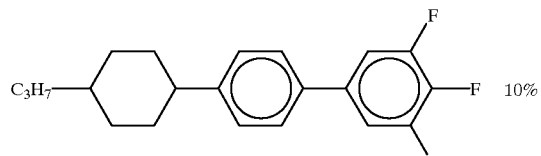 10%
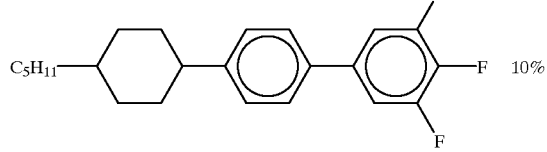 10%
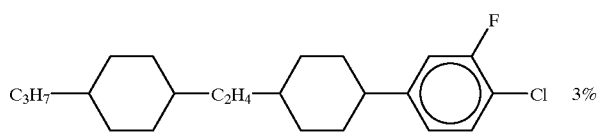 3%
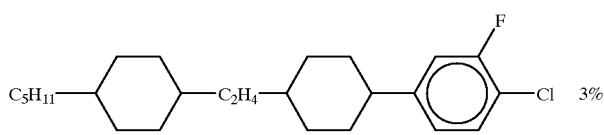 3%
Example 16 (Composition Example 13)
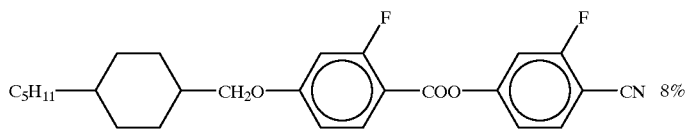 8% (59)
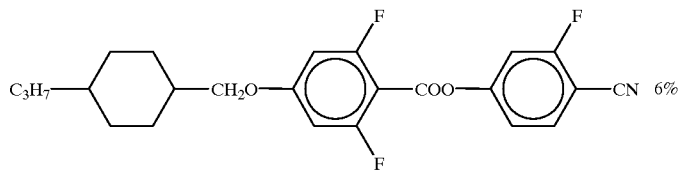 6% (109)
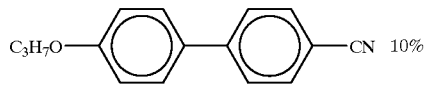 10%
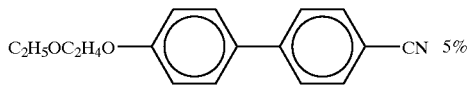 5%
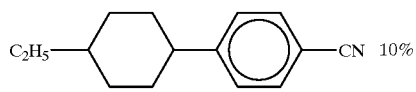 10%
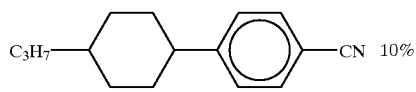 10%

-continued
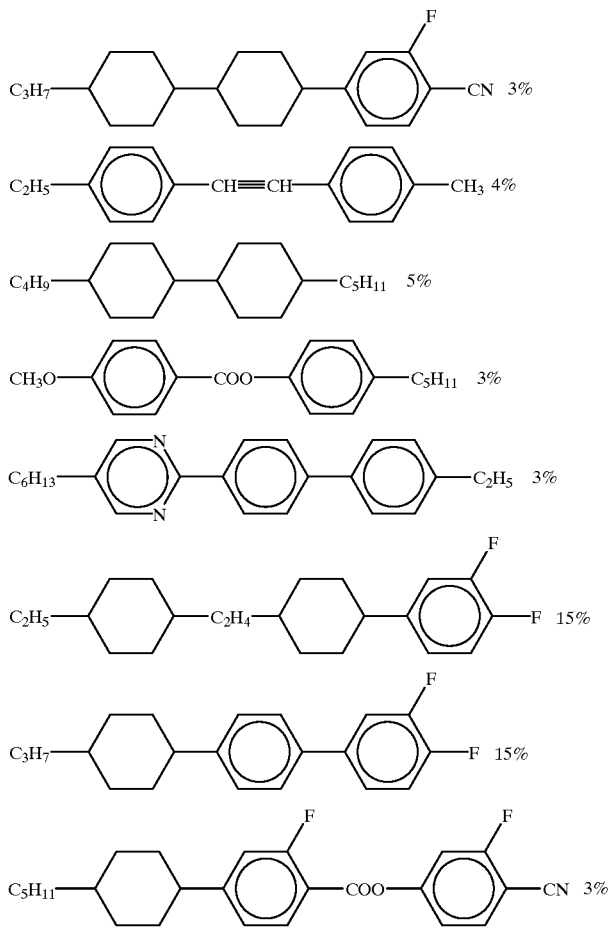
Example 17 (Composition Example 14)
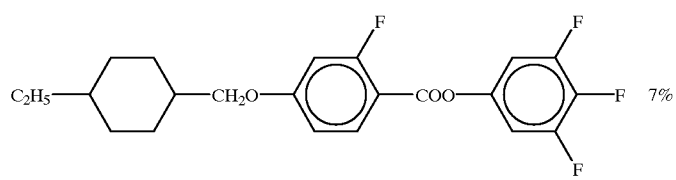
(92) 7%
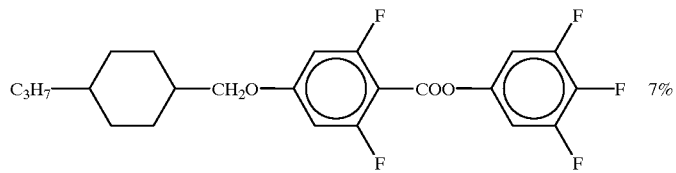
(146) 7%
8%

-continued
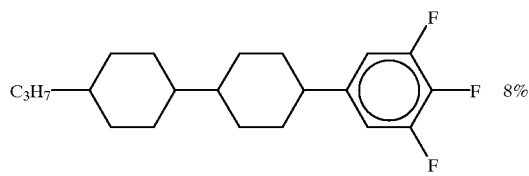 8%
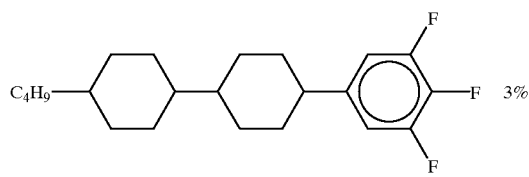 3%
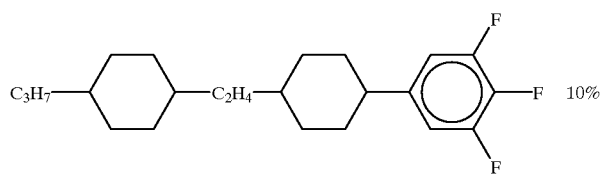 10%
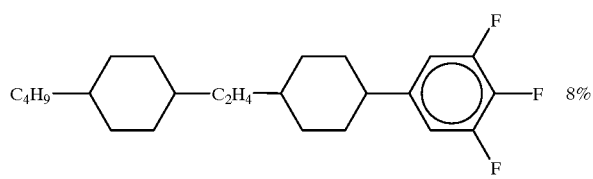 8%
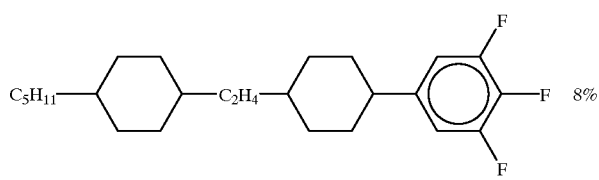 8%
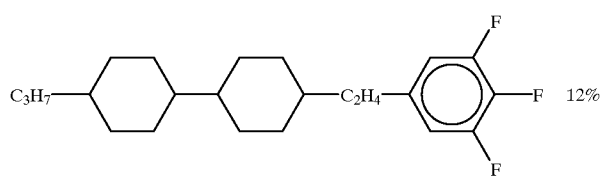 12%
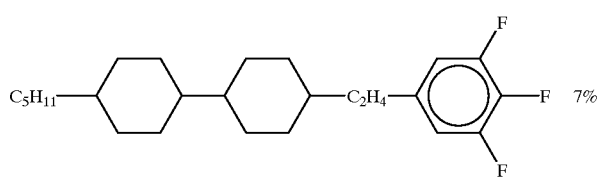 7%
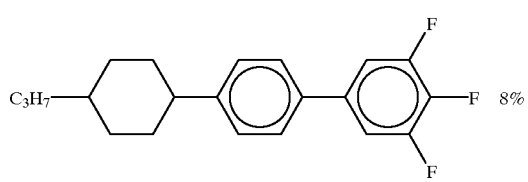 8%
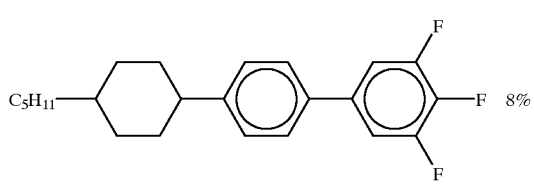 8%

-continued
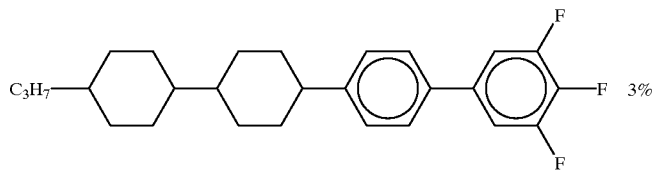 3%
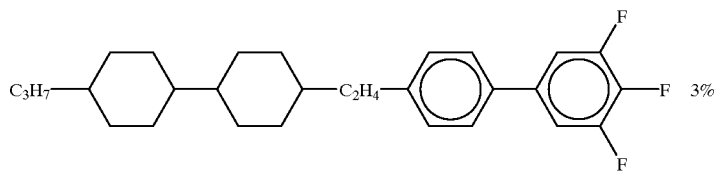 3%
Example 18 (Composition Example 15)
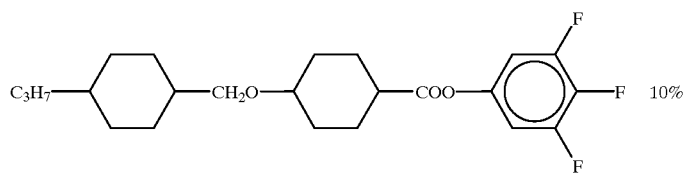 (208)
10%
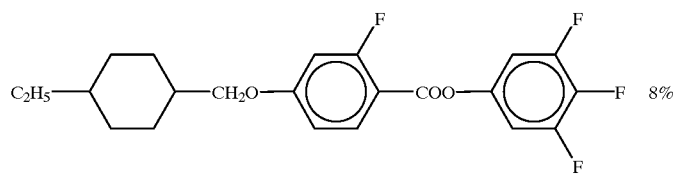 (92)
8%
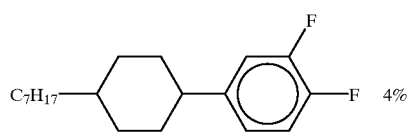 4%
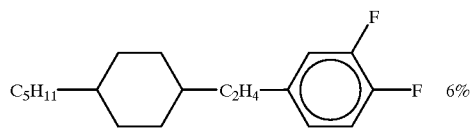 6%
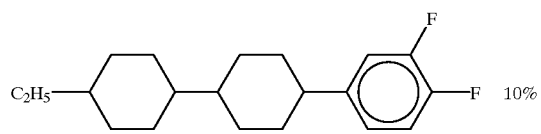 10%
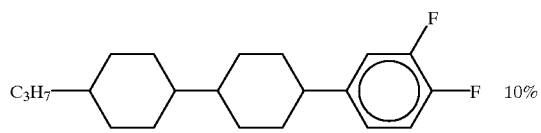 10%
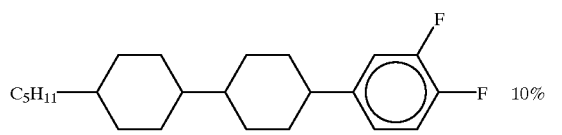 10%
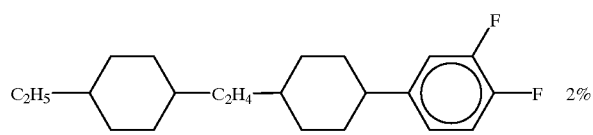 2%

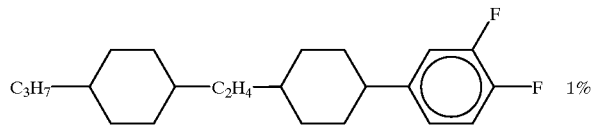 1%
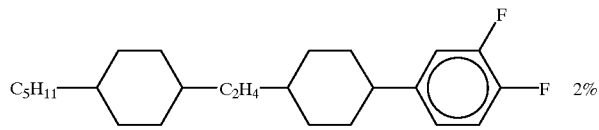 2%
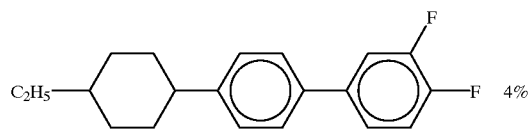 4%
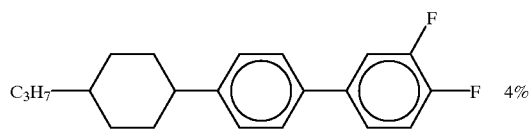 4%
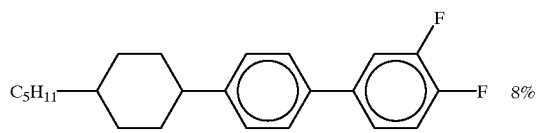 8%
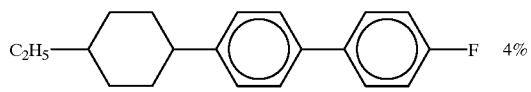 4%
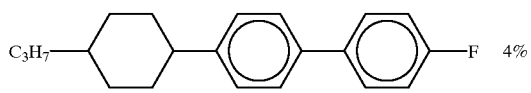 4%
 2%
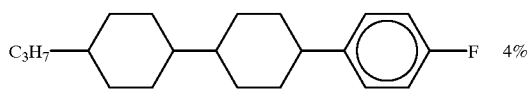 4%
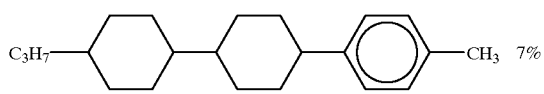 7%
Example 19 (Composition Example 16)
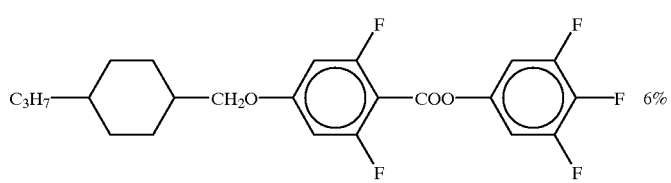 6%
(146)
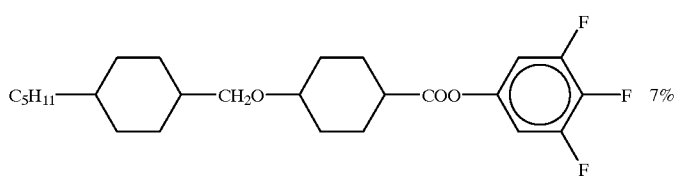 7%
(210)

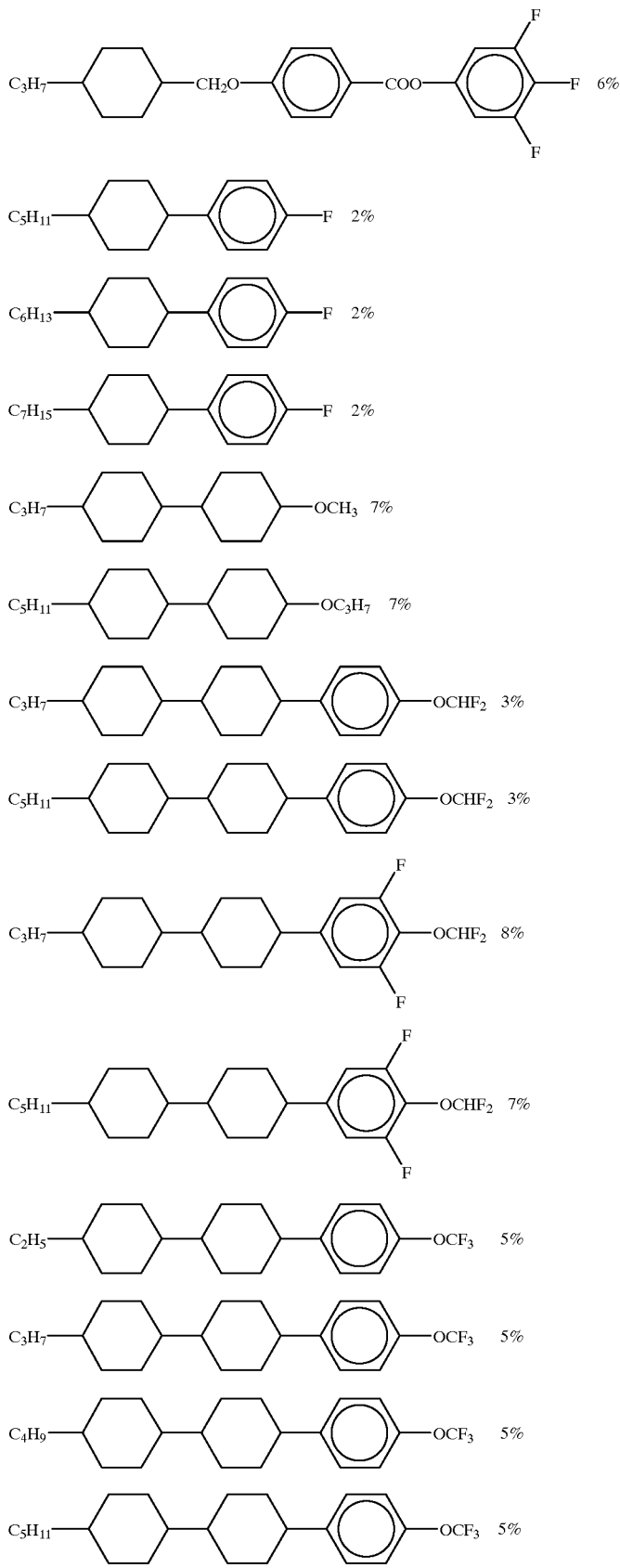

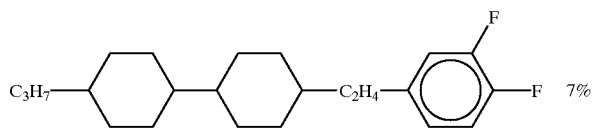 7%
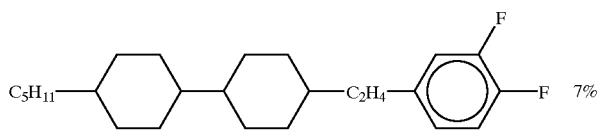 7%
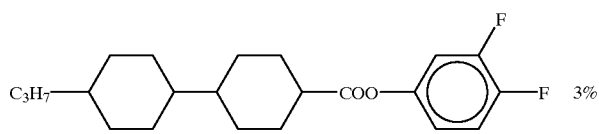 3%
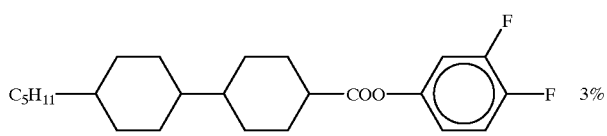 3%
Example 20 (Composition Example 17)
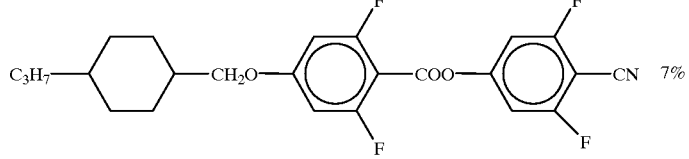 (129) 7%
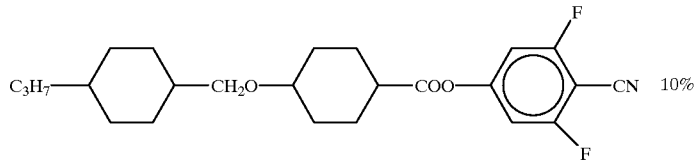 (186) 10%
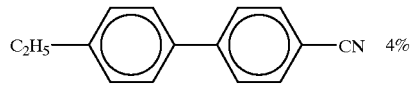 4%
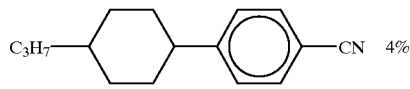 4%
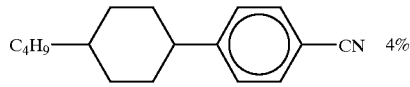 4%
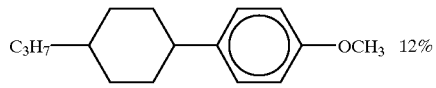 12%
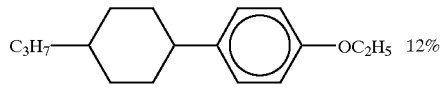 12%
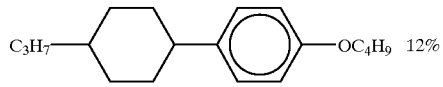 12%

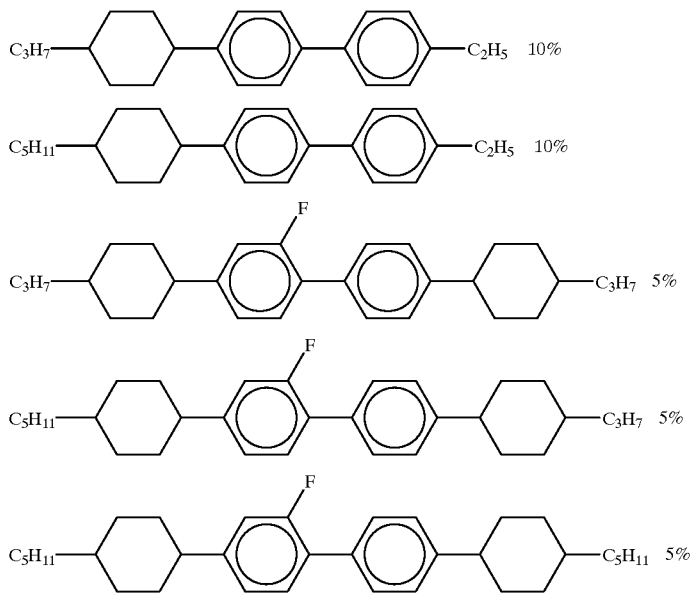
Example 21 (Composition Example 18)
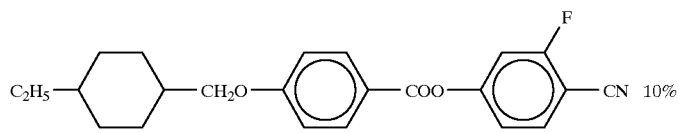
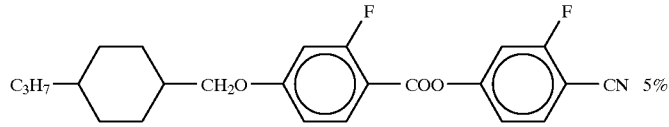
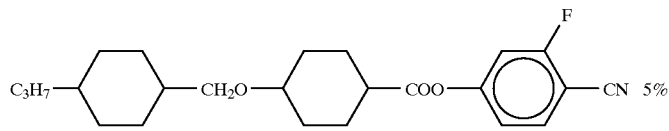
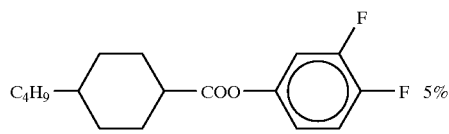
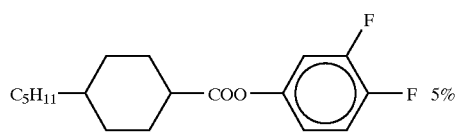
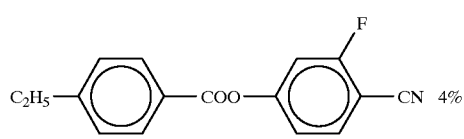

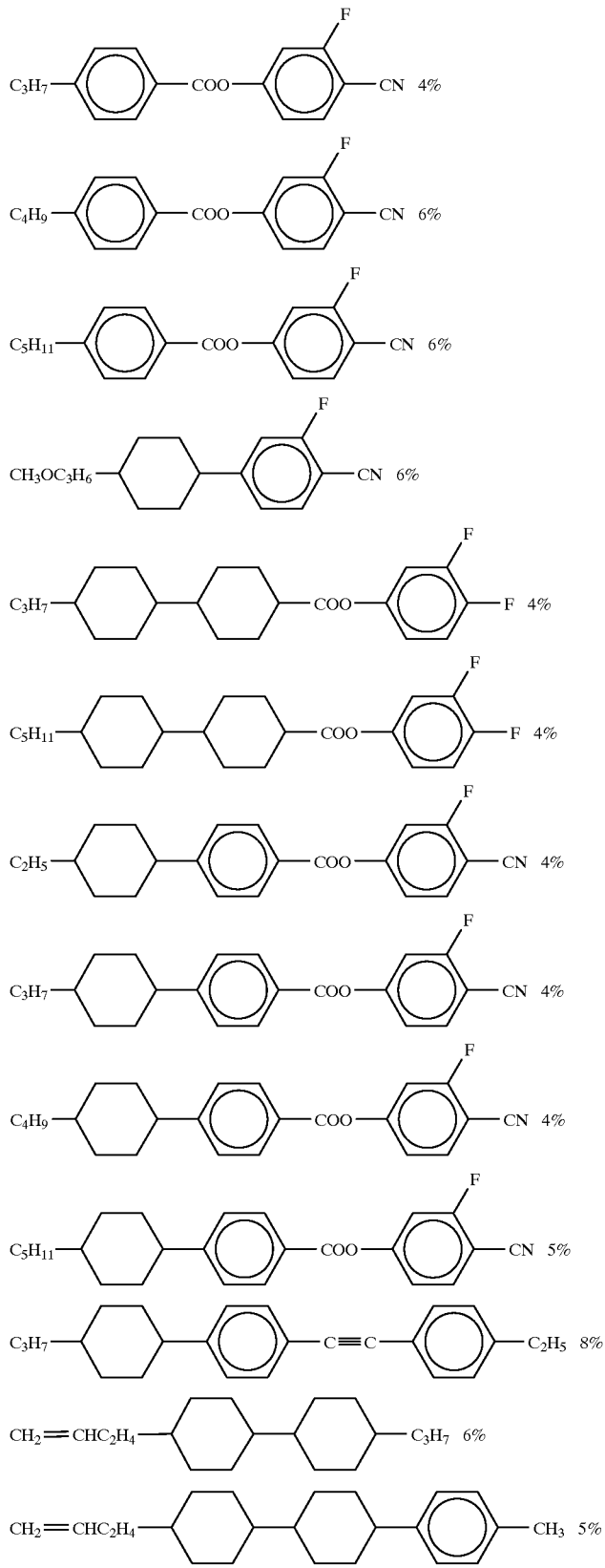

Example 22 (Composition Example 19)
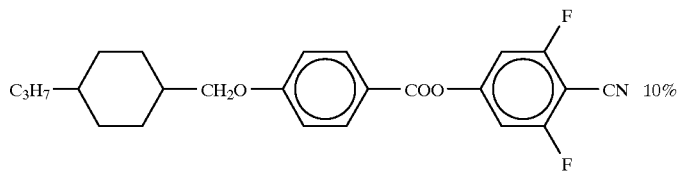 (21) 10%
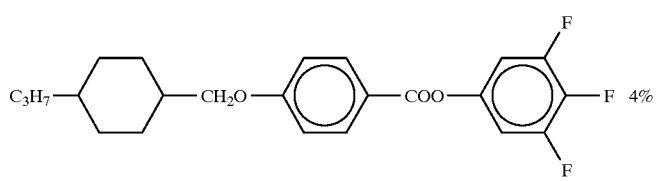 (208) 4%
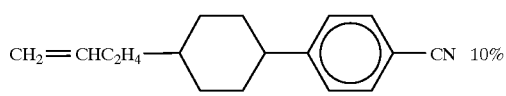 10%
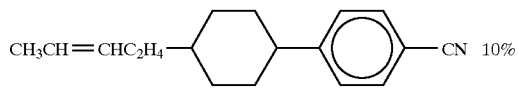 10%
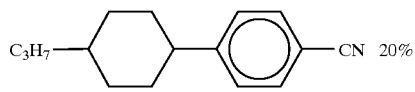 20%
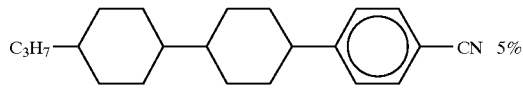 5%
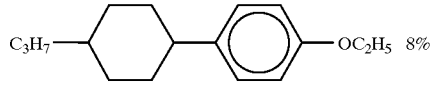 8%
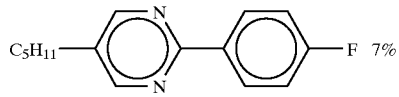 7%
 7%
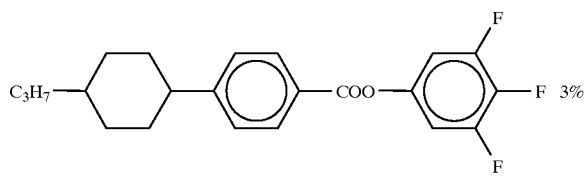 3%
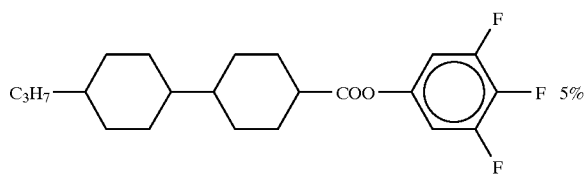 5%
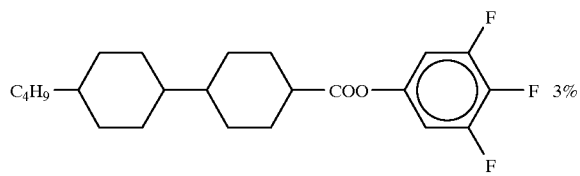 3%

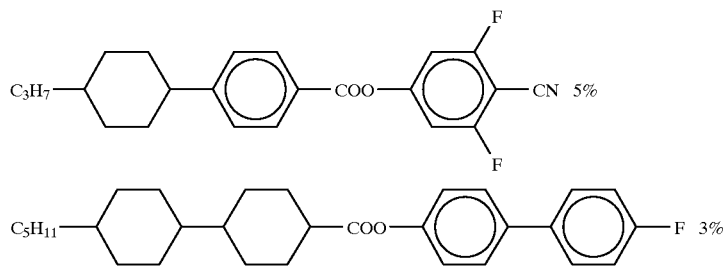

A liquid crystal composition comprising the compound according to the present invention is further exemplified below. In the examples given below, the components are expressed according to the regulated notation shown in the following Table 1.

The chiral compounds, CM33 and CN, represent the following compounds, respectively.

TABLE 1

Notation of Compounds using symbols

| (1) Left-Terminal Group | Symbol | (3) Bonding Group | Symbol |
|---|---|---|---|
| $C_aH_{2a+1}$— | a- | —$CH_2O$— | E |
| $C_aH_{2a+1}O$— | aO— | —$(CH_2)_4$— | 4 |
| $C_aH_{2a+1}OC_bH_{2b}$— | aOb— | —$CH_2CH_2$— | 2 |
| $CH_2$=CH— | V— | —COO— | E |
| $CH_2$=$CHC_aH_{2a}$— | Va— | —C≡C— | T |
| $C_aC_{2a+1}CH$=$CHC_bH_{2b}$— | aVb— | —CH=CH— | V |
| $C_aH_{2a+1}CH$=$CHC_bH_{2b}CH$=$CHC_dH_{2d}$— | aVbVc— | —$CF_2O$— | CF2O |

| (2) Ring Structure —(An)— | Symbol | (4) Right-Terminal Group | Symbol |
|---|---|---|---|
| (benzene) | B | —F<br>—Cl | —F<br>—CL |
| (difluorobenzene) | B(F) | —CN<br>—$CF_3$<br>—$OCF_3$ | —C<br>—CF3<br>—OCF3 |
| (trifluorobenzene) | B(F,F) | —$OCF_2H$<br>—$C_wH_{2w+1}$ | —OCF2H<br>-w |
| (cyclohexane) | H | —$OC_wH_{2w+1}$<br>—$COOCH_3$ | —Ow<br>—EMe |
| (pyrimidine) | Py | —CH=$CF_2$<br>—C≡C—CN | —VFF<br>—TC |

TABLE 1-continued

Notation of Compounds using symbols

| Structure | Symbol | Group | Notation |
|---|---|---|---|
| (1,3-dioxane ring) | G | —CH₂CH₂CH=CF₂ | —2VFF |
| | | —CH=CHCH₂CH₂F | —V2F |

(5) Examples of Notation

Ex. 1
3-H2B(F,F)B(F)—F $C_3H_7$—(cyclohexyl)—$CH_2CH_2$—(phenyl with 2,6-F)—(phenyl with 3,4-F)—F

Ex. 2
3-HB(F)TB-2

$C_3H_7$—(cyclohexyl)—(phenyl with F)—C≡C—(phenyl)—$C_2H_5$

Ex. 3
1V2-BEB(F,F)—C $CH_3CH=CHCH_2CH_2$—(phenyl)—COO—(phenyl with 3,5-F)—CN

---

CM33

$C_6H_{13}O$—(phenyl)—CO—O—(phenyl)—CO—O—$\overset{*}{C}H(CH_3)$—$C_6H_{13}$

CN (cholesteryl nonanoate-type structure with $C_8H_{17}$ ester)

In the following Composition Examples, $T_{NI}$, η, Δn, Δε, $V_{th}$, P represent clearing temperature (° C.), viscosity (mPa·s), optical anisotropy, dielectric anisotropy, threshold voltage (V) and helical pitch length (μm), respectively.

Example 23 (Composition Example 20)

| Component | % |
|---|---|
| 2-H1OBEB(F)-C (Compound 1) | 4.0% |
| 3-H1OBEB(F,F)-F (Compound 39) | 4.0% |
| 1V2-BEB(F,F)-C | 5.0% |
| 3-HB-C | 21.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-HB(F)TB-2 | 6.0% |
| 3-HB(F)TB-3 | 6.0% |

$T_{NI}$ = 90.8 (° C.)
η = 21.5 (mPa.s)
Δn = 0.160
Δε = 7.9
$V_{th}$ = 1.98 (V)

When 0.8 parts by weight of CM33 was added to 100 parts by weight of the above composition, pitch (P) was found to be 11 μm.

Example 24 (Composition Example 21)

| Component | % |
|---|---|
| 3-H1OHEB(F,F)-F (Compound 39) | 5.0% |
| 2O1-BEB(F)-C | 5.0% |
| 3O1-BEB(F)-C | 15.0% |
| 4O1-BEB(F)-C | 13.0% |
| 5O1-BEB(F)-C | 13.0% |
| 2-HHB(F)-C | 15.0% |
| 3-HHB(F)-C | 10.0% |
| 3-HB(F)TB-2 | 4.0% |
| 3-HB(F)TB-3 | 4.0% |
| 3-HB(F)TB-4 | 4.0% |

-continued

| | |
|---|---|
| 3-HHB-1 | 8.0% |
| 3-HHB-O1 | 4.0% |
| $T_{NI}$ = 87.9 (° C.) | |
| η = 88.8 (mPa.s) | |
| Δn = 0.148 | |
| Δε = 31.2 | |
| $V_{th}$ = 0.86 (V) | |

Example 25 (Composition Example 22)

| | |
|---|---|
| 2-H1OB(F)EB(F,F)-F (Compound 92) | 3.0% |
| 3-H1OHEB(F)-C (Compound 162) | 3.0% |
| 3-H1OHEB(F,F)-F (Compound 39) | 3.0% |
| 5-PyB-F | 4.0% |
| 3-PyB(F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 3-HHB-1 | 6.0% |
| 3-HHB-3 | 5.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |
| $T_{NI}$ = 90.3 (° C.) | |
| η = 42.5 (mPa.s) | |
| Δn = 0.196 | |
| Δε = 7.1 | |
| $V_{th}$ = 2.18 (V) | |

Example 26 (Composition Example 23)

| | |
|---|---|
| 5-H1OBEB(F,F)-CF3 (Compound 228) | 4.0% |
| 2-H1OBEB(F)-C (Compound 1) | 4.0% |
| 3-GB-C | 10.0% |
| 4-GB-C | 10.0% |
| 2-BEB-C | 12.0% |
| 3-BEB-C | 4.0% |
| 3-PyB(F)-F | 6.0% |
| 3-HEB-O4 | 8.0% |
| 4-HEB-O2 | 6.0% |
| 5-HEB-O1 | 6.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 3.0% |
| 3-HHEBB-C | 3.0% |
| 3-HBEBB-C | 3.0% |
| 5-HBEBB-C | 3.0% |
| $T_{NI}$ = 69.8 (° C.) | |
| η = 46.8 (mPa.s) | |
| Δn = 0.126 | |

-continued

| | |
|---|---|
| Δε = 13.2 | |
| $V_{th}$ = 1.22 (V) | |

Example 27 (Composition Example 24)

| | |
|---|---|
| 3-H1OBEB(F,F)-F (Compound 39) | 3.0% |
| 3-H1OHEB(F)-C (Compound 162) | 3.0% |
| 3-HB-C | 16.0% |
| 7-HB-C | 3.0% |
| 1O1-HB-C | 10.0% |
| 3-HB(F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 4.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |
| $T_{NI}$ = 80.1 (° C.) | |
| η = 23.3 (mPa.s) | |
| Δn = 0.141 | |
| Δε = 8.8 | |
| $V_{th}$ = 1.66 (V) | |

Example 28 (Composition Example 25)

| | |
|---|---|
| 2-H1OBEB(F)-C (Compound 1) | 2.0% |
| 2-H1OB(F)EB(F,F)-F (Compound 92) | 2.0% |
| 3-H1OHEB(F,F)-F (compound 208) | 2.0% |
| 2O1-BEB(F)-C | 5.0% |
| 3O1-BEB(F)-C | 12.0% |
| 5O1-BEB(F)-C | 4.0% |
| 1V2-BEB(F,F)-C | 8.0% |
| 3-HH-EMe | 10.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 2O1-HBEB(F)-C | 2.0% |
| 3-HB(F)EB(F)-C | 2.0% |
| 3-HBEB(F,F)-C | 2.0% |
| 3-HHB-F | 4.0% |
| 3-HHB-O1 | 4.0% |
| 3-HHB-3 | 9.0% |
| 3-HEBEB-F | 2.0% |
| 3-HEBEB-1 | 2.0% |
| $T_{NI}$ = 75.9 (° C.) | |
| η = 40.0 (mPa.s) | |
| Δn = 0.115 | |
| Δε = 23.3 | |
| $V_{th}$ = 1.00 (V) | |

Example 29 (Composition Example 26)

| | |
|---|---|
| 2-H1OBEB(F)-C (Compound 1) | 3.0% |
| 3-H1OBEB(F,F)-F (Compound 39) | 3.0% |
| 3-H1OHEB(F)-C (Compound 162) | 3.0% |
| 2O1-BEB(F)-C | 5.0% |
| 3O1-BEB(F)-C | 12.0% |
| 5O1-BEB(F)-C | 4.0% |
| 1V2-BEB(F,F)-C | 13.0% |
| 3-HB-O2 | 10.0% |
| 3-HH-4 | 3.0% |
| 3-HHB-F | 3.0% |
| 3-HHB-1 | 6.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-HB(F)TB-2 | 5.0% |

$T_{NI} = 91.4$ (° C.)
$\eta = 47.7$ (mPa.s)
$\Delta n = 0.141$
$\Delta \epsilon = 28.0$
$V_{th} = 1.02$ (V)

Example 30 (Compound Example 27)

| | |
|---|---|
| 3-H1OBEB(F,F)-F (Compound 39) | 4.0% |
| 2-H1OB(F)EB(F,F)-F (Compound 92) | 4.0% |
| 2-BEB-C | 12.0% |
| 3-BEB-C | 4.0% |
| 4-BEB-C | 6.0% |
| 3-HB-C | 28.0% |
| 3-HEB-O4 | 12.0% |
| 4-HEB-O2 | 8.0% |
| 5-HEB-O1 | 3.0% |
| 3-HEB-O2 | 6.0% |
| 5-HEB-O2 | 5.0% |
| 3-HHB-1 | 4.0% |
| 3-HHB-O1 | 4.0% |

$T_{NI} = 60.1$ (° C.)
$\eta = 31.8$ (mPa.s)
$\Delta n = 0.114$
$\Delta \epsilon = 11.3$
$V_{th} = 1.31$ (V)

Example 31 (Composition Example 28)

| | |
|---|---|
| 2-H1OBEB(F)-C (Compound 1) | 5.0% |
| 3-H1OHEB(F)-C (Compound 162) | 5.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 3.0% |

$T_{NI} = 66.8$ (° C.)
$\eta = 31.2$ (mPa.s)
$\Delta n = 0.166$
$\Delta \epsilon = 8.6$
$V_{th} = 1.55$ (V)

Example 32 (Composition Example 29)

| | |
|---|---|
| 3-H1OBEB(F,F)-F (Compound 39) | 5.0% |
| 3-H1OHEB(F)-C (Compound 162) | 5.0% |
| 2-HB-C | 5.0% |
| 3-HB-C | 12.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 11.0% |
| 3-HHEB-F | 4.0% |
| 5-HHEB-F | 4.0% |
| 2-HHB(F)-F | 7.0% |
| 3-HHB(F)-F | 7.0% |
| 3-HHB(F,F)-F | 5.0% |

$T_{NI} = 99.8$ (° C.)
$\eta = 26.8$ (mPa.s)
$\Delta n = 0.105$
$\Delta \epsilon = 6.1$
$V_{th} = 2.32$ (V)

Example 33 (Composition Example 30)

| | |
|---|---|
| 3-H1OBEB(F,F)-F (Compound 39) | 5.0% |
| 2-H1OB(F)EB(F,F)-F (Compound 92) | 5.0% |
| 2-HHB(F)-F | 17.0% |
| 3-HHB(F)-F | 17.0% |
| 5-HHB(F)-F | 16.0% |
| 2-H2HB(F)-F | 10.0% |
| 3-H2HB(F)-F | 5.0% |
| 2-HBB(F)-F | 6.0% |
| 3-HBB(F)-F | 6.0% |
| 5-HBB(F)-F | 13.0% |

$T_{NI} = 96.4$ (° C.)
$\eta = 33.8$ (mPa.s)
$\Delta n = 0.097$
$\Delta \epsilon = 6.4$
$V_{th} = 2.05$ (V)

When 0.3 parts by weight of CN was added to 100 parts by weight of the above composition, pitch (P) was found to be 79 μm.

Example 34 (Composition Example 31)

| | |
|---|---|
| 5-H1OBEB(F,F)-CF3 (Compound 228) | 5.0% |
| 3-H1OHEB(F,F)-F (Compound 208) | 5.0% |
| 7-HB(F,F)-F | 3.0% |
| 3-HB-O2 | 7.0% |
| 2-HHB(F)-F | 10.0% |

-continued

| | |
|---|---|
| 3-HHB(F)-F | 10.0% |
| 5-HHB(F)-F | 10.0% |
| 2-HBB(F)-F | 9.0% |
| 3-HBB(F)-F | 9.0% |
| 5-HBB(F)-F | 6.0% |
| 2-HBB-F | 4.0% |
| 3-HBB-F | 4.0% |
| 5-HBB-F | 3.0% |
| 3-HBB(F,F)-F | 5.0% |
| 5-HBB(F,F)-F | 10.0% |

$T_{NI} = 84.2$ (° C.)
$\eta = 30.2$ (mPa.s)
$\Delta n = 0.112$
$\Delta \epsilon = 7.4$
$V_{th} = 1.81$ (V)

Example 35 (Composition Example 32)

| | |
|---|---|
| 3-H1OBEB(F,F)-F (Compound 39) | 5.0% |
| 2-H1OB(F)EB(F,F)-F (Compound 92) | 5.0% |
| 3-H1OHEB(F,F)-F (Compound 208) | 5.0% |
| 7-HB(F,F)-F | 3.0% |
| 3-H2HB(F,F)-F | 12.0% |
| 4-H2HB(F,F)-F | 10.0% |
| 5-H2HB(F,F)-F | 5.0% |
| 3-HHB(F,F)-F | 5.0% |
| 4-HHB(F,F)-F | 5.0% |
| 3-HH2B(F,F)-F | 5.0% |
| 5-HH2B(F,F)-F | 10.0% |
| 3-HBB(F,F)-F | 12.0% |
| 5-HBB(F,F)-F | 12.0% |
| 3-HBCF2OB(F,F)-F | 6.0% |

$T_{NI} = 70.4$ (° C.)
$\eta = 34.3$ (mPa.s)
$\Delta n = 0.092$
$\Delta \epsilon = 10.2$
$V_{th} = 1.41$ (V)

Example 36 (Composition Example 33)

| | |
|---|---|
| 3-H1OBEB(F,F)-F (Compound 39) | 5.0% |
| 2-H1OB(F)EB(F,F)-F (Compound 92) | 5.0% |
| 3-H1OHEB(F,F)-F (Compound 208) | 5.0% |
| 3-HB-CL | 10.0% |
| 5-HB-CL | 4.0% |
| 7-HB-CL | 4.0% |
| 1O1-HH-5 | 5.0% |
| 2-HBB(F)-F | 8.0% |
| 3-HBB(F)-F | 8.0% |
| 5-HBB(F)-F | 4.0% |
| 4-HHB-CL | 8.0% |
| 5-HHB-CL | 3.0% |
| 3-H2HB(F)-CL | 4.0% |
| 3-HBB(F,F)-F | 10.0% |
| 5-H2BB(F,F)-F | 9.0% |
| 3-HB(F)VB-2 | 4.0% |
| 3-HB(F)VB-3 | 4.0% |

$T_{NI} = 84.0$ (° C.)
$\eta = 28.9$ (mPa.s)
$\Delta n = 0.124$
$\Delta \epsilon = 7.0$
$V_{th} = 2.02$ (V)

Example 37 (Composition Example 34)

| | |
|---|---|
| 2-H1OB (F) EB (F, F) -F (Compound 92 ) | 3.0% |
| 3-H1OHEB (F, F) -F (Compound 162) | 3.0% |
| 3-HHB (F, F) -F | 9.0% |
| 3-H2HB (F, F) -F | 8.0% |
| 4-H2HB (F, F) -F | 8.0% |
| 5-H2HB (F, F) -F | 2.0% |
| 3-HBB (F, F) -F | 21.0% |
| 5-HBB (F, F) -F | 20.0% |
| 3-H2BB (F, F) -F | 10.0% |
| 5-HHBB (F, F) -F | 3.0% |
| 5-HHEBB-F | 2.0% |
| 3-HH2BB (F, F) -F | 3.0% |
| 1O1-HBBH-4 | 4.0% |
| 1O1-HBBH-5 | 4.0% |

$T_{NI} = 97.1$ (° C.)
$\eta = 38.6$ (mPa · s)
$\Delta n = 0.118$
$\Delta \epsilon = 9.6$
$V_{th} = 1.67$ (V)

Example 38 (Composition Example 35)

| | |
|---|---|
| 3-H1OHEB (F, F) -F (Compound 162) | 5.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 3-HH2B-OCF3 | 4.0% |
| 5-HH2B-OCF3 | 4.0% |
| 3-HHB (F, F) -OCF3 | 5.0% |
| 3-HBB (F) -F | 10.0% |
| 5-HBB (F) -F | 10.0% |
| 3-HH2B (F) -F | 3.0% |
| 3-HB (F) BH-3 | 3.0% |
| 5-HBBH-3 | 3.0% |
| 3-HHB (F, F) -OCF2H | 4.0% |

$T_{NI} = 84.8$ (° C.)
$\eta = 18.6$ (mPa · s)
$\Delta n = 0.094$
$\Delta \epsilon = 5.2$
$V_{th} = 2.21$ (V)

Example 39 (Composition Example 36)

| | |
|---|---|
| 3-H1OBEB (F, F) -F (Compound 39) | 4.0% |
| 2-H1OB (F) EB (F, F) -F (Compound 92) | 4.0% |
| 3-H1OHEB (F, F) -F (Compound 208) | 4.0% |
| 2-HHB (F) -F | 2.0% |
| 3-HHB (F) -F | 2.0% |
| 5-HHB (F) -F | 2.0% |
| 2-HBB (F) -F | 6.0% |
| 3-HBB (F) -F | 6.0% |
| 5-HBB (F) -F | 10.0% |
| 2-H2BB (F) -F | 9.0% |
| 3-H2BB (F) -F | 9.0% |
| 3-HBB (F, F) -F | 25.0% |
| 5-HBB (F, F) -F | 10.0% |
| 1O1-HBBH-4 | 5.0% |
| 1O1-HBBH-5 | 2.0% |

$T_{NI}$ = 92.8 (° C.)
η = 41.5 (mPa · s)
Δn = 0.133
Δε = 8.6
$V_{th}$ = 1.72 (V)

Example 40 (Composition Example 37)

| | |
|---|---|
| 2-H1OBEB (F) -C (Compound 1) | 5.0% |
| 3-H1OBEB (F, F) -F (Compound 39) | 5.0% |
| 2-H1OB (F) EB (F, F) -F (Compound 92) | 5.0% |
| 3-H1OHEB (F) -C (Compound 162) | 5.0% |
| 3-H1OHEB (F, F) -F (Compound 208) | 5.0% |
| 2-HB-C | 5.0% |
| 3-HB-C | 12.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 10.0% |
| 3-HHEB-F | 4.0% |
| 5-HHEB-F | 4.0% |
| 3-HHB (F, F) -F | 5.0% |

$T_{NI}$ = 98.9 (° C.)
η = 39.1 (mPa · s)
Δn = 0.110
Δε = 8.4
$V_{th}$ = 2.08 (V)

Example 41 (Composition Example 38)

| | |
|---|---|
| 2-H1OBEB (F) -C (Compound 1) ) | 10.0% |
| 3-H1OBEB (F, F) -F (Compound 39) | 5.0% |
| 2-H1OB (F) EB (F, F) -F (Compound 92) | 10.0% |
| 3-H1OHEB (F) -C (Compound 162) | 10.0% |
| 3-H1OHEB (F, F) -F (Compound 208) | 5.0% |
| 2-HHB (F) -F | 17.0% |
| 3-HHB (F) -F | 16.0% |
| 2-H2HB (F) -F | 10.0% |
| 3-H2HB (F) -F | 5.0% |
| 2-HBB (F) -F | 6.0% |
| 3-HBB (F) -F | 6.0% |

$T_{NI}$ = 99.6 (° C.)
η = 57.6 (mPa · s)
Δn = 0.109
Δε = 11.7
$V_{th}$ = 1.45 (V)

Feasibility for the Industrial Use

The compound of the present invention exhibits large dielectric anisotropy, low threshold voltage, and favorable temperature-dependency of threshold voltage, as well as a favorable miscibility with known liquid crystal compounds, and therefore a liquid crystal composition comprising the compound can provide low voltage-operable liquid crystal display elements.

What is claimed is:

1. A compound represented by the following formula (I):

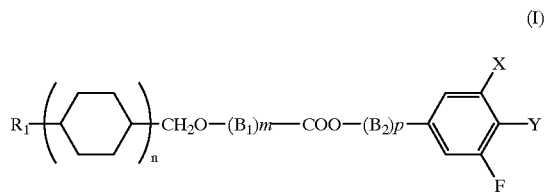

(I)

wherein $B_1$ and $B_2$ represent independently trans-1,4-cyclohexylene group or 1,4-phenylene group, wherein the six-membered ring is optionally substituted by one or more halogen atom, Y represents a halogen-substituted alkyl group having 1 to 3 carbon atoms, a cyano group, a fluorine atom or chlorine atom, X represents a fluorine atom, chlorine atom or a hydrogen atom, $R_1$ represents an alkyl group having 1 to 10 carbon atoms or an alkoxy group having 1 to 10 carbon atoms, n and m represent independently 1 or 2 and p represents 0 or 1, provided that, when n and m represent 1, p represents 0, $B_1$ represents a 1,4-phenylene group and Y represents a fluorine atom or a cyano group, X is F or Cl.

2. The compound according to claim 1 wherein m represents 1.

3. The compound according to claim 2 characterized in that $B_1$ represents a 1,4-phenylene group wherein at least one hydrogen atom on the six-membered ring is optionally substituted by a halogen atom.

4. The compound according to claim 3 characterized in that $B_1$ represents a 1,4-phenylene group wherein at least one hydrogen atom on the six-membered ring is substituted by a fluorine atom.

5. The compound according to claim 2 wherein $B_1$ represents a trans-1,4-cyclohexylene group.

6. The compound according to claim 1 wherein m represents 2.

7. A liquid crystal composition comprising at least one compound according to claim 1.

8. A liquid crystal composition comprising at least one compound according to claim 1 as a first component, and as a second component at least one compound selected from the group consisting of the compounds of the formula (II), (III) or (IV):

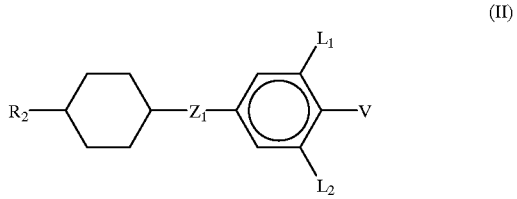

(II)

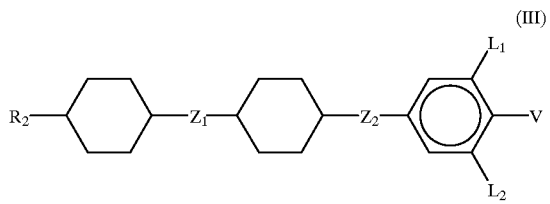

(III)

-continued

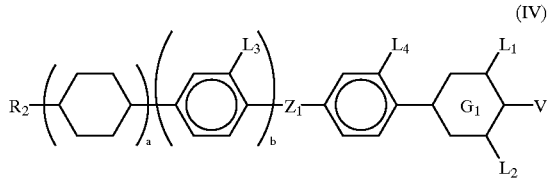
(IV)

wherein $R_2$ represents an alkyl group having 1 to 10 carbon atoms, V represents F, Cl, $CF_3$, $OCF_3$, $OCF_2H$ or an alkyl group having 1 to 10 carbon atoms, $L_1$, $L_2$, $L_3$ and $L_4$ represent independently H or F, a represents 1 or 2, b represents 0 or 1, $Z_1$ and $Z_2$ represent independently —$CH_2CH_2$—, —CH=CH— or a covalent bond, and ring $G_1$ represents a trans-1,4-cyclohexylene group or a 1,4-phenylene group.

9. A liquid crystal composition comprising at least one compound according to claim 1 as a first component, and as a second component and at least one compound selected from the group consisting of the compounds of the formula (V), (VI), (VII), (VIII) or (IX):

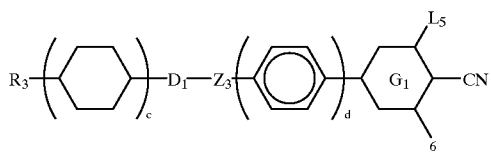
(V)

wherein $R_3$ represents F, an alkyl group having 1 to 10 carbon atoms or an alkenyl group having 2 to 10 carbon atoms, any methylene group (—$CH_2$—) in said alkyl or alkenyl group may be replaced by one or more oxygen atoms (—O—), provided that two or more successive methylene groups are not replaced by oxygen atoms, $Z_3$ represents —$CH_2CH_2$—, —CO—O— or a covalent bond, $L_5$ and $L_6$ represent independently H or F, $D_1$ represents a trans-1,4-cyclohexylene, 1,4-phenylene or trans 1,3-dioxane-2,5-diyl group, ring $G_2$ represents a trans-1,4-cyclohexylene, or 1,4-phenylene group, and c and d represent independently 0 or 1,

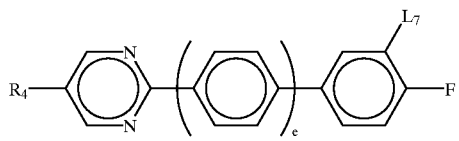
(VI)

wherein $R_4$ represents an alkyl group having 1 to 10 carbon atoms, $L_7$ represents H or F, and e represents 0 or 1,

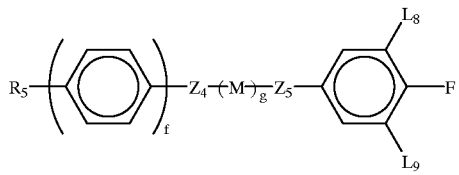
(VII)

wherein $R_5$ represents an alkyl group having 1 to 10 carbon atoms, M represents a trans-1,4-cyclohexylene or 1,4-phenyelne group, $L_8$ and $L_9$ represent independently H or F, $Z_4$ represents —CO—O— or a covalent bond, $Z_5$ represents —CO—O— or —C≡C—, and f and g represent independently 0 or 1,

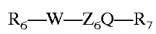
(VIII)

wherein $R_6$ and $R_7$ represent independently an alkyl group having 1 to 10 carbon atoms, an alkoxy group having 1 to 10 carbon atoms or an alkoxymethyl group having 1 to 10 carbon atoms, W represents a trans-1,4-cyclohexylene, 1,4-phenylene or 1,3-pyrimidine-2,5-diyl group, Q represents a trans-1,4-cyclohexylene or 1,4-phenylene, and $Z_6$ represents —C≡C—, —CO—O—, —$CH_2CH_2$— or a covalent bond,

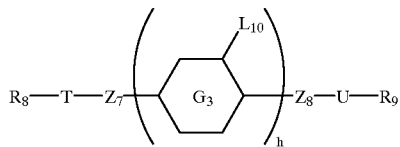
(IX)

wherein $R_8$ represents an alkyl group having 1 to 10 carbon atoms or an alkoxy group having 1 to 10 carbon atoms, $R_9$ represents an alkyl group having 1 to 10 carbon atoms, any methylene group (—$CH_2$—) in $R_9$ may be replaced by an oxygen atom (—O—), provided that two or more successive methylene groups are not replaced by oxygen atoms, T represents a trans-1,4-cyclohexylene group or 1,3-pyrimidine-2,5-diyl group, ring $G_3$ and U represent independently a trans-1,4-cyclohexylene group or a 1,4-phenylene group, $Z_7$ represents —$CH_2CH_2$—, —CH=CH—, —CO—O— or a covalent bond, $Z_8$ represents —C≡C—, —CO—O— or a covalent bond, h represents 0 or 1, and $L_{10}$ represents H or F.

10. A liquid crystal display element wherein the liquid crystal composition according to claim 7 is used.

11. A liquid crystal composition comprising a first component, a second component and a third component, wherein the first component is at least one compound according to claim 1;

the second component is at least one compound selected from the group consisting of compounds of formulae (II), (III) and (IV):

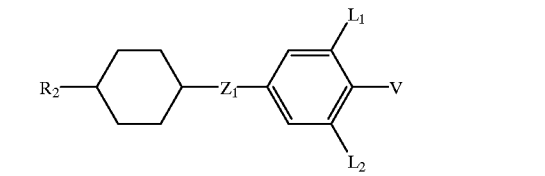
(II)

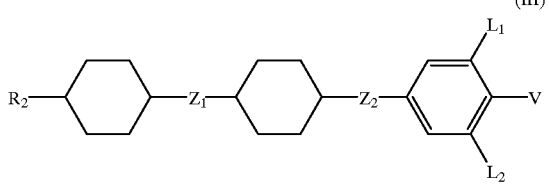
(III)

(IV)

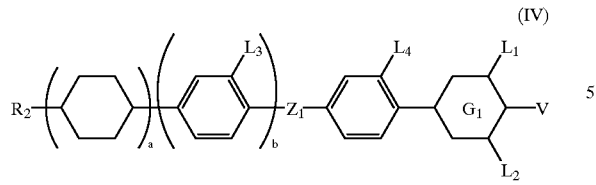

wherein $R_2$ represents an alkyl group having 1 to 10 carbon atoms, V represents F, Cl, $CF_3$, $OCF_3$, $OCF_2H$, or an alkyl group having 1 to 10 carbon atoms, $L_1$, $L_2$, $L_3$, and $L_4$ represent independently H or F, "a" represents 1 or 2, b represents 0 or 1, $Z_1$ and $Z_2$ represent independently $-CH_2CH_2-$, $-CH=CH-$, or a covalent bond, and ring $G_1$ represents a trans-1,4-cyclohexylene group or a 1,4-phenylene group; and the third component is at least one compound selected from the group consisting of compounds of formulae (V), (VI), (VII), (VIII) and (XI):

(V)

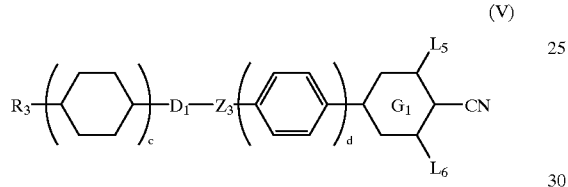

wherein $R_3$ represents F, an alkyl group having 1 to 10 carbon atoms, or an alkenyl group having 2 to 10 carbon atoms, any methylene ($-CH_2-$) group in said alkyl or alkenyl group may be replaced by one or more oxygen atoms ($-O-$), provided that two or more successive methylene groups are not replaced by oxygen atoms, $Z_3$ represents $-CH_2CH_2-$, $-CO-O-$, or a covalent bond, $L_5$ and $L_6$ represent independently H or F, $D_1$ represents a trans-1,4-cyclohexylene, 1,4-phenylene or trans-1,3-dioxane-2,5-diyl group, ring $G_2$ represents a trans-1,4-cyclohexylene, or 1,4-phenylene group, and c and d represent independently 0 or 1;

(VI)

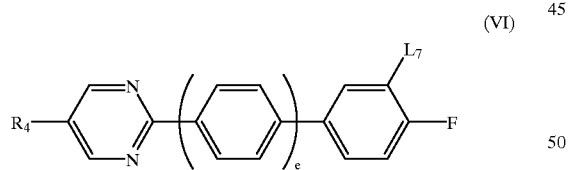

wherein $R_4$ represents an alkyl group having 1 to 10 carbon atoms, $L_7$ represents H or F, and e represents 0 or 1;

(VII)

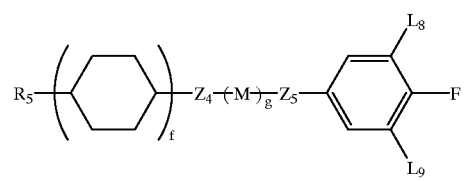

wherein $R_5$ represents an alkyl group having 1 to 10 carbon antoms, M represents a trans-1,4-cyclohexylene or 1,4-phenylene group, $L_8$ and $L_9$ represent independently H or F, $Z_4$ represents $-CO-O-$ or a covalent bond, $Z_5$ represents $-CO-O-$ or $-C\equiv C-$, and f and g represent independently 0 or 1;

 (VIII)

wherein $R_6$ and $R_7$ represent independently an alkyl group having 1 to 10 carbon atoms, an alkoxy group having 1 to 10 carbon atoms or an alkoxymethyl group having 1 to 10 carbon atoms, W represents a trans-1,4-cyclohexylene, a 1,4-phenylene, or -a 1,3-pyrimidine-2,5-diyl group, Q represents a trans-1,4-cyclohexylene or a 1,4-phenylene group, and $Z_6$ represents $-C\equiv C-$, $-CO-O-$, $-CH_2CH_2-$, or a covalent bond;

(IX)

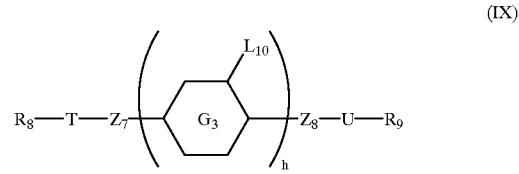

wherein $R_8$ represents an alkyl group having 1 to 10 carbon atoms or an alkoxy group having 1 to 10 carbon atoms, $R_9$ represents an alkyl group having 1 to 10 carbon atoms, any methylene group ($-CH_2-$) in $R_9$ may be replaced by an oxygen atom ($-O-$), provided that two or more successive methylene groups are not replaced by oxygen atoms, T represents a trans-1,4-cyclohexylene or a 1,3-pyrimidinyl-2,5-diyl group, rings $G_3$ and U represent independently a trans-1,4-cyclohexylene group or a 1,4-phenylene group, $Z_7$ represents $-CH_2CH_2-$, $-C\equiv C-$, $-CO-O-$, or a covalent bond, $Z_8$ represents $-C\equiv C-$, $-CO-O-$, or a covalent bond, h represents 0 or 1 and $L_{10}$ represents H or F.

* * * * *